US007026460B2

(12) United States Patent
Roberts et al.

(10) Patent No.: US 7,026,460 B2
(45) Date of Patent: Apr. 11, 2006

(54) LOVE VARIANT REGULATOR MOLECULES

(75) Inventors: Shannon Roberts, Cambridge, MA (US); Amir Sherman, Jerusalem (IL); Joshua Trueheart, Concord, MA (US); G. Todd Milne, Brookline, MA (US)

(73) Assignee: Microbia, Inc., Cambridge, MA (US)

( * ) Notice: Subject to any disclaimer, the term of this patent is extended or adjusted under 35 U.S.C. 154(b) by 283 days.

(21) Appl. No.: 09/974,760

(22) Filed: Oct. 9, 2001

(65) Prior Publication Data

US 2003/0143705 A1 Jul. 31, 2003

(51) Int. Cl.
*C07H 21/04* (2006.01)

(52) U.S. Cl. .................. 536/23.1; 435/320.1; 435/243; 435/254.1; 435/254.3

(58) Field of Classification Search .............. 536/23.1; 435/320.1, 243, 254.1, 254.3, 4, 6, 440
See application file for complete search history.

(56) References Cited

U.S. PATENT DOCUMENTS

| | | | |
|---|---|---|---|
| 4,554,101 A | 11/1985 | Hopp | |
| 5,849,541 A | * 12/1998 | Vinci et al. | ................ 435/91.1 |
| 6,391,583 B1 | 5/2002 | Hutchinson et al. | ....... 435/69.1 |
| 2003/0143705 A1 | 7/2003 | Roberts et al. | |

FOREIGN PATENT DOCUMENTS

| | | |
|---|---|---|
| WO | WO00/37629 | 12/1999 |
| WO | WO 02/24865 A2 | 3/2002 |

OTHER PUBLICATIONS

Everett et al. Pendred syndrome is caused by mutations in a putative sulphate transporter gene (PDS). Nature Genetics 17: 411–422, 1997.*
Scott et al. The pendred syndrome gene encodes a chloride–iodide trasnport protein. Nature Genetics 21: 440–443, 1999.*
Kyte et al. (1982), "A Simple Method for Displaying the Hydropathic Character of a Protein," *Mol. Biol.* 157:105–132.
Muhlrad et al. (1992), "A Rapid Method for Localized Mutagenesis of Yeast Genes," *Yeast* 8:79–82.
Su et al. (1993), "Identification of Functionally Related Genes That Stimulate Early Meiotic Gene Expression in Yeast," *Genetics* 133:67–77.
Woloshuk et al. (1994), "Molecular Characterization of aflR, a Regulatory Locus for Aflatoxin Biosynthesis," *Appl. Environ. Microbiol.* 60:2408–2414.
Tilburn et al. (1995), "The Aspergillus PacC zinc finger transcription factor mediates regulation of both acid– and alkaline expressed genes by ambient pH," 14 *EMBO J.* 4:779–790.

Brown et al. (1996), "Twenty–five coregulated transcripts define a sterigmatocystin gene cluster in *Aspergillus nidulans,*" *Proc. Natl. Acad. Sci. USA* 93:1418–1422.
MacCabe et al. (1996), "Identification, cloning and analysis of the *Aspergillus niger* gene pacC, a wide domain regulatory gene responsive to ambient pH," *Mol. Gen. Genet.* 250:367–374.
Suarez et al. (1996), "Characterization of a *Penicillium chrysogenum* gene encoding a PacC transcription factor and its binding sites in the divergent pcbAB–pcbC promoter of the penicillin biosynthetic cluster," *Mol. Microbiol.* 20:529–540.
Lambert et al. (1997), "Genetic Analysis of Regulatory Mutants Affecting Synthesis of Extracellular Proteinases in the Yeast *Yarrowia lipolytica:* Identification of a RIM101/pacC Homolog," *Mol. Cell Biol.* 17:3966–3976.
Trapp et al. (1998), "Characterization of the gene cluster for biosynthesis of macrocyclic trichothecenes in *Myrothecium roridum,*"*Mol. Gen Genet.* 257:421–432.
Hendrickson et al. (1999), "Lovastatin biosynthesis in *Aspergillus terreus:* characterization of blocked mutants, enzyme activities and a multifunctional polyketide synthase gene," *Chem. Biol.* 6:429–439.
Kennedy et al. (1999), "Modulation of Polyketide Synthase Activity by Accessory Proteins During Lovastatin Biosynthesis," *Science* 284:1368–1372.
Litzka et al. (1999), "Transcriptional control of expression of fungal B–lactam biosynthesis genes," *Antonie van Leeuwenhoek* 75:95–105.
Matsumoto et al. (1999), "The Trichothecene Biosynthesis Regulatory Gene from the Type B Producer Fusarium Strains: Sequence of Tri6 and Its Expression in *Escherichia coli,*" *Biosci. Biotechnol. Biochem.* 63:2001–2004.
Hutchinson et al. (2000), "Aspects of Biosynthesis of Non–Aromatic Fungal Polyketides by Iterative Polyketide Synthases," *Antonie van Leeuwenhoek* 78:287–295.
Lesova et al. (2000), "Factors affecting the production of (—)–mitorubrinic acid by *Penicillium funiculosum,*" *J. Basic Microbiol.* 40:369–375.
Schmitt et al. (2000), "The Fungal CPCR1 Protein, Which Binds Specifically to B–Lactam Biosynthesis Genes, Is Related to Human Regulatory Factor X Transcription Factors," *J. Biol. Chem.* 275:9348–9357.
Tag et al. (2000), "G–protein signaling mediates differential production of toxic secondary metabolites," *Mol. Microbiol.* 38:658–665.

(Continued)

*Primary Examiner*—James Ketter
*Assistant Examiner*—David Lambertson
(74) *Attorney, Agent, or Firm*—Fish & Richardson P.C.

(57) ABSTRACT

The invention provides variant regulator proteins of secondary metabolite production and nucleic acids encoding said variant regulator proteins. In particular, the invention provides variant regulator molecules of the lovE protein.

36 Claims, 9 Drawing Sheets

OTHER PUBLICATIONS

Brown et al. (2001), "A Genetic and Biochemical Approach to Study Trichothecene Diversity in *Fusarium sporotrichioides* and *Fusarium graminearum," Fungal Genet.* 257:421–432.

Sutherland et al. (2001), "Recent Advances in the Biosynthetic Studies of Lovastatin," 4 *Curr. Opinion in Drug Discovery & Dev.* 2:229–236.

Hajjaj et al. (2001), "Lovastatin Biosynthesis by *Aspergillus terreus* in a Chemically Defined Medium," *Appl. Environ. Microbiol.* 67:2596–2602.

Robinson et al. (2001), "Solid–state fermentation: a promising microbial technology for secondary metabolite production," *Appl. Microbiol. Biotechnol.* 55:284–289.

Waters (2001), "Are We Aggressive Enough in Lowering Cholesterol?"*Am. J. Cardiol.* 88:10F–5F.

Young et al. (2001), "Molecular cloning and genetic analysis of an indolediterpene gene cluster from *Penicillium paxilli," Mol. Microbiol.* 39:754–764.

Hendrickson et al., "Lovastatin Biosynthesis in *Aspergillus terreus:* Characterization of Blocked Mutants . . . " Chem. Biol. 6(7):429–39, 1999.—Abstract Only.

Accession No.: AF151722; GI: 5106754; Hendrickson et al., Jun. 20, 1999.

Accession No.: AAD34559; GI: 4959952; Hutchinson et al., Jun. 2, 1999.

Accession No.: AF141924; GI: 4959940; Hutchinson et al., Jun. 2, 1999.

Brachmann et al., "Designer Deletion Strains derived from *Saccharomyces cerevisiae* S288C: . . . " Yeast 14:115–132, 1998.

Drocourt et al., "Cassettes of *Streptoalloteichus hindustanus ble* gene . . . " Nucl. Acids Res. 18(13):4009, 1990.

Hoffman et al., "A ten–minute DNA preparation from yeast efficiently releases autonomous plasmids . . . ". Gene 57:267–272, 1987.

Mumberg et al., "Regulatable promoters of *Saccharomyces cerevisiae*; . . . " Nucl. Acids Res. 22(25):5767–5768, 1994.

Myers et al., "Yeast shuttle and integrative vectors with multiple cloning sites suitable for construction of *lacZ* fusions" Gene 45:299–310, 1986.

Sikorski et al., "A system of shuttle vectors and yeast host strains designed for efficient manipulation of DNA in *Saccharomyces cerevisiae*" Genetics 122:19–27, 1989.

Woods et al., "High–efficiency transformation of plasmid DNA into yeast" Methods in Mol. Biol. 177:85–97, 2001.

Xiao et al., "Conditional gene targeted deletion by Cre recombinase demonstrates . . . " Nucl. Acids Res. 25(15):2985–2991, 1997.

* cited by examiner

SEQUENCE LISTING

<160> NUMBER OF SEQ ID NOS: 92

<210> SEQ ID NO 1
<211> LENGTH: 46
<212> TYPE: DNA
<213> ORGANISM: Artificial Sequence
<220> FEATURE:
<223> OTHER INFORMATION: primer

<400> SEQUENCE: 1
ggccatggag gccgctagct cgagtcgacg gcctaggtgg ccagct                    46

<210> SEQ ID NO 2
<211> LENGTH: 46
<212> TYPE: DNA
<213> ORGANISM: Artificial Sequence
<220> FEATURE:
<223> OTHER INFORMATION: primer

<400> SEQUENCE: 2
ggccacctag gccgtcgact cgagctagcg gcctccatgg ccgtac                    46

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
ggcggccgct ctagaactag tctcgagggt acc                                  33

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
ggtaccctcg agactagttc tagagcggcc gcc                                  33

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
cacagcggcc gctcaacctt cccattgggg c                                    31

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
caccactagt acgcgggctg attcgac                                         27

<210> SEQ ID NO 7
<211> LENGTH: 33

<212> TYPE: DNA
<213> ORGANISM: Artificial Sequence
<220> FEATURE:
<223> OTHER INFORMATION: primer

<400> SEQUENCE: 7
caccactagt tatacattat ataaagtaat gtg                          33

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
cacaggatcc gtcatctttg ccttcgttta tc                           32

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
cgcggatcct attgaacaag atggattgca c                            31

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
ccggaattca gaagaactcg tcaagaag                                28

<210> SEQ ID NO 11
<211> LENGTH: 40
<212> TYPE: DNA
<213> ORGANISM: Artificial Sequence
<220> FEATURE:
<223> OTHER INFORMATION: primer

<400> SEQUENCE: 11
acaaaaaagc aggctccaca atggctgcag atcaaggtat                   40

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
acaagaaagc tgggttcatg gaggaatatt gttga                        35

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13

```
gggatccaa tcgaggtcca cgaccagt                                    28
```

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14

```
ggggacaagt ttgtacaaaa aagcaggct                                  29
```

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15

```
ggggatccgc caatggtccc gttcaaac                                   28
```

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16

```
acaagaaagc tgggttcaca gaatgtttag ctcaa                           35
```

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17

```
ggggaccact ttgtacaaga aagctgggt                                  29
```

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18

```
gcgatgcccc aagcgcaagc tacgccaatc caggg                           35
```

<210> SEQ ID NO 19
<211> LENGTH: 35
<212> TYPE: DNA
<213> ORGANISM: Artificial Sequence
<220> FEATURE:
<223> OTHER INFORMATION: primer

<400> SEQUENCE: 19

```
cgtcgcgcca ttcgccattc aggctgcgca actgt                           35
```

<210> SEQ ID NO 20
<211> LENGTH: 31
<212> TYPE: DNA
<213> ORGANISM: Artificial Sequence

```
<220> FEATURE:
<223> OTHER INFORMATION: primer

<400> SEQUENCE: 20
ggacctttgc agcataaatt actatacttc t                              31

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
ggcgcgtcca ttcgccattc aggctgcgca actgt                          35

<210> SEQ ID NO 22
<211> LENGTH: 31
<212> TYPE: DNA
<213> ORGANISM: Artificial Sequence
<220> FEATURE:
<223> OTHER INFORMATION: primer

<400> SEQUENCE: 22
taaaactctt gttttcttct tttctctaaa t                              31

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
cagtgagcgc gcgtaatacg actcactata gggcga                         36

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
atacttctat agacacacaa acacaaatac acacac                         36

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
cgcggatccc gtcgttttac aac                                       23

<210> SEQ ID NO 26
<211> LENGTH: 31
<212> TYPE: DNA
<213> ORGANISM: Artificial Sequence
<220> FEATURE:
<223> OTHER INFORMATION: primer

<400> SEQUENCE: 26
cccaagctta ttattttga caccagacca a                               31
```

<210> SEQ ID NO 27
<211> LENGTH: 36
<212> TYPE: DNA
<213> ORGANISM: Artificial Sequence
<220> FEATURE:
<223> OTHER INFORMATION: primer

<400> SEQUENCE: 27
ggaagatcta gcatcgtggc caatttcttc tagttt 36

<210> SEQ ID NO 28
<211> LENGTH: 41
<212> TYPE: DNA
<213> ORGANISM: Artificial Sequence
<220> FEATURE:
<223> OTHER INFORMATION: primer

<400> SEQUENCE: 28
ataagaatgc ggccgctcaa ccttcccatt ggggcgtttg c 41

<210> SEQ ID NO 29
<211> LENGTH: 37
<212> TYPE: DNA
<213> ORGANISM: Artificial Sequence
<220> FEATURE:
<223> OTHER INFORMATION: primer

<400> SEQUENCE: 29
cacaggatcc agcattatta atttagtgtg tgtattt 37

<210> SEQ ID NO 30
<211> LENGTH: 28
<212> TYPE: DNA
<213> ORGANISM: Artificial Sequence
<220> FEATURE:
<223> OTHER INFORMATION: primer

<400> SEQUENCE: 30
caccactagt ctcgagcaga tccgccag 28

<210> SEQ ID NO 31
<211> LENGTH: 27
<212> TYPE: DNA
<213> ORGANISM: Artificial Sequence
<220> FEATURE:
<223> OTHER INFORMATION: primer

<400> SEQUENCE: 31
caccactagt acgcgggctg attcgac 27

<210> SEQ ID NO 32
<211> LENGTH: 31
<212> TYPE: DNA
<213> ORGANISM: Artificial Sequence
<220> FEATURE:
<223> OTHER INFORMATION: primer

<400> SEQUENCE: 32
cacagcggcc gctcaacctt cccattgggg c 31

<210> SEQ ID NO 33
<211> LENGTH: 35
<212> TYPE: DNA
<213> ORGANISM: Artificial Sequence
<220> FEATURE:
<223> OTHER INFORMATION: primer

<400> SEQUENCE: 33
ggccatcgat acaagtttgt acaaaaaagc tgaac                              35

<210> SEQ ID NO 34
<211> LENGTH: 33
<212> TYPE: DNA
<213> ORGANISM: Artificial Sequence
<220> FEATURE:
<223> OTHER INFORMATION: primer

<400> SEQUENCE: 34
ggcgccctat tacaccactt tgtacaagaa agc                                33

<210> SEQ ID NO 35
<211> LENGTH: 35
<212> TYPE: DNA
<213> ORGANISM: Artificial Sequence
<220> FEATURE:
<223> OTHER INFORMATION: primer

<400> SEQUENCE: 35
cacacgtctc cggcctcaac cttcccattg gggcg                              35

<210> SEQ ID NO 36
<211> LENGTH: 35
<212> TYPE: DNA
<213> ORGANISM: Artificial Sequence
<220> FEATURE:
<223> OTHER INFORMATION: primer

<400> SEQUENCE: 36
cacacagatc tcgtggccaa tttcttctag tttga                              35

<210> SEQ ID NO 37
<211> LENGTH: 37
<212> TYPE: DNA
<213> ORGANISM: Artificial Sequence
<220> FEATURE:
<223> OTHER INFORMATION: primer

<400> SEQUENCE: 37
cacacggatc cacaatgtta cgtcctgtag aaacccc                            37

<210> SEQ ID NO 38
<211> LENGTH: 34
<212> TYPE: DNA
<213> ORGANISM: Artificial Sequence
<220> FEATURE:
<223> OTHER INFORMATION: primer

<400> SEQUENCE: 38
cacagcggcc gcttcattgt ttgcctccct gctg                               34

<210> SEQ ID NO 39
<211> LENGTH: 34
<212> TYPE: DNA
<213> ORGANISM: Artificial Sequence
<220> FEATURE:
<223> OTHER INFORMATION: primer

<400> SEQUENCE: 39
gcggccgcgg cgcccggccc atgtcaacaa gaat                               34

<210> SEQ ID NO 40

-continued

```
<211> LENGTH: 25
<212> TYPE: DNA
<213> ORGANISM: Artificial Sequence
<220> FEATURE:
<223> OTHER INFORMATION: primer

<400> SEQUENCE: 40
ccgcggccga gtggagatgt ggagt                                              25

<210> SEQ ID NO 41
<211> LENGTH: 469
<212> TYPE: PRT
<213> ORGANISM: Artificial Sequence
<220> FEATURE:
<223> OTHER INFORMATION: synthetically generated variant

<400> SEQUENCE: 41
```

Met Ala Ala Asp Gln Gly Ile Phe Thr Asn Ser Val Thr Leu Ser Pro
 1               5                  10                  15

Val Glu Gly Ser Arg Thr Gly Gly Thr Leu Pro Arg Arg Ala Phe Arg
             20                  25                  30

Arg Ser Cys Asp Arg Cys His Ala Gln Lys Ile Lys Cys Thr Gly Asn
         35                  40                  45

Lys Glu Val Thr Gly Arg Ala Pro Cys Gln Arg Cys Gln Gln Ala Gly
     50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Ala Gln Ala Asp Cys Arg Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

-continued

His Ser Ser Val Asp Thr Ile Pro Phe Phe Ser Glu Asn Leu Pro Ile
            325                 330                 335

Gly Glu Leu Phe Pro Tyr Val Asp Pro Leu Thr His Ala Leu Phe Ser
            340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
            370                 375             380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
                435                 440                 445

Ile Phe Ser Leu Ala Arg Lys His Lys His Gly Met Leu Arg Asp Leu
        450                 455                 460

Asn Asn Ile Pro Pro
465

<210> SEQ ID NO 42
<211> LENGTH: 469
<212> TYPE: PRT
<213> ORGANISM: Artificial Sequence
<220> FEATURE:
<223> OTHER INFORMATION: synthetically generated variant

<400> SEQUENCE: 42

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Trp Gln Phe Leu Asp Pro Pro Asp
        115                 120                 125

Ser Tyr Asp Trp Leu Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

```
Leu Glu Glu Ile Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Gly Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 43
<211> LENGTH: 469
<212> TYPE: PRT
<213> ORGANISM: Artificial Sequence
<220> FEATURE:
<223> OTHER INFORMATION: synthetically generated variant

<400> SEQUENCE: 43

Met Ala Ala Asp Gln Gly Ile Phe Thr Asn Ser Val Thr Leu Ser Pro
  1               5                  10                  15

Val Glu Gly Ser Arg Thr Gly Gly Thr Leu Pro Arg Arg Ala Phe Arg
                20                  25                  30

Arg Ser Cys Asp Arg Cys His Ala Gln Lys Ile Lys Cys Thr Gly Asn
            35                  40                  45

Lys Glu Val Thr Gly Arg Ala Pro Cys Gln Arg Cys Gln Gln Ala Gly
        50                  55                  60

Leu Arg Cys Val Tyr Ser Glu Arg Arg Pro Lys Arg Lys Leu Arg Gln
65                  70                  75                  80

Ser Arg Val Ala Asp Leu Val Ser Ala Asp Pro Asp Pro Cys Leu His
                85                  90                  95
```

```
Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
            115                 120                 125

Ser Tyr Asp Trp Ser Trp Ile Ser Ile Gly Thr Asp Glu Ala Ile Asp
            130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
            210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
            275                 280                 285

Ser Gln Ile Arg Arg Thr Gln Asn Ser His Met Ser Pro Leu Glu Gly
            290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
            370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
450                 455                 460

Asn Asn Ile Pro Pro
465

<210> SEQ ID NO 44
<211> LENGTH: 469
<212> TYPE: PRT
<213> ORGANISM: Artificial Sequence
<220> FEATURE:
```

-continued

<223> OTHER INFORMATION: synthetically generated variant

<400> SEQUENCE: 44

```
Met Ala Ala Asp Gln Gly Ile Phe Thr Asn Ser Val Thr Leu Ser Pro
1               5                   10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
50                  55                  60

Leu Arg Cys Val Tyr Ser Glu Arg Arg Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Gly Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
370                 375                 380

Met Ser Gly Glu Pro Gly Glu Asp Ile Ala Arg Thr Gly Ala Thr Asn
385                 390                 395                 400
```

```
Ser Ala Arg Cys Glu Glu Gln Pro Thr Thr Pro Ala Ala Arg Val Leu
            405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
            450                 455                 460

Asn Asn Ile Pro Pro
465

<210> SEQ ID NO 45
<211> LENGTH: 469
<212> TYPE: PRT
<213> ORGANISM: Artificial Sequence
<220> FEATURE:
<223> OTHER INFORMATION: synthetically generated variant

<400> SEQUENCE: 45

Met Ala Ala Asp Gln Gly Ile Phe Thr Asn Ser Val Thr Leu Ser Pro
 1               5                  10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
            35                  40                  45

Lys Glu Val Thr Gly Arg Ala Pro Cys Gln Arg Cys Gln Gln Ala Gly
            50                  55                  60

Leu Arg Cys Val Tyr Ser Glu Arg Arg Pro Lys Arg Lys Leu Arg Gln
65                  70                  75                  80

Ser Arg Ala Ala Asp Leu Val Ser Ala Asp Pro Asp Pro Cys Leu His
            85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Gly Thr Asp Glu Ala Ile Asp
            130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
            165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
            210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
            245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
            275                 280                 285
```

-continued

```
Ser Gln Ile Arg Arg Thr Gln Asn Ser His Met Ser Pro Leu Glu Gly
    290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
        355                 360                 365
Ile Thr Leu Gly Val His Ser Ala Gln Gly Ile Ala Ala Ser Ile Ser
    370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
        435                 440                 445
Ile Phe Ser Leu Ala Arg Lys His Lys His Gly Met Leu Arg Asp Leu
    450                 455                 460
Asn Asn Ile Pro Pro
465
```

<210> SEQ ID NO 46
<211> LENGTH: 469
<212> TYPE: PRT
<213> ORGANISM: Artificial Sequence
<220> FEATURE:
<223> OTHER INFORMATION: synthetically generated variant

<400> SEQUENCE: 46

```
Met Ala Ala Asp Gln Gly Ile Phe Thr Asn Ser Val Thr Leu Ser Pro
1               5                   10                  15
Val Glu Gly Ser Arg Thr Gly Gly Thr Leu Pro Arg Arg Ala Phe Arg
            20                  25                  30
Arg Ser Cys Asp Arg Cys His Ala Gln Lys Ile Lys Cys Thr Gly Asn
        35                  40                  45
Lys Glu Val Thr Gly Arg Ala Pro Cys Gln Arg Cys Gln Gln Ala Gly
    50                  55                  60
Leu Arg Cys Val Tyr Ser Glu Arg Cys Pro Lys Arg Lys Leu Arg Gln
65                  70                  75                  80
Ser Arg Ala Ala Asp Leu Val Ser Ala Asp Pro Asp Pro Cys Leu His
                85                  90                  95
Met Ser Ser Pro Pro Val Pro Ser Gln Ser Leu Pro Leu Asp Val Ser
            100                 105                 110
Glu Ser His Ser Ser Asn Thr Ser Arg Gln Phe Leu Asp Pro Pro Asp
        115                 120                 125
Ser Tyr Asp Trp Ser Trp Thr Ser Ile Gly Thr Asp Glu Ala Ile Asp
    130                 135                 140
Thr Asp Cys Trp Gly Leu Ser Gln Tyr Asp Gly Gly Phe Ser Cys Gln
145                 150                 155                 160
Leu Glu Pro Thr Leu Pro Asp Leu Pro Ser Pro Phe Glu Ser Thr Val
                165                 170                 175
```

```
Glu Lys Ala Pro Leu Pro Pro Val Ser Ser Asp Ile Ala Arg Ala Ala
            180                 185                 190

Ser Ala Gln Arg Lys Leu Phe Asp Asp Leu Ser Ala Val Ser Gln Glu
            195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Ala Ala Ile Ser Glu Leu Leu Leu
            275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 47
<211> LENGTH: 469
<212> TYPE: PRT
<213> ORGANISM: Artificial Sequence
<220> FEATURE:
<223> OTHER INFORMATION: synthetically generated variant

<400> SEQUENCE: 47

Met Ala Ala Asp Gln Gly Ile Phe Thr Asn Ser Val Thr Leu Ser Pro
1               5                   10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
            35                  40                  45

Lys Glu Val Thr Gly Arg Ala Pro Cys Gln Arg Cys Gln Gln Ala Gly
    50                  55                  60
```

```
Leu Arg Cys Val Tyr Ser Glu Arg Pro Lys Arg Lys Leu Arg Gln
 65                  70                  75                  80

Ser Arg Ala Ala Asp Leu Val Ser Ala Asp Pro Asp Pro Cys Leu His
             85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Gly Thr Asp Glu Ala Ile Asp
        130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
                180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Ala
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
        370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
450                 455                 460

Asn Ser Ile Pro Pro
465
```

```
<210> SEQ ID NO 48
<211> LENGTH: 469
<212> TYPE: PRT
<213> ORGANISM: Artificial Sequence
<220> FEATURE:
<223> OTHER INFORMATION: synthetically generated variant

<400> SEQUENCE: 48

Met Ala Ala Asp Gln Gly Ile Phe Thr Asn Ser Val Thr Leu Ser Pro
 1               5                  10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
 50                  55                  60

Leu Arg Cys Val Tyr Ser Glu Arg Arg Pro Lys Arg Lys Leu Arg Gln
 65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Ala
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
```

```
              370                 375                 380
Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
                435                 440                 445

Ile Phe Ser Leu Ala Arg Lys His Lys His Gly Met Leu Arg Asp Leu
                450                 455                 460

Asn Ser Ile Pro Pro
465

<210> SEQ ID NO 49
<211> LENGTH: 469
<212> TYPE: PRT
<213> ORGANISM: Artificial Sequence
<220> FEATURE:
<223> OTHER INFORMATION: synthetically generated variant

<400> SEQUENCE: 49

Met Ala Ala Asp Gln Gly Ile Phe Thr Asn Ser Val Thr Leu Ser Pro
  1               5                  10                  15

Val Glu Gly Ser Arg Thr Gly Thr Leu Pro Arg Arg Ala Phe Arg
                 20                  25                  30

Arg Ser Cys Asp Arg Cys His Ala Gln Lys Ile Lys Cys Thr Gly Asn
                 35                  40                  45

Lys Glu Val Thr Gly Arg Ala Pro Cys Gln Arg Cys Gln Gln Ala Gly
 50                  55                  60

Leu Arg Cys Val Tyr Ser Glu Arg Arg Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
                100                 105                 110

Glu Ser His Ser Ser Asn Thr Ser Arg Gln Phe Leu Asp Pro Pro Asp
                115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
                180                 185                 190

Ser Ala Gln Arg Glu Leu Phe Asp Asp Leu Ser Ala Val Ser Gln Glu
                195                 200                 205

Leu Glu Glu Ile Leu Leu Ala Val Thr Val Glu Trp Pro Lys Gln Glu
                210                 215                 220

Ile Trp Thr His Pro Ile Gly Met Phe Asn Ala Ser Arg Arg Leu
225                 230                 235                 240

Leu Thr Val Leu Arg Gln Gln Ala Gln Ala Asp Cys His Gln Gly Ala
                245                 250                 255

Leu Asp Glu Cys Leu Arg Thr Lys Asn Leu Phe Thr Ala Val His Cys
```

```
                   260                 265                 270
Tyr Ile Leu Asn Val Arg Ile Leu Thr Ala Ile Ser Glu Leu Leu
            275                 280                 285
Ser Gln Ile Arg Arg Thr Gln Asn Ser His Met Ser Pro Leu Glu Gly
        290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
            355                 360                 365
Ile Thr Leu Gly Val His Ser Ala Gln Gly Ile Ala Ala Ser Ile Ser
        370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
        435                 440                 445
Ile Phe Ser Leu Ala Arg Lys His Lys His Gly Met Leu Arg Asp Leu
    450                 455                 460
Asn Ser Ile Pro Pro
465

<210> SEQ ID NO 50
<211> LENGTH: 469
<212> TYPE: PRT
<213> ORGANISM: Artificial Sequence
<220> FEATURE:
<223> OTHER INFORMATION: synthetically generated variant

<400> SEQUENCE: 50

Met Ala Ala Asp Gln Gly Ile Phe Thr Asn Ser Val Thr Leu Ser Pro
  1               5                  10                  15
Val Glu Gly Ser Arg Thr Gly Gly Thr Leu Pro Arg Arg Ala Phe Arg
             20                  25                  30
Arg Ser Cys Asp Arg Cys His Ala Gln Lys Ile Lys Cys Thr Gly Asn
         35                  40                  45
Lys Glu Val Thr Gly Arg Ala Pro Cys Gln Arg Cys Gln Gln Ala Gly
     50                  55                  60
Leu Arg Cys Val Tyr Ser Glu Arg Arg Pro Lys Arg Lys Leu Arg Gln
 65                  70                  75                  80
Ser Arg Ala Ala Asp Leu Val Ser Ala Asp Pro Asp Pro Cys Leu His
                 85                  90                  95
Met Ser Ser Pro Pro Val Pro Ser Gln Ser Leu Pro Leu Asp Val Ser
            100                 105                 110
Glu Ser His Ser Ser Asn Thr Ser Arg Gln Phe Leu Asp Pro Pro Asp
        115                 120                 125
Ser Tyr Asp Trp Ser Trp Thr Ser Ile Gly Thr Asp Glu Ala Ile Asp
    130                 135                 140
Thr Asp Cys Trp Gly Leu Ser Gln Cys Asp Gly Gly Phe Ser Cys Gln
```

```
                145                 150                 155                 160
Leu Glu Pro Thr Leu Pro Asp Leu Pro Ser Pro Phe Glu Ser Thr Val
                    165                 170                 175

Glu Lys Ala Pro Leu Pro Pro Val Ser Ser Asp Ile Ala Arg Ala Ala
                180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
        210                 215                 220

Ile Trp Thr His Pro Ile Gly Met Phe Asn Ala Ser Arg Arg Leu
225                 230                 235                 240

Leu Thr Val Leu Arg Gln Gln Ala Gln Ala Asp Cys His Gln Gly Ala
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Ser Ile Pro Pro
465

<210> SEQ ID NO 51
<211> LENGTH: 469
<212> TYPE: PRT
<213> ORGANISM: Artificial Sequence
<220> FEATURE:
<223> OTHER INFORMATION: synthetically generated variant

<400> SEQUENCE: 51

Met Ala Ala Asp Gln Gly Ile Phe Met Asn Ser Val Thr Leu Ser Ala
 1               5                  10                  15

Val Glu Gly Ser Arg Thr Ser Gly Thr Leu Pro Arg Arg Ala Phe Arg
                20                  25                  30

Arg Ser Cys Asp Arg Cys His Ala Lys Lys Ile Lys Cys Thr Gly Asn
```

```
                35                  40                  45
Lys Glu Val Thr Gly Arg Ala Pro Cys Gln Arg Cys Gln Gln Ala Gly
 50                  55                  60
Leu Arg Cys Val Tyr Ser Glu Arg Cys Pro Lys Arg Lys Leu Arg Gln
 65                  70                  75                  80
Ser Arg Ala Ala Asp Leu Val Ser Ala Asp Pro Asp Pro Cys Leu His
                 85                  90                  95
Met Ser Ser Pro Pro Val Pro Ser Gln Ser Leu Pro Leu Asp Val Ser
                100                 105                 110
Glu Ser His Ser Ser Asn Thr Ser Arg Gln Phe Leu Asp Pro Pro Asp
                115                 120                 125
Ser Tyr Asp Trp Ser Trp Thr Ser Ile Gly Thr Asp Glu Ala Ile Asp
130                 135                 140
Thr Asp Cys Trp Gly Leu Ser Gln Cys Asp Gly Phe Ser Cys Gln
145                 150                 155                 160
Leu Glu Pro Thr Leu Pro Asp Leu Pro Ser Pro Phe Glu Ser Thr Val
                165                 170                 175
Glu Lys Ala Pro Leu Pro Pro Val Ser Ser Asp Ile Ala Arg Ala Ala
                180                 185                 190
Ser Ala Gln Arg Glu Leu Phe Asp Asp Leu Ser Ala Val Ser Gln Glu
                195                 200                 205
Leu Glu Glu Ile Leu Leu Ala Val Thr Val Glu Trp Pro Lys Gln Glu
210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Thr
                245                 250                 255
Leu Asp Glu Cys Leu Arg Thr Lys Asn Leu Phe Thr Ala Val His Cys
                260                 265                 270
Tyr Ile Leu Asn Val Arg Ile Leu Thr Ala Ile Ser Glu Leu Leu Leu
                275                 280                 285
Ser Gln Ile Arg Arg Thr Gln Asn Ser His Met Ser Pro Leu Glu Gly
                290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
                340                 345                 350
Ala Cys Thr Thr Leu His Val Gly Val Glu Leu Leu Arg Glu Asn Glu
                355                 360                 365
Ile Thr Leu Gly Val His Ser Ala Gln Gly Ile Ala Ala Ser Ile Ser
                370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
                420                 425                 430
Gly Ser Arg Gly Arg Thr Ile Ala Ala Leu Arg Arg Cys Tyr Glu Asp
                435                 440                 445
Ile Phe Ser Leu Ala Arg Lys His Lys His Gly Met Leu Arg Asp Leu
                450                 455                 460
```

Asn Asn Ile Pro Pro
465

<210> SEQ ID NO 52
<211> LENGTH: 469
<212> TYPE: PRT
<213> ORGANISM: Artificial Sequence
<220> FEATURE:
<223> OTHER INFORMATION: synthetically generated variant

<400> SEQUENCE: 52

Met Ala Ala Asp Gln Gly Ile Phe Thr Asn Ser Val Thr Leu Ser Pro
1               5                   10                  15

Val Glu Gly Ser His Thr Gly Gly Thr Leu Pro Arg Arg Ala Phe Arg
            20                  25                  30

Arg Ala Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
50                  55                  60

Leu Arg Cys Val Tyr Ser Glu Arg Cys Pro Lys Arg Lys Leu Arg His
65                  70                  75                  80

Ser Arg Ala Ser Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Asp Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

```
Ala Cys Thr Thr Leu His Val Gly Val Gln Leu Leu Arg Glu Asn Glu
            355                 360                 365

Ile Thr Leu Gly Val Asp Ser Ala Gln Gly Ile Ala Ala Ser Ile Ser
        370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Thr Val Leu Arg Arg Ser Tyr Glu Asp
            435                 440                 445

Ile Phe Ser Leu Ala Arg Lys His Lys His Gly Met Leu Arg Asp Leu
        450                 455                 460

Asn Asn Ile Pro Ser
465

<210> SEQ ID NO 53
<211> LENGTH: 469
<212> TYPE: PRT
<213> ORGANISM: Artificial Sequence
<220> FEATURE:
<223> OTHER INFORMATION: synthetically generated variant

<400> SEQUENCE: 53

Met Ala Ala Asp Gln Gly Ile Phe Thr Asn Ser Val Thr Leu Ser Pro
 1                5                 10                 15

Val Glu Gly Ser Arg Thr Gly Gly Thr Leu Pro Arg Arg Ala Leu Arg
            20                  25                  30

Arg Ser Cys Asp Arg Cys His Ala Gln Lys Ile Lys Cys Thr Gly Asn
         35                 40                  45

Lys Glu Val Thr Gly Arg Ala Pro Cys Gln Arg Cys Gln Gln Ala Gly
 50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240
```

-continued

```
Leu Thr Val Leu Arg Gln Gln Ala Gln Ala Asp Cys His Gln Gly Thr
            245                 250                 255

Leu Asp Glu Cys Leu Arg Thr Lys Asn Leu Phe Thr Ala Val His Cys
        260                 265                 270

Tyr Ile Leu Asn Val Arg Ile Leu Thr Ala Ile Ser Glu Leu Leu Leu
    275                 280                 285

Ser Gln Ile Arg Arg Thr Gln Asn Ser His Met Ser Pro Leu Glu Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Gln Pro Ile Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 54
<211> LENGTH: 469
<212> TYPE: PRT
<213> ORGANISM: Artificial Sequence
<220> FEATURE:
<223> OTHER INFORMATION: synthetically generated variant

<400> SEQUENCE: 54

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Leu Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Ile Ser Ser Pro Pro Val Pro Ser Gln Ser Leu Pro Leu Asp Val Ser
            100                 105                 110

Asp Ser His Ser Ser Asn Thr Ser Arg Gln Phe Leu Asp Pro Pro Asp
        115                 120                 125
```

```
Ser Tyr Asp Trp Ser Trp Thr Ser Ile Gly Thr Asp Glu Ala Ile Asp
    130                 135                 140

Thr Asn Cys Trp Gly Leu Ser Gln Cys Asp Gly Gly Phe Ser Cys Gln
145                 150                 155                 160

Leu Glu Ser Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Ile Glu
        355                 360                 365

Ile Thr Leu Gly Val His Ser Ala Gln Gly Ile Ala Ala Ser Ile Ser
    370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys Tyr Gly Met Leu Arg Asp Leu
    450                 455                 460

Asn Asn Ile Pro Pro
465

<210> SEQ ID NO 55
<211> LENGTH: 470
<212> TYPE: PRT
<213> ORGANISM: Artificial Sequence
<220> FEATURE:
<223> OTHER INFORMATION: synthetically generated variant

<400> SEQUENCE: 55

Met Ala Ala Asp Gln Gly Ile Phe Thr Asn Ser Val Thr Leu Ser Pro
1               5                   10                  15
```

```
Val Glu Gly Ser Arg Thr Gly Gly Thr Leu Pro Arg Arg Ala Phe Arg
            20                  25                  30

Arg Ser Cys Asp Arg Cys His Ala Gln Lys Val Lys Cys Thr Gly Asn
        35                  40                  45

Lys Glu Val Thr Gly Arg Ala Pro Cys Gln Arg Cys Gln Gln Ala Gly
        50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
        130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
        210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Leu Asn Ser His Met Ser Pro Leu Glu Gly
        290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
        370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430
```

```
Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro Cys
465             470

<210> SEQ ID NO 56
<211> LENGTH: 469
<212> TYPE: PRT
<213> ORGANISM: Artificial Sequence
<220> FEATURE:
<223> OTHER INFORMATION: synthetically generated variant

<400> SEQUENCE: 56

Met Ala Ala Asp Gln Gly Ile Phe Thr Asn Ser Val Thr Leu Ser Pro
  1               5                  10                  15

Val Glu Gly Ser Arg Thr Gly Gly Thr Leu Pro Arg Arg Ala Leu Arg
             20                  25                  30

Arg Ser Cys Asp Arg Cys His Ala Gln Lys Ile Lys Cys Thr Gly Asn
         35                  40                  45

Lys Glu Val Thr Gly Arg Ala Pro Cys Gln Arg Cys Gln Gln Ala Gly
 50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Ser Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Arg Asp Gly Gly Phe Ser Ser Gln
145                 150                 155                 160

Leu Lys Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Leu Thr Gln Asn Ser His Met Ser Pro Leu Glu Gly
    290                 295                 300

Ser Arg Ser Gln Ser Pro Asn Arg Asp Asp Thr Ser Ser Ser Ser Gly
305                 310                 315                 320
```

-continued

```
His Ser Ser Val Asp Thr Ile Pro Phe Phe Ser Glu Asn Leu Pro Ile
            325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
            370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
            405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
450                 455                 460

Asn Asn Ile Pro Pro
465

<210> SEQ ID NO 57
<211> LENGTH: 469
<212> TYPE: PRT
<213> ORGANISM: Artificial Sequence
<220> FEATURE:
<223> OTHER INFORMATION: synthetically generated variant

<400> SEQUENCE: 57

Met Ala Ala Asp Gln Gly Ile Phe Thr Asn Ser Val Thr Ile Ser Pro
1               5                   10                  15

Val Val Gly Ser Arg Thr Gly Gly Thr Leu Pro Arg Arg Ala Phe Arg
            20                  25                  30

Arg Ser Cys Asp Arg Cys His Ala Gln Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
            85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Cys Thr Asp Glu Ala Ile Asp
            130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
            165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205
```

```
Leu Glu Glu Ile Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
    290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Gly Leu Phe Ser Tyr Val Asp Pro Leu Thr His Ala Leu Phe Ser
            340                 345                 350

Ala Cys Thr Thr Leu His Val Gly Leu Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Ser Gly Glu Asp Ile Ala Arg Thr Gly Ala Thr Ser
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 58
<211> LENGTH: 469
<212> TYPE: PRT
<213> ORGANISM: Artificial Sequence
<220> FEATURE:
<223> OTHER INFORMATION: synthetically generated variant

<400> SEQUENCE: 58

Met Ala Ala Asp Gln Gly Ile Phe Thr Asn Ser Val Thr Leu Ser Pro
1               5                   10                  15

Val Glu Gly Ser Arg Thr Gly Gly Thr Leu Pro Arg Arg Ala Phe Arg
            20                  25                  30

Arg Ser Cys Asp Arg Cys His Ala Arg Lys Ile Lys Cys Thr Gly Asn
        35                  40                  45

Lys Glu Val Thr Gly Arg Ala Pro Cys Gln Arg Cys Gln Gln Ala Gly
    50                  55                  60

Leu Arg Cys Val Tyr Ser Glu Arg Cys Pro Lys Arg Lys Leu Arg Gln
65                  70                  75                  80

Ser Arg Ala Ala Asp Leu Val Ser Ala Asp Pro Asp Pro Cys Leu His
                85                  90                  95
```

```
Met Ser Ser Pro Pro Val Pro Ser Gln Ser Leu Pro Leu Asp Val Ser
              100                 105                 110

Glu Ser His Ser Ser Asn Thr Ser Arg Gln Phe Leu Asp Pro Pro Asp
              115                 120                 125

Ser Tyr Asp Trp Ser Trp Thr Ser Ile Gly Thr Asp Glu Ala Ile Asp
        130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Tyr Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Thr Gln Asn Ser His Met Ser Pro Leu Glu Gly
290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
370                 375                 380

Met Ser Gly Glu Pro Gly Glu Asp Ile Ala Arg Thr Gly Ala Thr Asn
385                 390                 395                 400

Ser Thr Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
450                 455                 460

Asn Asn Ile Pro Pro
465

<210> SEQ ID NO 59
<211> LENGTH: 469
<212> TYPE: PRT
<213> ORGANISM: Artificial Sequence
<220> FEATURE:
<223> OTHER INFORMATION: synthetically generated variant
```

<400> SEQUENCE: 59

| | | | | | | | | | | | | | | |
|---|---|---|---|---|---|---|---|---|---|---|---|---|---|---|
|Met|Ala|Ala|Asp|Gln|Gly|Ile|Phe|Thr|Asn|Ser|Val|Thr|Leu|Ser|Pro|
|1| | | |5| | | |10| | | |15| | |
|Val|Glu|Gly|Ser|Arg|Thr|Gly|Gly|Thr|Leu|Pro|Arg|Arg|Ala|Leu|Arg|
| | | |20| | | |25| | | |30| | | | |
|Arg|Ser|Cys|Asp|Arg|Cys|His|Ala|Gln|Lys|Ile|Lys|Cys|Thr|Gly|Asn|
| | |35| | | | |40| | | |45| | | | |
|Lys|Glu|Val|Ile|Gly|Arg|Ala|Pro|Cys|Gln|Arg|Cys|Gln|Gln|Ala|Gly|
| |50| | | | |55| | | |60| | | | | |
|Leu|Arg|Cys|Val|Tyr|Ser|Glu|Arg|Cys|Pro|Lys|Arg|Lys|Leu|Arg|Gln|
|65| | | |70| | | |75| | | | | | |80|
|Ser|Arg|Ala|Ala|Asp|Leu|Val|Ser|Ala|Asp|Pro|Asp|Pro|Cys|Leu|His|
| | | |85| | | | |90| | | |95| | | |
|Met|Ser|Ser|Pro|Gln|Val|Pro|Ser|Gln|Ser|Leu|Ser|Leu|Asp|Ile|Ser|
| | |100| | | | |105| | | |110| | | | |
|Glu|Ser|His|Ser|Ser|Asn|Thr|Ser|Arg|Gln|Phe|Leu|Asp|Pro|Pro|Asp|
| | |115| | | | |120| | | |125| | | | |
|Ser|Tyr|Asp|Trp|Ser|Trp|Thr|Ser|Ile|Gly|Thr|Asp|Glu|Ala|Ile|Asp|
| |130| | | | |135| | | |140| | | | | |
|Thr|Asp|Cys|Trp|Gly|Leu|Ser|Gln|Cys|Asp|Gly|Gly|Phe|Ser|Cys|Gln|
|145| | | |150| | | |155| | | |160| | | |
|Leu|Glu|Pro|Thr|Leu|Pro|Asp|Leu|Pro|Ser|Pro|Phe|Glu|Ser|Thr|Val|
| | | |165| | | |170| | | |175| | | | |
|Glu|Lys|Ala|Pro|Leu|Pro|Pro|Val|Ser|Ser|Asp|Ile|Ala|Arg|Ala|Ala|
| | |180| | | | |185| | | |190| | | | |
|Ser|Ala|Gln|Arg|Glu|Leu|Phe|Asp|Asp|Leu|Ser|Ala|Val|Ser|Gln|Glu|
| |195| | | | |200| | | |205| | | | | |
|Leu|Glu|Glu|Ile|Leu|Leu|Ala|Val|Thr|Val|Glu|Trp|Pro|Lys|Gln|Glu|
|210| | | |215| | | |220| | | | | | | |
|Ile|Trp|Thr|His|Pro|Ile|Gly|Met|Phe|Phe|Asn|Ala|Ser|Arg|Arg|Leu|
|225| | | |230| | | |235| | | |240| | | |
|Leu|Thr|Val|Leu|Arg|Gln|Gln|Ala|Gln|Ala|Asp|Cys|His|Gln|Gly|Thr|
| | | |245| | | |250| | | |255| | | | |
|Leu|Asp|Glu|Cys|Leu|Arg|Thr|Lys|Asn|Leu|Phe|Thr|Ala|Val|His|Cys|
| | |260| | | | |265| | | |270| | | | |
|Tyr|Ile|Leu|Asn|Val|Arg|Ile|Leu|Thr|Ala|Ile|Ser|Glu|Leu|Leu|Leu|
| |275| | | | |280| | | |285| | | | | |
|Ser|Gln|Ile|Arg|Arg|Thr|Gln|Asn|Ser|His|Met|Ser|Pro|Leu|Glu|Gly|
| |290| | | | |295| | | |300| | | | | |
|Ser|Arg|Ser|Gln|Ser|Pro|Ser|Arg|Asp|Asp|Thr|Ser|Ser|Ser|Ser|Gly|
|305| | | |310| | | |315| | | | | | |320|
|His|Ser|Ser|Val|Asp|Thr|Ile|Pro|Phe|Phe|Ser|Glu|Asn|Leu|Pro|Ile|
| | | |325| | | |330| | | |335| | | | |
|Gly|Glu|Leu|Phe|Ser|Tyr|Val|Asp|Pro|Leu|Thr|His|Ala|Leu|Phe|Ser|
| | |340| | | | |345| | | |350| | | | |
|Ala|Cys|Thr|Thr|Leu|His|Val|Gly|Val|Gln|Leu|Leu|Arg|Glu|Asn|Glu|
| | |355| | | | |360| | | |365| | | | |
|Ile|Thr|Leu|Gly|Val|His|Ser|Ala|Gln|Gly|Ile|Ala|Ala|Ser|Ile|Ser|
| |370| | | | |375| | | |380| | | | | |
|Met|Ser|Gly|Glu|Pro|Gly|Glu|Asp|Ile|Ala|Arg|Thr|Gly|Ala|Thr|Asn|
|385| | | |390| | | |395| | | |400| | | |
|Ser|Ala|Arg|Cys|Glu|Glu|Gln|Pro|Thr|Thr|Pro|Ala|Ala|Arg|Val|Leu|

```
                    405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
            435                 440                 445
Ile Phe Ser Leu Ala Arg Lys His Lys His Gly Met Leu Arg Asp Leu
            450                 455                 460
Asn Asn Ile Pro Pro
465

<210> SEQ ID NO 60
<211> LENGTH: 469
<212> TYPE: PRT
<213> ORGANISM: Artificial Sequence
<220> FEATURE:
<223> OTHER INFORMATION: synthetically generated variant

<400> SEQUENCE: 60

Met Ala Ala Asp Gln Gly Ile Phe Thr Asn Ser Val Thr Leu Ser Pro
1               5                   10                  15
Val Glu Gly Ser Arg Thr Gly Gly Thr Leu Pro Arg Arg Ala Phe Arg
            20                  25                  30
Arg Ser Cys Asp Arg Cys His Ala Gln Lys Ile Lys Cys Thr Gly Asn
        35                  40                  45
Lys Glu Val Thr Gly Arg Ala Pro Cys Gln Arg Cys Gln Gln Ala Gly
    50                  55                  60
Leu Arg Cys Val Tyr Ser Glu Arg Cys Pro Lys Arg Lys Leu Arg Gln
65                  70                  75                  80
Ser Arg Ala Ala Asn Leu Val Ser Ala Asp Pro Asp Pro Cys Leu His
                85                  90                  95
Met Ser Ser Pro Pro Val Pro Ser Gln Ser Leu Pro Leu Asp Val Ser
            100                 105                 110
Glu Ser His Ser Ser Asn Thr Ser Arg Gln Phe Leu Asp Pro Pro Asp
        115                 120                 125
Ser Tyr Asp Trp Ser Trp Thr Ser Ile Gly Thr Asp Glu Ala Phe Asp
    130                 135                 140
Thr Asp Cys Trp Gly Leu Ser Gln Cys Asp Gly Gly Phe Ser Cys Gln
145                 150                 155                 160
Leu Glu Pro Thr Leu Pro Asp Leu Pro Ser Pro Phe Glu Ser Thr Val
                165                 170                 175
Glu Lys Ala Pro Leu Pro Pro Val Ser Ser Asp Ile Ala Arg Ala Ala
            180                 185                 190
Ser Ala Gln Arg Glu Leu Phe Asp Asp Leu Ser Ala Val Ser Gln Glu
        195                 200                 205
Leu Glu Glu Ile Leu Leu Ala Val Thr Val Glu Trp Pro Lys Gln Glu
    210                 215                 220
Ile Trp Thr His Pro Ile Gly Ile Phe Phe Asn Ala Ser Arg Arg Leu
225                 230                 235                 240
Leu Thr Val Leu Arg Gln Gln Ala Gln Ala Asp Cys His Gln Gly Thr
                245                 250                 255
Leu Asp Glu Cys Leu Arg Thr Lys Asn Leu Phe Thr Ala Val His Cys
            260                 265                 270
Tyr Ile Leu Asn Val Arg Ile Leu Thr Ala Ile Ser Glu Leu Leu Leu
        275                 280                 285
Ser Gln Ile Arg Arg Thr Gln Asn Ser His Met Ser Pro Leu Glu Gly
```

```
                    290                 295                 300
Ser Arg Ser Gln Ser Pro Ser Arg Asp Asp Ile Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Tyr Ile Ser
    370                 375                 380

Lys Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
                420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
        450                 455                 460

Asn Asn Ile Pro Pro
465

<210> SEQ ID NO 61
<211> LENGTH: 469
<212> TYPE: PRT
<213> ORGANISM: Artificial Sequence
<220> FEATURE:
<223> OTHER INFORMATION: synthetically generated variant

<400> SEQUENCE: 61

Met Ala Ala Asp Gln Gly Ile Phe Thr Asn Ser Val Thr Leu Ser Pro
1               5                   10                  15

Val Glu Gly Ser Arg Thr Gly Thr Leu Pro Arg Arg Ala Phe Arg
            20                  25                  30

Arg Ser Cys Asp Arg Cys His Ala Gln Lys Ile Lys Cys Ile Gly Asn
            35                  40                  45

Lys Glu Val Thr Gly Arg Ala Pro Cys Gln Arg Cys Gln Arg Ala Gly
50                  55                  60

Leu Arg Cys Val Tyr Ser Glu Arg Cys Pro Lys Arg Arg Leu Arg Gln
65                  70                  75                  80

Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
```

-continued

```
                180                 185                 190
Ser Ala Gln Arg Glu Leu Phe Asp Asp Leu Ser Ala Val Ser Gln Glu
            195                 200                 205
Leu Glu Glu Ile Leu Leu Ala Val Thr Val Glu Trp Pro Lys Gln Glu
        210                 215                 220
Ile Trp Thr His Pro Ile Gly Met Phe Phe Asn Ala Ser Arg Arg Leu
225                 230                 235                 240
Leu Thr Val Leu Arg Gln Ala Gln Ala Asp Cys His Gln Gly Thr
                245                 250                 255
Leu Asp Glu Cys Leu Arg Thr Lys Asn Leu Phe Thr Ala Val His Cys
            260                 265                 270
Tyr Ile Leu Asn Val Arg Ile Leu Thr Ala Ile Ser Glu Leu Leu Leu
        275                 280                 285
Ser Gln Ile Arg Arg Thr Gln Asn Ser His Met Ser Pro Leu Glu Gly
        290                 295                 300
Ser Arg Ser Gln Ser Pro Ser Arg Asp Asp Thr Ser Ser Ser Ser Gly
305                 310                 315                 320
His Ser Cys Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Tyr Glu
        355                 360                 365
Ile Thr Leu Gly Ile His Ser Ala Gln Gly Ile Ala Ala Ser Ile Ser
        370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
        435                 440                 445
Ile Phe Ser Leu Ala Arg Lys His Lys His Gly Met Leu Arg Asp Leu
        450                 455                 460
Asn Asn Ile Pro Pro
465

<210> SEQ ID NO 62
<211> LENGTH: 469
<212> TYPE: PRT
<213> ORGANISM: Artificial Sequence
<220> FEATURE:
<223> OTHER INFORMATION: synthetically generated variant

<400> SEQUENCE: 62

Met Ala Ala Asp Gln Gly Ile Phe Thr Asn Ser Val Thr Leu Ser Pro
1               5                   10                  15
Val Glu Gly Ser Arg Thr Gly Gly Thr Leu Pro Arg Arg Ala Phe Arg
            20                  25                  30
Arg Ser Cys Asp Arg Cys His Ala Arg Lys Ile Lys Cys Thr Gly Asn
        35                  40                  45
Lys Glu Val Thr Gly Arg Ala Pro Cys Gln Arg Cys Gln Gln Ala Gly
    50                  55                  60
Leu Arg Cys Val Tyr Ser Glu Arg Cys Pro Lys Arg Lys Leu Arg Gln
```

```
            65                  70                  75                  80
Ser Arg Ala Ala Asp Leu Val Ser Ala Asp Pro Asp Pro Cys Leu His
                85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
        115                 120                 125

Ser Tyr Asp Trp Ser Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
        195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
        275                 280                 285

Ser Gln Ile Arg Arg Ile Gln Asn Ser His Met Ser Pro Leu Glu Gly
    290                 295                 300

Ser Arg Ser Gln Ser Leu Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Asp Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
        355                 360                 365

Ile Thr Leu Gly Val His Ser Ala Gln Gly Ile Ala Ala Ser Ile Ser
    370                 375                 380

Met Ser Gly Glu Leu Gly Glu Asp Ile Val Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Ser Arg Thr Ile Ala Ala Leu Arg Arg Cys Tyr Glu Asp
        435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 63
```

<211> LENGTH: 469
<212> TYPE: PRT
<213> ORGANISM: Artificial Sequence
<220> FEATURE:
<223> OTHER INFORMATION: synthetically generated variant

<400> SEQUENCE: 63

```
Met Ala Ala Asp Gln Gly Ile Phe Thr Asn Ser Val Thr Leu Ser Pro
  1               5                  10                  15
Val Glu Gly Ser Arg Thr Gly Gly Thr Leu Pro Arg Arg Ala Phe Arg
             20                  25                  30
Arg Ser Cys Asp Arg Cys His Ala Gln Lys Ile Lys Cys Thr Gly Asn
         35                  40                  45
Lys Glu Val Asn Gly Arg Ala Pro Cys Gln Arg Cys Gln Gln Ala Gly
 50                  55                  60
Leu Arg Cys Val Tyr Ser Glu Arg Cys Pro Lys Arg Lys Leu Arg Gln
 65                  70                  75                  80
Ser Arg Ala Ala Asp Leu Val Ser Ala Asp Pro Asp Pro Cys Leu His
                 85                  90                  95
Met Ser Ser Pro Pro Val Pro Ser Gln Ser Leu Pro Leu Asp Ile Ser
            100                 105                 110
Glu Ser His Ser Ser Asn Thr Ser Arg Gln Phe Leu Asp Pro Pro Asp
        115                 120                 125
Ser Tyr Asp Trp Ser Trp Thr Ser Ile Gly Ile Asp Glu Ala Ile Asp
    130                 135                 140
Thr Asp Cys Trp Gly Leu Ser Gln Cys Asp Gly Gly Phe Ser Cys Gln
145                 150                 155                 160
Leu Glu Pro Thr Leu Pro Asp Leu Pro Ser Pro Phe Glu Ser Thr Val
                165                 170                 175
Glu Lys Ala Pro Leu Pro Pro Ile Ser Ser Asp Ile Ala Arg Ala Ala
            180                 185                 190
Ser Ala Gln Arg Glu Leu Phe Asp Asp Leu Ser Ala Val Ser Gln Glu
        195                 200                 205
Leu Glu Glu Ile Leu Leu Ala Val Thr Val Glu Trp Pro Lys Gln Glu
    210                 215                 220
Ile Trp Thr His Pro Ile Gly Met Phe Phe Asn Ala Ser Arg Arg Leu
225                 230                 235                 240
Leu Thr Val Leu Arg Gln Gln Ala Gln Ala Asp Cys His Gln Gly Thr
                245                 250                 255
Leu Asp Glu Cys Leu Arg Thr Lys Asn Leu Phe Thr Ala Val His Cys
            260                 265                 270
Tyr Ile Leu Asn Val Arg Ile Leu Ala Ala Ile Ser Glu Leu Leu Leu
        275                 280                 285
Ser Gln Ile Arg Arg Thr Gln Asn Ser His Met Ser Pro Leu Glu Gly
    290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
        355                 360                 365
Ile Thr Leu Gly Val His Ser Ala Gln Gly Ile Ala Ala Ser Ile Ser
    370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Ala Lys Ser Ala
            420                 425                 430
Gly Ser Arg Gly Arg Thr Ile Ala Ala Leu Arg Arg Cys Tyr Glu Asp
        435                 440                 445
Ile Phe Ser Leu Ala Arg Lys His Lys His Gly Met Leu Arg Asp Leu
    450                 455                 460
Asn Asn Ile Pro Pro
465
```

<210> SEQ ID NO 64
<211> LENGTH: 469
<212> TYPE: PRT
<213> ORGANISM: Artificial Sequence
<220> FEATURE:
<223> OTHER INFORMATION: synthetically generated variant

<400> SEQUENCE: 64

-continued

```
Met Ala Ala Glu Gln Gly Ile Phe Thr Asn Ser Val Thr Leu Ser Pro
 1               5                  10                  15
Val Glu Gly Ser Arg Thr Gly Gly Thr Leu Pro Arg Arg Ala Phe Arg
                20                  25                  30
Arg Ser Cys Asp Arg Cys His Ala Arg Lys Ile Lys Cys Thr Gly Asn
            35                  40                  45
Lys Glu Val Thr Gly Arg Ala Pro Cys Gln Arg Cys Gln Gln Ala Gly
 50                  55                  60
Leu Arg Cys Val Tyr Ser Glu Arg Cys Pro Lys Arg Lys Leu Arg Gln
 65                  70                  75                  80
Ser Arg Ala Ala Asp Leu Ile Ser Ala Asp Pro Asp Pro Cys Leu His
                85                  90                  95
Met Ser Ser Pro Pro Val Pro Ser Gln Ser Leu Pro Leu Glu Val Ser
               100                 105                 110
Glu Ser His Ser Ser Asn Thr Ser Arg Gln Phe Leu Asp Pro Pro Asp
               115                 120                 125
Ser Tyr Asp Trp Ser Trp Thr Ser Ile Gly Thr Asp Lys Ala Ile Asp
       130                 135                 140
Thr Asp Cys Trp Gly Leu Ser Gln Cys Asp Gly Gly Phe Ser Cys Gln
145                 150                 155                 160
Leu Glu Pro Thr Leu Pro Asp Leu Pro Ser Pro Phe Glu Ser Thr Val
               165                 170                 175
Glu Lys Ala Pro Leu Pro Pro Val Ser Ser Asp Ile Thr Arg Ala Ala
               180                 185                 190
Ser Ala Gln Arg Glu Leu Phe Asp Asp Leu Ser Ala Val Ser Gln Glu
       195                 200                 205
Leu Glu Glu Ile Leu Leu Ala Val Thr Val Glu Trp Pro Lys Gln Glu
       210                 215                 220
Ile Trp Thr His Pro Ile Gly Met Phe Phe Asn Ala Ser Arg Arg Leu
225                 230                 235                 240
Leu Thr Val Leu Arg Gln Ala Gln Ala Asp Cys His Gln Gly Thr
               245                 250                 255
Leu Asp Glu Cys Leu Arg Thr Lys Asn Leu Phe Thr Ala Val His Cys
               260                 265                 270
Tyr Ile Leu Asp Val Arg Ile Leu Thr Ala Ile Ser Glu Leu Leu Leu
       275                 280                 285
Ser Gln Ile Arg Arg Thr Gln Asn Ser His Met Ser Pro Leu Glu Gly
       290                 295                 300
Ser Arg Ser Gln Ser Pro Ser Arg Asp Asp Thr Ser Ser Ser Ser Gly
305                 310                 315                 320
His Ser Ser Val Asp Thr Ile Pro Phe Phe Ser Glu Asn Leu Pro Ile
               325                 330                 335
Gly Glu Leu Phe Ser Tyr Val Asp Pro Leu Arg His Ala Leu Phe Ser
               340                 345                 350
Ala Cys Thr Thr Leu His Val Gly Val Gln Leu Leu Arg Glu Ile Glu
               355                 360                 365
Ile Thr Leu Gly Val His Ser Ala Arg Gly Ile Ala Ala Ser Ile Ser
       370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Pro Ala Ala Arg Val Leu
               405                 410                 415
Phe Met Phe Leu Ser Asp Glu Gly Thr Phe Gln Glu Ala Lys Ser Ala
```

-continued

```
                    420                 425                 430
Gly Ser Arg Gly Arg Thr Ile Ala Ala Leu Arg Cys Tyr Glu Asp
                435                 440                 445

Ile Phe Ser Leu Ala Arg Lys His Lys His Gly Met Leu Arg Asp Leu
    450                 455                 460

Asn Asn Ile Pro Pro
465

<210> SEQ ID NO 65
<211> LENGTH: 469
<212> TYPE: PRT
<213> ORGANISM: Artificial Sequence
<220> FEATURE:
<223> OTHER INFORMATION: synthetically generated variant

<400> SEQUENCE: 65

Met Ala Ala Asp Gln Gly Ile Phe Thr Asn Ser Val Thr Leu Ser Pro
  1               5                  10                  15

Val Glu Gly Ser Arg Thr Gly Gly Thr Leu Pro Arg Arg Ala Phe Arg
                 20                  25                  30

Arg Ser Cys Asp Arg Cys His Ala Gln Lys Ile Lys Cys Thr Gly Asn
             35                  40                  45

Lys Glu Val Thr Gly Arg Ala Pro Cys Gln Arg Cys Gln Gln Ala Gly
 50                  55                  60

Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Pro Cys Leu His
                 85                  90                  95

Met Ser Ser Pro Pro Val Pro Ser Gln Ser Leu Pro Leu Asp Val Ser
                100                 105                 110

Glu Ser His Ser Ser Asn Thr Ser Arg Gln Phe Leu Asp Pro Pro Asp
            115                 120                 125

Ser Tyr Asn Trp Leu Trp Thr Ser Ile Gly Thr Asp Glu Ala Ile Asp
    130                 135                 140

Thr Asp Cys Trp Gly Leu Ser Gln Cys Asp Gly Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
    195                 200                 205

Leu Glu Glu Ile Leu Leu Ala Val Thr Val Glu Trp Pro Lys Gln Glu
    210                 215                 220

Ile Trp Thr His Pro Ile Gly Met Phe Phe Asn Ala Ser Arg Arg Leu
225                 230                 235                 240

Leu Thr Val Leu Arg Gln Ala Gln Ala Asp Cys His Gln Gly Thr
                245                 250                 255

Leu Asp Glu Cys Leu Arg Thr Lys Asn Leu Phe Thr Ala Val His Cys
                260                 265                 270

Tyr Ile Leu Asn Val Arg Ile Leu Thr Ala Ile Ser Glu Leu Leu Leu
            275                 280                 285

Ser Gln Ile Arg Arg Thr Gln Asn Ser His Met Ser Pro Leu Glu Gly
    290                 295                 300

Ser Arg Ser Gln Ser Pro Ser Gly Asp Asp Thr Ser Ser Ser Ser Gly
```

-continued

```
            305                 310                 315                 320
His Ser Ser Val Asp Thr Ile Pro Phe Phe Ser Glu Asn Leu Pro Ile
                325                 330                 335
Gly Glu Leu Phe Ser Tyr Val Asp Pro Leu Thr His Ala Leu Phe Ser
            340                 345                 350
Ala Cys Thr Thr Leu His Val Gly Val Gln Leu Leu Arg Glu Asn Glu
                355                 360                 365
Ile Thr Leu Gly Val His Ser Ala Gln Gly Ile Ala Ala Ser Ile Ser
            370                 375                 380
Met Ser Gly Glu Pro Gly Glu Asp Ile Ala Arg Thr Gly Ala Thr Asn
385                 390                 395                 400
Ser Ala Arg Cys Glu Glu Gln Pro Thr Thr Pro Ala Ala Arg Val Leu
                405                 410                 415
Phe Met Phe Leu Ser Asp Glu Gly Ala Phe Gln Glu Gly Lys Ser Ala
            420                 425                 430
Gly Ser Arg Gly Arg Thr Ile Ala Ala Leu Arg Arg Cys Tyr Glu Asp
                435                 440                 445
Ile Phe Ser Leu Ala Arg Lys His Lys His Gly Met Leu Arg Asp Leu
            450                 455                 460
Asn Asn Ile Pro Pro
465
```

<210> SEQ ID NO 66
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 66

```
atggctgcag atcaaggtat attcacgaac tcggtcactc tctcgccagt ggagggttca      60
cgcaccggtg aacattaccc cgccgtgca ttccgacgct cttgtgatcg gtgtcatgca     120
caaaagatca atgtactgg aaataaggag gttactggcc gtgctccctg tcagcgttgc     180
cagcaggctg acttcgatg cgtctacagt gagcgatgcc caagcgcaa gctacgccaa     240
tccagggcag cggatctcgt ctctgctgac ccagatccct gcttgcacat gtcctcgcct     300
ccagtgccct cacagagctt gccgctagac gtatccgagt cgcattcctc aaatacctcc     360
cggcagtttc ttgatccacc ggacagctac gactggtcgt ggacctcgat tggcactgac     420
gaggctattg acactgactg ctgggggctg tcccaatgtg atggaggctt cagctgtcag     480
ttagagccaa cgctgccgga tctaccttcg cccttcgagt ctacggttga aaaagctccg     540
ttgccaccgg tatcgagcga cattgctcgt gcggccagtg cgcaacgaga gcttttcgat     600
gacctgtcgg cggtgtcgca ggaactggaa gagatccttc tggccgtgac ggtagaatgg     660
ccgaagcagg aaatctggac ccatcccatc ggaatgtttt tcaatgcgtc acgacggctt     720
cttactgtcc tgcgccaaca agcgcaggcc gactgccgtc aaggcacact agacgaatgt     780
ttacggacca agaacctctt tacggcagta cactgttaca tattgaatgt gcggattttg     840
accgccatat cggagttgct cctgtcgcaa attaggcgga cccagaacag ccatatgagc     900
ccactggaag ggagtcgatc ccagtcgccg agcagagacg acaccagcag cagcagcggc     960
cacagcagtg ttgacaccat accttctttt agcgagaacc tcctattggt gagctgttc    1020
ccctatgttg accccctgac acacgcccta ttctcggctt gcactacgtt acatgttggg   1080
```

```
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                    1410

<210> SEQ ID NO 67
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 67
atggctgcag atcaaggtat attcacgaac tcggtcactc tctcgccagt ggagggttca     60
cgcaccggtg gaacattacc ccgccgtgca ttccgacgct cttgtgatcg gtgtcatgca    120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt tctgctgac ccagatccct gcttgcacat gtcctcgcct     300
ccagtgccct cacagagctt gccgctagac gtatccgagt cgcattcctc aaatacctcc    360
tggcaatttc ttgatccacc ggacagctac gactggttgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagagtgg    660
ccgaagcagg aaatctggac ccatcccatc ggaatgtttt tcaatgcgtc acgacggctt    720
cttactgtcc tgcgccaaca gcgcaggcc gactgccatc aaggcacact agacgaatgt     780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacggcagtg ttgacaccat accottctttt agcgagaacc tccctattgg tgagctgttc    1020
tcctatgttg acccctgac acacgcccta ttctcggctt gcactacgtt acatgttggg     1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                    1410

<210> SEQ ID NO 68
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 68
```

-continued

| | |
|---|---|
| atggctgcag atcaaggtat attcacgaac tcggtcactc tctcgccagt ggagggttca | 60 |
| cgcaccggtg gaacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgacgcc ccaagcgcaa gctacgccaa | 240 |
| tccagggtag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggatctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat acccttcttt agcgagaacc tcccttattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggctttcca ggaggcaaag tctgctggtt cccgaggtcg aaccatcgca | 1320 |
| gcactgcgac gatgctatga ggatatcttt ccctcgccc gcaaacacaa acatggcatg | 1380 |
| ctcagagacc tcaacaatat tcctccatga | 1410 |

<210> SEQ ID NO 69
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 69

| | |
|---|---|
| atggctgcag atcaaggtat attcacgaac tcggtcactc tctcgccagt ggagggttca | 60 |
| cgcaccggtg gaacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgacgcc ccaagcgcaa gctacgccaa | 240 |
| tccagggcag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttgg aaaagctccg | 540 |
| ttgccaccgg tatcgagcga cattgctcgt gcggccagtg cgcaacgaga gcttttcgat | 600 |

-continued

```
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat acccttcttt agcgagaacc tccctattgg tgagctgttc   1020
tcctatgttg accccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt ccctcgccc gcaaacacaa acatggcatg   1380
ctcagagacc tcaacaatat tcctccatga                                    1410
```

<210> SEQ ID NO 70
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 70

```
atggctgcag atcaaggtat attcacgaac tcggtcactc tctcgccagt ggagggttca     60
cgcaccggtg gaacattacc ccgccgtgca ttccgacgct cttgtgatcg gtgtcatgca    120
caaaagatca aatgtactgg aaataaggag gttactggcc gtgctccctg tcagcgttgc    180
cagcaggctg gacttcgatg cgtctacagt gagcgacgcc ccaagcgcaa gctacgccaa    240
tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtc gcaacgaga gcttttcgat    600 gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat acccttcttt agcgagaacc tccctattgg tgagctgttc   1020
tcctatgttg accccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgactact ccagcggctc gggttttgtt catgttcttg   1260
```

```
agtgatgaag gggctttcca ggaggcaaag tctgctggtt cccgaggtcg aaccatcgca    1320
gcactgcgac gatgctatga ggatatcttt tccctcgccc gcaaacacaa acatggcatg    1380
ctcagagacc tcaacaatat tcctccatga                                     1410

<210> SEQ ID NO 71
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 71
atggctgcag atcaaggtat attcacgaac tcggtcactc tctcgccagt ggagggttca      60
cgcaccggtg gaacattacc ccgccgtgca ttccgacgct cttgtgatcg gtgtcatgca    120
caaaagatca aatgtactgg aaataaggag gttactggcc gtgctccctg tcagcgttgc    180
cagcaggctg gacttcgatg cgtctacagt gagcgatgcc caagcgcaa gctacgccaa     240 tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctggggctg tcccaatatg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaaa gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacgcagta cactgttaca tattgaatgt gcggatttg     840 gccgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat acccttcttt agcgagaacc tccctattgg tgagctgttc   1020
tcctatgttg acccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggctttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                   1410

<210> SEQ ID NO 72
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 72
atggctgcag atcaaggtat attcacgaac tcggtcactc tctcgccagt ggagggttca     60
cgcaccggtg gaacattacc ccgccgtgca ttccgacgct cttgtgatcg gtgtcatgca   120
```

-continued

```
caaaagatca aatgtactgg aaataaggag gttactggcc gtgctccctg tcagcgttgc      180
cagcaggctg gacttcgatg cgtctacagt gagcgacgcc ccaagcgcaa gctacgccaa      240
tccagggcag cggatctcgt ctctgctgac ccagatccct gcttgcacat gtcctcgcct      300
ccagtgccct cacagagctt gccgctagac gtatccgagt cgcattcctc aaatacctcc      360
cggcaatttc ttgatccacc ggacagctac gactggtcgt ggacctcgat tggcactgac      420
gaggctattg acactgactg ctgggggctg tcccaatgtg atggaggctt cagctgtcag      480
ttagagccaa cgctgccgga tctaccttcg cccttcgagt ctacggttga aaaagctccg      540
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatgtttt tcaatgcgtc acgacggctt      720
cttactgtcc tgcgccaaca agcgcaggcc gactgccatc aaggcgcact agacgaatgt      780
ttacggacca agaacctctt tacgcagta cactgttaca tattgaatgt gcggattttg      840
accgccatat cggagttgct cctgtcgcaa attaggcgga cccagaacag ccatatgagc      900
ccactggaag ggagtcgatc ccagtcgccg agcagagacg acaccagcag cagcagcggc      960
cacagcagtg ttgacaccat acccttcttt agcgagaacc tccctattgg tgagctgttc     1020
tcctatgttg acccctgac acacgcccta ttctcggctt gcactacgtt acatgttggg     1080
gtacaattgc tgcgtgagaa tgagattact ctgggagtac actccgccca gggcattgca     1140
gcttccatca gcatgagcgg ggaaccaggc gaggatatag ccaggacagg ggcgaccaat     1200
tccgcaagat gcgaggagca gccgaccact ccagcggctc gggttttgtt catgttcttg     1260
agtgatgaag gggctttcca ggaggcaaag tctgctggtt cccgaggtcg aaccatcgca     1320
gcactgcgac gatgctatga ggatatcttt tccctcgccc gcaaacacaa acatggcatg     1380
ctcagagacc tcaacagtat tcctccatga                                      1410
```

<210> SEQ ID NO 73
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 73

```
atggctgcag atcaaggtat attcacgaac tcggtcactc tctcgccagt ggagggttca       60
cgcaccggtg gaacattacc ccgccgtgca ttccgacgct cttgtgatcg gtgtcatgca      120
caaaagatca aatgtactgg aaataaggag gttactggcc gtgctccctg tcagcgttgc      180
cagcaggctg gacttcgatg cgtctacagt gagcgacgcc ccaagcgcaa gctacgccaa      240
tccagggcag cggatctcgt ctctgctgac ccagatccct gcttgcacat gtcctcgcct      300
ccagtgccct cacagagctt gccgctagac gtatccgagt cgcattcctc aaatacctcc      360
cggcaatttc ttgatccacc ggacagctac gactggtcgt ggacctcgat tggcactgac      420
gtggctattg acactgactg ctgggggctg tcccaatgtg atggaggctt cagctgtcag      480
ttagagccaa cgctgccgga tctaccttcg cccttcgagt ctacggttga aaaagctccg      540
ttgccaccgg tatcgagcga cattgctcgt gcggccagtg cgcaacgaga gcttttcgat      600
gacctgtcgg cggtgtcgca ggaactggaa gagatccttc tggccgtgac ggtagaatgg      660
ccgaagcagg aaatctggac ccatcccatc ggaatgtttt tcaatgcgtc acgacggctt      720
cttactgtcc tgcgccaaca agcgcaggcc gactgccatc aaggcacact agacgaatgt      780
```

| | |
|---|---|
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat accettcttt agcgagaacc tccctattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggctttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 74
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 74

| | |
|---|---|
| atggctgcag atcaaggtat attcacgaac tcggtcactc tctcgccagt ggagggttca | 60 |
| cgcaccggtg gaacattacc ccgccgtgca ttccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgacgcc caagcgcaa gctacgccaa | 240 |
| tccagggcag cggatctcgt ttctgctgac ccagatccct gcttgcacat gtcctcgcct | 300 |
| ccagtgccct cacagagctt gccactagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaacgt gcggattttg | 840 |
| accgccatat cggagttgct cctgtcgcaa attaggcgga cccagaacag ccatatgagc | 900 |
| ccactgaaag ggagtcgatc ccagtcgccg agcagagacg acaccagcag cagcagcggc | 960 |
| cacagcagtg ttgacaccat accettcttt agcgagaacc tccctattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggctttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 75
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 75

| | | | | | |
|---|---|---|---|---|---|
| atggctgcag | atcaaggtat | attcacgaac | tcggtcactc | tctcgccagt | ggagggttca | 60 |
| cgcaccggtg | aacattacc | ccgccgtgca | ttccgacgct | cttgtgatcg | gtgtcatgca | 120 |
| aaaaagatca | aatgtactgg | aaataaggag | gttactggcc | gtgctccctg | tcagcgttgc | 180 |
| cagcaggctg | gacttcgatg | cgtctacagt | gagcgatgcc | ccaagcgcaa | gctacgccaa | 240 |
| tccagggcag | cggatctcgt | tctgctgac | ccagatccct | gcttgcacat | gtcctcgcct | 300 |
| ccagtgccct | cacagagctt | gccgctagac | gtatccgagt | cgcattcctc | aaatacctcc | 360 |
| cggcaatttc | ttgatccacc | ggacagctac | gactggtcgt | ggacctcgat | tggcactgac | 420 |
| gaggctattg | acactgactg | ctggggggctg | tcccaatgtg | atggaggctt | cagctgtcag | 480 |
| ttagagccaa | cgctgccgga | tctaccttcg | cccttcgagt | ctacggttga | aaaagctccg | 540 |
| ttgccaccgg | tatcgagcga | cattgctcgt | gcggccagtg | cgcaacgaga | gcttttcgat | 600 |
| gacctgtcgg | cggtgtcgca | ggaactggaa | gagatccttc | tggccgtgac | ggtagaatgg | 660 |
| ccgaagcagg | aaatctggac | ccatcccatc | ggaatgtttt | tcaatgcgtc | acgacggctt | 720 |
| cttactgtcc | tgcgccaaca | gcgcaggcc | gactgccatc | aaggcacact | agacgaatgt | 780 |
| ttacggacca | agaacctctt | tacggcagta | cactgttaca | tattgaatgt | gcggattttg | 840 |
| accgccatat | cggagttgct | cctgtcgcaa | attaggcgga | cccagaacag | ccatatgagc | 900 |
| ccactggaag | ggagtcgatc | ccagtcgccg | agcagagacg | acaccagcag | cagcagcggc | 960 |
| cacagcagtg | ttgacaccat | accttcttt | agcgagaacc | tccctattgg | tgagctgttc | 1020 |
| tcctatgttg | accccctgac | acacgcccta | ttctcggctt | gcactacgct | acatgttggg | 1080 |
| gtacaattgc | tgcgtgagaa | tgagattact | ctggggagtac | actccgccca | gggcattgca | 1140 |
| gcttccatca | gcatgagcgg | ggaaccaggc | gaggatatag | ccaggacagg | ggcgaccaat | 1200 |
| tccgcaagat | gcgaggagca | gccgaccact | ccagcggctc | gggttttgtt | catgttcttg | 1260 |
| agtgatgaag | gggctttcca | ggaggcaaag | tctgctggtt | cccgaggtcg | aaccatcgca | 1320 |
| gcactgcgac | gatgctatga | ggatatcttt | tccctcgccc | gcaaacacaa | acatggcatg | 1380 |
| ctcagagacc | tcaacaatat | tcctccatga | | | | 1410 |

<210> SEQ ID NO 76
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 76

| | | | | | |
|---|---|---|---|---|---|
| atggctgcag | atcaaggtat | attcatgaac | tcggtcactc | tctctgcagt | ggagggttca | 60 |
| cgcaccagtg | aacattacc | ccgccgtgca | ttccgacgct | cttgtgatcg | gtgtcatgca | 120 |
| aaaaagatca | aatgtactgg | aaataaggag | gttactggcc | gtgctccctg | tcagcgttgc | 180 |
| cagcaggctg | gacttcgatg | cgtctacagt | gagcgatgcc | ccaagcgcaa | gctacgccaa | 240 |
| tccagggcag | cggatctcgt | tctgctgac | ccagatccct | gcttgcacat | gtcctcgcct | 300 |

```
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctggggctg tcccaatgtg atggaggctt cagctgtcag     480
ttagagccaa cgctgccgga tctaccttcg cccttcgagt ctacagttga aaaagctccg    540
ttgccaccgg tatcgagcga cattgctcgt gcggccagtg cgcaacgaga gcttttcgat    600
gacctgtcgc cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctatcgcaa attaggcgga cccagaacag ccatatgagc    900
ccactggaag ggagtcgatc ccagtcgccg agcagagacg acactagcag cagcagcggc    960
cacagcagtg ttgacaccat acccttcttt agcgagaacc tccctattgg tgagctgttc   1020
tcctatgttg accccctgac acacgcccta ttctcggctt gcactacgtt acatgttggg   1080
gtagaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggctttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                   1410

<210> SEQ ID NO 77
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 77
atggctgcag atcaaggtat attcacgaac tcggtcactc tctcgccagt ggagggttca     60
cacaccggtg gaacattacc ccgccgtgca ttccgacgcg cttgtgatcg gtgtcatgca    120
caaaagatca aatgtactgg aaataaggag gttactggcg gtgctccctg tcagcgttgc    180
cagcaggctg gacttcgatg cgtctacagt gagcgatgcc ccaagcgcaa gctacgccat    240
tccagggcat cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctggggctg tcccaatgtg atggaggctt cagctgtcag     480
ttagagccaa cgctgccgga tctaccttcg cccttcgagt ctacgttga  aaaagctccg    540
ttgccaccgg tatcgagcga cattgctcgt gcggccagtg cgcaacgaga gcttttcgat    600
gacctgtcgc cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggacg ggagtcgatc ccagtcgccg agcagagacg acaccagcag cagcagcggc    960
```

```
cacagcagtg ttgacaccat accottcttt agcgagaacc tccctattgg tgagctattc    1020
tcctatgttg accccctgac acacgccca ttctcggctt gcactacgtt acatgttggg    1080
gtacaattgc tgcgtgagaa tgagattact ctgggagtag actccgccca gggcattgca    1140
gcttccatca gcatgagcgg ggaaccaggc gaggatatag ccaggacagg ggcgaccaat    1200
tccgcaagat gcgaggagca gccgaccact ccagcggctc gggttttgtt catgttcttg    1260
agtgatgaag gggctttcca ggaggcaaag tctgctggtt cccgaggtcg aaccatcaca    1320
gtactgcgac gaagctatga ggatatcttt cccctcgccc gcaaacacaa acatggcatg    1380
ctcagagacc tcaacaatat tccttcatga                                     1410
```

<210> SEQ ID NO 78
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 78

```
atggctgcag atcaaggtat attcacgaac tcggtcactc tctcgccagt ggagggttca      60
cgcaccggtg gaacattacc ccgccgtgca ctccgacgct cttgtgatcg gtgtcatgca     120
caaaagatca aatgtactgg aaataaggag gttactggcc gtgctccctg tcagcgttgc     180
cagcaggctg gacttcgatg cgtctacagt gagcgatgcc ccaagcgcaa gctacgccaa     240
tccagggcag cggatctcgt ctctgctgac ccagatccct gcttgcacat gtcctcgcct     300
ccagtgccct cacagagctt gccgctagac gtatccgagt cgcattcctc aaatacctcc     360
cggcaatttc ttgatccacc ggacagctac gactggtcgt ggacctcgat tggcactgac     420
gaggctattg acactgactg ctgggggctg tcccaatgtg atggaggctt cagctgtcag     480
ttagagccaa cgctgccgga tctaccttcg cccttcgagt ctacggttga aaaagctccg     540
ttgccaccgg tatcgagcga cattgctcgt gcggccagtg cgcaacgaga gcttttcgat     600
gacctgtcgc cggtgtcgca ggaactggaa gagatccttc tggccgtgac ggtagaatgg     660
ccgaagcagg aaatctggac ccatcccatc ggaatgtttt tcaatgcgtc acgacggctt     720
cttactgtcc tgcgccaaca agcgcaggcc gactgccatc aaggcacact agacgaatgt     780
ttacggacca agaacctctt tacggcagta cactgttaca tattgaatgt gcggattttg     840
accgccatat cggagttgct cctgtcgcaa attaggcgga cccagaacag ccatatgagc     900
ccactggaag ggagtcgatc ccagtcgccg agcagagacg acaccagcag cagcagcggc     960
cacagcagtg ttgacaccat accottcttt agcgagaacc tccctattgg tgagctgttc    1020
tcctatgttg accccctgac acacgccta ttctcggctt gcactacgtt acatgttggg    1080
gtacaattgc tgcgtgagaa tgagattact ctgggagtac actccgccca gggcattgca    1140
gcttccatca gcatgagcgg ggaaccaggc gaggatatag ccaggacagg ggcgaccaat    1200
tccgcaagat gcgaggagca gccgatcact ccagcggctc gggttttgtt catgttcttg    1260
agtgatgaag gggctttcca ggaggcaaag tctgctggtt cccgaggtcg aaccatcgca    1320
gcactgcgac gatgctatga ggatatcttt cccctcgccc gcaaacacaa acatggcatg    1380
ctcagagacc tcaacaatat tcctccatga                                     1410
```

<210> SEQ ID NO 79
<211> LENGTH: 1410
<212> TYPE: DNA

<213> ORGANISM: Artificial Sequence
<220> FEATURE:
<223> OTHER INFORMATION: synthetically generated variant

<400> SEQUENCE: 79

| | | |
|---|---|---|
| atggctgcag atcaaggtat attcacgaac tcggtcactc tctcgccagt ggagggttca | 60 |
| cgcaccggtg aacattacc ccgccgtgca ctccgacgct cttgtgatcg gtgtcatgca | 120 |
| caaaagatca aatgtactgg aaataaggag gttactggcc gtgctccctg tcagcgttgc | 180 |
| cagcaggctg gacttcgatg cgtctacagt gagcgatgcc ccaagcgcaa gctacgccaa | 240 |
| tccagggcag cggatctcgt ctctgctgac ccagatccct gcttgcacat atcctcgcct | 300 |
| ccagtgccct cacagagctt accgctagac gtatccgatt cgcattcctc aaatacctcc | 360 |
| cggcaatttc ttgatccacc ggacagctac gactggtcgt ggacctcgat tggcactgac | 420 |
| gaggctattg acactaactg ctgggggctg tcccaatgtg atggaggctt cagctgtcag | 480 |
| ttagagtcaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| cctaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat acccttcttt agcgagaacc tcctattggt gagctgttc | 1020 |
| tcctatgttg acccctgac acacgcccta ttctcggctt gcactacgtt acatgttggg | 1080 |
| gtacaattgc tgcgtgagat tgagattact ctgggagtac actccgccca gggcattgca | 1140 |
| gcttccatca gcatgagcgg ggaaccaggc gaggatatag ccaggacagg ggcaaccaat | 1200 |
| tccgcaagat gcgaggagca gccgaccact ccagcggctc gggttttgtt catgttcttg | 1260 |
| agtgatgaag gggctttcca ggaggcaaag tctgctggtt cccgaggtcg aaccatcgca | 1320 |
| gcactgcgac gatgctatga ggatatcttt tccctcgccc gcaaacacaa atatggcatg | 1380 |
| ctcagagacc tcaacaatat tcctccatga | 1410 |

<210> SEQ ID NO 80
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 80

| | | |
|---|---|---|
| atggctgcag atcaaggtat attcacgaac tcggtcactc tctcgccagt ggagggttca | 60 |
| cgcaccggtg aacattacc ccgccgtgca ttccgacgct cttgtgatcg gtgtcatgca | 120 |
| caaaaggtca aatgtactgg aaataaggag gttactggcc gtgctccctg tcagcgttgc | 180 |
| cagcaggctg gacttcgatg cgtctacagt gagcgatgcc ccaagcgcaa gctacgccaa | 240 |
| tccagggcag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |

```
ttagagccaa cgctgccgga tctaccttcg cccttcgagt ctacggttga aaaagctccg        540
ttgccaccgg tatcgagcga cattgctcgt gcggccagtg cgcaacgaga gcttttcgat        600
gacctgtcgg cggtgtcgca ggaactggaa gagatccttc tggccgtgac ggtagaatgg        660
ccgaagcagg aaatctggac ccatcccatc ggaatgtttt tcaatgcgtc acgacggctt        720
cttactgtcc tgcgccaaca agcgcaggcc gactgccatc aaggcacact agacgaatgt        780
ttacggacca agaacctctt tacggcagta cactgttaca tattgaatgt gcggattttg        840
accgccatat cggagttgct cctgtcgcaa attaggcgga ccctgaacag ccatatgagc        900
ccactggaag ggagtcgatc ccagtcgccg agcagagacg acaccagcag cagcagcggc        960
cacagcagtg ttgacaccat acccttcttt agcgagaacc tcctattgg tgagctgttc       1020 tcctatgttg acccctgac acacgcccta ttctcggctt gcactacgtt acatgttggg       1080
gtacaattgc tgcgtgagaa tgagattact ctgggagtac actccgccca gggcattgca       1140
gcttccatca gcatgagcgg ggaaccaggc gaggatatag ccaggacagg ggcgaccaat       1200
tccgcaagat gcgaggagca gccgaccact ccagcggctc gggttttgtt catgttcttg       1260
agtgatgaag gggcttttcca ggaggcaaag tctgctggtt cccgaggtcg aaccatcgca       1320
gcactgcgac gatgctatga ggatatcttt tccctcgccc gcaaacacaa acatggcatg       1380
ctcagagacc tcaacaatat tcctccatga                                        1410

<210> SEQ ID NO 81
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 81
atggctgcag atcaaggtat attcacgaac tccgtcactc tctcgccagt ggagggttca         60
cgcaccggtg gaacattacc ccgccgtgca ttacgacgct cttgtgatcg gtgtcatgca        120
caaaagatca aatgtactgg aaataaggag gttactggcc gtgctccctg tcagcgttgc        180
cagcaggctg gacttcgatg cgtctacagt gagcgatgcc ccaagcgcaa gttacgccaa        240
tccagggcag cggatctcgt tctgctgac ccagatccct gcttgcacat gtcctcgcct        300
tcagtgccct cacagagctt gccgctagac gtatccgagt cgcattcctc aaatacctcc        360
cggcaatttc ttgatccacc ggacagctac gactggtcgt ggacctcgat tggcactgac        420
gaggctattg acactgactg ctgggggctg tcccaacgtg atggaggctt cagctctcag        480
ttaaagccaa cgctgccgga tctaccttcg cccttcgagt ctacggttga aaaagctccg        540
ttgccaccgg tatcgagcga cattgctcgt gcggccagtg cgcaacgaga gcttttcgat        600
gacctgtcgg cggtgtcgca ggaactggaa gagatccttc tggccgtgac ggtagaatgg        660
ccgaagcagg aaatctggac ccatcccatc ggaatgtttt tcaatgcgtc acgacggctt        720
cttactgtcc tgcgccaaca agcgcaggcc gactgccatc aaggcacact agacgaatgt        780
ttacggacca agaacctctt tacggcagta cactgttaca tattgaatgt gcggattttg        840
accgccatat cggagttgct actgtcgcaa attaggctga cccagaacag ccatatgagc        900
ccactggaag ggagtcgatc ccagtcgccg aacagagacg acaccagcag cagcagcggc        960
cacagcagtg ttgacaccat acccttcttt agcgagaacc tcctattgg tgagctgttc       1020 tcctatgttg acccctgac acacgcccta ttctcggctt gcactacgtt acatgttggg       1080
```

```
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                      1410
```

<210> SEQ ID NO 82
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 82

```
atggctgcag atcaaggtat attcactaac tcggtcacta tctcgccagt ggtgggttca     60
cgcaccggtg gaacattacc ccgccgtgca ttccgacgct cttgtgatcg gtgtcatgca    120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt ctctgctgac ccagatccct gcttgcacat gtcctcgcct    300
ccagtgccct cacagagttt gccgctagac gtatccgagt cgcattcctc aaatacctcc    360
cggcaatttc ttgatccacc ggacagctac gactggtcgt ggacctcgat ttgcactgac    420
gaggctattg acactgactg ctgggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat acccttcttt agcgagaacc tccctattgg tgggctgttc   1020
tcctatgttg accccctgac acacgcccta ttctcggctt gcactacgtt acatgttggg   1080
ctacaattgc tgcgtgagaa tgagattact ctgggagtac actccgccca gggcattgca   1140
gcttccatca gcatgagcgg ggaatcaggc gaggatatag ccaggacagg ggcgaccagt   1200
tccgcaagat gcgaggagca gccgaccact ccagcggctc gggttttgtt catgttcttg   1260
agtgatgaag gggcttttcca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                      1410
```

<210> SEQ ID NO 83
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 83

| | |
|---|---|
| atggctgcag atcaaggtat attcacgaac tcggtcactc tctcgccagt ggagggttca | 60 |
| cgcaccggtg gaacattacc ccgccgtgca ttccgacgct cttgtgatcg gtgtcatgca | 120 |
| cgaaagatca aatgtactgg aaataaggag gttactggcc gtgctccctg tcagcgttgc | 180 |
| cagcaggctg gacttcgatg cgtctacagt gagcgatgcc ccaagcgcaa gctacgccaa | 240 |
| tccagggcag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt atacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca agcgcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat acccttcttt agcgagaacc tcccctattgg tgagctgttc | 1020 |
| tcctatgttg accccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccacaagat gcgaggagca gccgaccact ccagcggctc gggttttgtt catgttcttg | 1260 |
| agtgatgaag gggctttcca ggaggcaaag tctgctggtt cccgaggtcg aaccatcgca | 1320 |
| gcactgcgac gatgctatga ggatatcttt ccctcgccc gcaaacacaa acatggcatg | 1380 |
| ctcagagacc tcaacaatat tcctccatga | 1410 |

<210> SEQ ID NO 84
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 84

| | |
|---|---|
| atggctgcag atcaaggtat attcacgaac tcggtcactc tctcgccagt ggagggttca | 60 |
| cgcaccggtg gaacattacc ccgccgtgca ttgcgacgct cttgtgatcg gtgtcatgca | 120 |
| caaaagatca aatgtactgg aaataaggag gttattggcc gtgctccctg tcagcgttgc | 180 |
| cagcaggctg gacttcgatg cgtatacagt gagcgatgcc ccaagcgcaa gctacgccaa | 240 |
| tccagggcag cggatctcgt ctctgctgac ccagatccct gcttgcacat gtcctcgcct | 300 |
| caagtgccct cacagagctt gtcgctagac atatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |

-continued

```
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat acccttcttt agcgagaacc tccctattgg tgagctgttc   1020
tcctatgttg accccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcattcca ggaggcaaag tctgctggtt cccgaggtcg aaccatcgca   1320
gcactgcgac gatgctatga ggatatcttt ccctcgccc gcaaacacaa acatggcatg   1380
ctcagagacc tcaacaatat tcctccatga                                    1410
```

<210> SEQ ID NO 85
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 85

```
atggctgcag atcaaggtat attcacgaac tcggtcactc tctcaccagt ggagggttca     60
cgcaccggtg gaacattacc ccgccgtgca ttccgacgct cttgtgatcg gtgtcatgca    120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cgaatctcgt ctctgctgac ccagatccct gcttacacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggcttttg acactgactg ctgggggcta tcccaatgtg atggaggctt cagctgtcag    480
ctagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatctttt tcaatgcgtc acgacggctt    720
cttactgtcc tgcgccagca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acatcagcag cagcagcggc    960
cacagcagtg ttgacaccat acccttcttt agcgagaacc tccctattgg tgagctgttc   1020
tcctatgttg accccctgac acacgcccta ttctcggctt gcactacgtt acatgttggg   1080
gtacaattgc tgcgtgagaa tgagattact ctgggagtac actccgccca gggcattgca   1140
gcttacatca gcaagagcgg ggaaccaggc gaggatatag ccaggacagg ggcgaccaat   1200
tccgcaagat gcgaggagca gccgaccact ccagcggctc gggtgttgtt catgttcttg   1260
```

| | |
|---|---:|
| agtgatgaag gggctttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 86
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 86

| | |
|---|---:|
| atggctgcag atcaaggtat attcacgaac tcggtcactc tctcgccagt ggagggttca | 60 |
| cgcaccggtg gaacattacc ccgccgtgca ttccgacgct cttgtgatcg gtgtcatgca | 120 |
| caaaagatca aatgtattgg aaataaggag gttactggcc gtgctccctg tcagcgttgc | 180 |
| caacgggctg gacttcgatg cgtctacagt gagcgatgcc ccaagcgcag gctacgccaa | 240 |
| tccaggcag cggatctcgt ctctgctgac ccagatccct gcttgcacat gtcctcgcct | 300 |
| ccagtgccct cacagagctt gccgctagac gtatccgagt cgcattcctc aaatacctcc | 360 |
| cggcaatttc ttgatccacc ggacagctac gactggtcgt ggacctcgat tggcactgac | 420 |
| gaggctattg acactgactg ctgggggctg tcccaatgtg atggaggctt cagctgtcag | 480 |
| ttagagccaa cgctgccgga tctaccttcg cccttcgagt ctacggttga aaaagctccg | 540 |
| ttgccaccgg tatcgagcga cattgctcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcttc acgacggctt | 720 |
| cttactgtcc tgcgccaaca agctcaggcc gactgccatc aaggcacact agacgaatgt | 780 |
| ttacggacca agaacctctt tacggcagta cactgttaca tattgaatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagctgtg tcgacaccat accttctttt agcgagaacc tccctattgg tgagctgttc | 1020 |
| tcctatgttg accccctgac acacgcccta ttctcggctt gcactacgtt acatgttggg | 1080 |
| gtacaattgc tgcgtgagta tgagattact ctgggaatac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggctttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagatc tcaacaatat tcctccatga | 1410 |

<210> SEQ ID NO 87
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 87

| | |
|---|---:|
| atggctgcag atcaaggtat attcacgaac tcggtcactc tctcgccagt ggagggttca | 60 |
| cgcaccggtg gaacattacc ccgccgtgca ttccgacgct cttgtgatcg gtgtcatgca | 120 |

```
cgaaagatca aatgtactgg aaataaggag gttactggcc gtgctccctg tcagcgttgc        180
cagcaagctg gacttcgatg cgtctatagt gagcgatgcc ccaagcgcaa gctacgccaa        240
tccagggcag cggatctcgt ctctgctgac ccagatccct gcttgcacat gtcctcgcct        300
ccagtgccct cacagagctt gccgctagac gtatccgagt cgcattcctc aaatacctcc        360
cggcaatttc ttgatccacc ggacagctac gactggtcgt ggacctcgat tggcactgac        420
gaggctattg acactgactg ctgggggctg tcccaatgtg atggaggctt cagctgtcag        480
ctagagccaa cgctgccgga tctaccttcg cccttcgagt ctacggttga aaaagctccg        540
ttgccaccgg tatcgagcga cattgctcgt gcggccagtg cgcaacgaga gcttttcgat        600
gacctgtcgg cggtgtcgca ggaactggaa gagatccttc tggccgtgac ggtagaatgg        660
ccgaagcagg aaatctggac ccatcccatc ggaatgtttt tcaatgcgtc acgacggctt        720
cttactgtcc tgcgccaaca agcgcaggcc gactgccatc aaggcacact agacgaatgt        780
ttacggacca agaacctctt tacgcagta cactgttaca tattgaatgt gcggattttg        840
accgccatat cggagttgct cctgtcgcaa attaggcgga tccagaacag ccatatgagc        900
ccactggaag ggagtcgatc ccagtcgctg agcagagacg acaccagcag cagtagcggc        960
cacagcagtg ttgacaccat acccttcttt agcgagaacc tccctattga tgagctgttc       1020
tcctatgttg accccctgac acacgcccta ttctcggctt gcactacgtt acatgttggg       1080
gtacaattgc tgcgtgagaa tgagattact ctgggagtac actccgccca gggcattgca       1140
gcttccatca gcatgagcgg ggaactaggc gaggatatag tcaggacagg ggcgaccaat       1200
tccgcaagat gcgaggagca gccgaccact ccagcggctc gggttttgtt catgttcttg       1260
agtgatgaag gggcttttcca ggaggcaaag tctgctggtt cccgaagtcg aaccatcgca       1320
gcactgcgac gatgctatga ggatatcttt tccctcgccc gcaaacacaa acatggcatg       1380
ctcagagacc tcaacaatat tcctccatga                                         1410
```

<210> SEQ ID NO 88
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 88

```
atggctgcag atcaaggtat attcacgaac tcggtcactc tctcaccagt ggagggttca         60
cgcaccggtg gaacattacc ccgccgtgca ttccgacgct cttgtgatcg gtgtcatgca        120
caaaagatca aatgtactgg aaataaggag gttaatggcc gtgctccctg tcagcgttgc        180
cagcaggctg gacttcgatg cgtctacagt gagcgatgcc ccaagcgcaa gctacgccaa        240
tccagggcag cggatctcgt ctctgctgac ccagatccct gcttgcacat gtcctcgcct        300
ccagtgccct cccagagctt gccgctagac atatccgagt cgcattcctc aaatacctcc        360
cggcaatttc ttgatccacc ggacagctac gactggtcgt ggacctcgat tggcattgac        420
gaggctattg acactgactg ctgggggctg tcccaatgtg atggaggctt cagctgtcag        480
ttagagccaa cgctgccgga tctaccttcg cccttcgagt ctacggttga aaaagctccg        540
ttgccaccga tatcgagcga cattgctcgt gcggccagtg cgcaacgaga gcttttcgat        600
gacctgtcgg cggtgtcgca ggaactggaa gagatccttc tggccgtgac ggtagaatgg        660
ccgaagcagg aaatctggac ccatcccatc ggaatgtttt tcaatgcgtc acgacggctt        720
cttactgtcc tgcgccaaca agcgcaggcc gactgccatc aaggcacact agacgaatgt        780
```

-continued

| | |
|---|---|
| ttacggacca agaacctctt tacggcagta cactgttaca tattgaatgt gcggattttg | 840 |
| gccgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat accccttcttt agcgagaacc tccctattgg tgagctgttc | 1020 |
| tcctatgttg acccccctgac acacgcccta ttctcggctt gcactacgtt acatgttggg | 1080 |
| gtacaattgc tgcgtgagaa tgagattact ctgggagtac actccgccca gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag gggcttttcca ggaggcaaag tctgctggtt cccgaggtcg aaccatcgca | 1320 |
| gcactgcgac gatgctatga ggatatcttt tccctcgccc gcaaacacaa acatggcatg | 1380 |
| ctcagagacc tcaacaatat tcctccatga | 1410 |

<210> SEQ ID NO 89
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 89

| | |
|---|---|
| atggctgcag aacaaggtat attcacgaac tcggtcactc tctcgccagt ggagggttca | 60 |
| cgcaccggtg gaacattacc ccgccgtgca ttccgacgct cttgtgatcg gtgtcatgca | 120 |
| cgaaagatca aatgtactgg aaataaggag gttactggcc gtgctccctg tcagcgttgc | 180 |
| cagcaggctg gacttcgatg tgtctacagt gagcgatgcc caagcgcaa gctacgccaa | 240 |
| tccagggcag cggatctcat ctctgctgac ccagatccct gcttgcacat gtcctcgcct | 300 |
| ccagtgccct cacagagctt gccgctagaa gtatccgagt cgcattcctc aaatacctcc | 360 |
| cggcaatttc ttgatccacc ggacagctac gactggtcgt ggacctcgat tggcactgac | 420 |
| aaggctattg acactgactg ctgggggctg tcccaatgtg atggaggctt cagctgtcag | 480 |
| ttagagccaa cgctgccgga tctaccttcg ccctttgagt ctacggttga aaaagctccg | 540 |
| ttgccaccgg tatcgagcga cattactcgt gcggccagtg cgcaacgaga gcttttcgat | 600 |
| gacctgtcgg cggtgtcgca ggaactggaa gagatccttc tggccgtgac ggtagaatgg | 660 |
| ccgaagcagg aaatctggac ccatcccatc ggaatgtttt tcaatgcgtc acgacggctt | 720 |
| cttactgtcc tgcgccaaca gcgcaggcc gactgccatc aaggcacact agacgaatgt | 780 |
| ttacggacca agaacctctt tacggcagta cactgttaca tattggatgt gcggattttg | 840 |
| accgccatat cggagttgct cctgtcgcaa attaggcgga cccagaacag ccatatgagc | 900 |
| ccactggaag ggagtcgatc ccagtcgccg agcagagacg acaccagcag cagcagcggc | 960 |
| cacagcagtg ttgacaccat accccttcttt agcgagaacc tccctattgg tgagctgttc | 1020 |
| tcctatgttg acccccctgag acacgcccta ttctcggctt gcactacgtt acatgttggg | 1080 |
| gtacaattgc tgcgtgagat tgagattact ctgggagtac actccgcccg gggcattgca | 1140 |
| gcttccatca gcatgagcgg ggaaccaggc gaggatatag ccaggacagg ggcgaccaat | 1200 |
| tccgcaagat gcgaggagca gccgaccact ccagcggctc gggttttgtt catgttcttg | 1260 |
| agtgatgaag ggacttttcca ggaggcaaag tctgctggtt cccgaggtcg aaccatcgca | 1320 |
| gcactgcgac gatgctatga ggatatcttt tccctcgccc gcaaacacaa acatggcatg | 1380 |

```
ctcagagacc tcaacaatat tcctccatga                                  1410
```

<210> SEQ ID NO 90
<211> LENGTH: 1410
<212> TYPE: DNA
<213> ORGANISM: Artificial Sequence
<220> FEATURE:
<223> OTHER INFORMATION: synthetically generated variant

<400> SEQUENCE: 90

```
atggctgcag atcaaggtat attcacgaac tcggtcactc tctcgccagt ggagggttca     60
cgcaccggtg aacattaccc cgccgtgca ttccgacgct cttgtgatcg gtgtcatgca    120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt ctctgctgac ccagatccct gcttgcacat gtcctcacct    300
ccagtgccct cacagagctt gccgctagac gtatccgagt cgcattcctc aaatacctcc    360
cggcaatttc ttgatccacc ggacagctac aactggttgt ggacctcgat tggcactgac    420
gaggctattg acactgactg ctgggggctg tcccaatgtg atggaggctt cagctgtcag    480
ttagagccaa cgctgccgga tctaccttcg cccttcgaat ctacggttga aaaagctccg    540
ttgccaccgg tatcgagcga cattgctcgt gcggccagtg cgcaacgaga gcttttcgat    600
gacctgtcgg cggtgtcgca ggaactggaa agatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacgcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcggagacg acaccagcag cagcagcggc    960
cacagcagtg ttgacaccat accttctt agcgagaacc tccctattgg tgagctgttc   1020
tcctatgttg acccctgac acacgcccta ttctcggctt gcactacgtt acatgttggg   1080
gtacaattgc tgcgtgagaa tgagattact ctgggagtac actccgccca gggtattgca   1140
gcttccatca gcatgagcgg ggaaccaggc gaggatatag ccaggacagg gcgaccaat   1200
tccgcaagat gcgaggagca gccgaccact ccagcggctc gggttttgtt catgttcttg   1260
agtgatgaag gggctttcca ggagggaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                  1410
```

<210> SEQ ID NO 91
<211> LENGTH: 469
<212> TYPE: PRT
<213> ORGANISM: Aspergillus terreus

<400> SEQUENCE: 91

```
Met Ala Ala Asp Gln Gly Ile Phe Thr Asn Ser Val Thr Leu Ser Pro
  1               5                  10                  15

Val Glu Gly Ser Arg Thr Gly Gly Thr Leu Pro Arg Arg Ala Phe Arg
             20                  25                  30

Arg Ser Cys Asp Arg Cys His Ala Gln Lys Ile Lys Cys Thr Gly Asn
         35                  40                  45

Lys Glu Val Thr Gly Arg Ala Pro Cys Gln Arg Cys Gln Gln Ala Gly
     50                  55                  60
```

```
Leu Arg Cys Val Tyr Ser Glu Arg Cys Pro Lys Arg Lys Leu Arg Gln
 65                  70                  75                  80

Ser Arg Ala Ala Asp Leu Val Ser Ala Asp Pro Asp Pro Cys Leu His
                 85                  90                  95

Met Ser Ser Pro Pro Val Pro Ser Gln Ser Leu Pro Leu Asp Val Ser
            100                 105                 110

Glu Ser His Ser Ser Asn Thr Ser Arg Gln Phe Leu Asp Pro Pro Asp
            115                 120                 125

Ser Tyr Asp Trp Ser Trp Thr Ser Ile Gly Thr Asp Glu Ala Ile Asp
130                 135                 140

Thr Asp Cys Trp Gly Leu Ser Gln Cys Asp Gly Phe Ser Cys Gln
145                 150                 155                 160

Leu Glu Pro Thr Leu Pro Asp Leu Pro Ser Pro Phe Glu Ser Thr Val
                165                 170                 175

Glu Lys Ala Pro Leu Pro Pro Val Ser Ser Asp Ile Ala Arg Ala Ala
            180                 185                 190

Ser Ala Gln Arg Glu Leu Phe Asp Asp Leu Ser Ala Val Ser Gln Glu
            195                 200                 205

Leu Glu Glu Ile Leu Leu Ala Val Thr Val Glu Trp Pro Lys Gln Glu
210                 215                 220

Ile Trp Thr His Pro Ile Gly Met Phe Phe Asn Ala Ser Arg Arg Leu
225                 230                 235                 240

Leu Thr Val Leu Arg Gln Gln Ala Gln Ala Asp Cys His Gln Gly Thr
                245                 250                 255

Leu Asp Glu Cys Leu Arg Thr Lys Asn Leu Phe Thr Ala Val His Cys
            260                 265                 270

Tyr Ile Leu Asn Val Arg Ile Leu Thr Ala Ile Ser Glu Leu Leu Leu
            275                 280                 285

Ser Gln Ile Arg Arg Thr Gln Asn Ser His Met Ser Pro Leu Glu Gly
            290                 295                 300

Ser Arg Ser Gln Ser Pro Ser Arg Asp Asp Thr Ser Ser Ser Ser Gly
305                 310                 315                 320

His Ser Ser Val Asp Thr Ile Pro Phe Phe Ser Glu Asn Leu Pro Ile
                325                 330                 335

Gly Glu Leu Phe Ser Tyr Val Asp Pro Leu Thr His Ala Leu Phe Ser
            340                 345                 350

Ala Cys Thr Thr Leu His Val Gly Val Gln Leu Leu Arg Glu Asn Glu
            355                 360                 365

Ile Thr Leu Gly Val His Ser Ala Gln Gly Ile Ala Ala Ser Ile Ser
370                 375                 380

Met Ser Gly Glu Pro Gly Glu Asp Ile Ala Arg Thr Gly Ala Thr Asn
385                 390                 395                 400

Ser Ala Arg Cys Glu Glu Gln Pro Thr Thr Pro Ala Ala Arg Val Leu
                405                 410                 415

Phe Met Phe Leu Ser Asp Glu Gly Ala Phe Gln Glu Ala Lys Ser Ala
            420                 425                 430

Gly Ser Arg Gly Arg Thr Ile Ala Ala Leu Arg Arg Cys Tyr Glu Asp
            435                 440                 445

Ile Phe Ser Leu Ala Arg Lys His Lys His Gly Met Leu Arg Asp Leu
450                 455                 460

Asn Asn Ile Pro Pro
465
```

-continued

```
<210> SEQ ID NO 92
<211> LENGTH: 1410
<212> TYPE: DNA
<213> ORGANISM: Aspergillus terreus

<400> SEQUENCE: 92
atggctgcag atcaaggtat attcacgaac tcggtcactc tctcgccagt ggagggttca      60
cgcaccggtg aacattacc ccgccgtgca ttccgacgct cttgtgatcg gtgtcatgca     120
caaaagatca aatgtactgg aaataaggag gttactggcc gtgctccctg tcagcgttgc    180
cagcaggctg gacttcgatg cgtctacagt gagcgatgcc ccaagcgcaa gctacgccaa    240
tccagggcag cggatctcgt ctctgctgac ccagatccct gcttgcacat gtcctcgcct    300
ccagtgccct cacagagctt gccgctagac gtatccgagt cgcattcctc aaatacctcc    360
cggcaatttc ttgatccacc ggacagctac gactggtcgt ggacctcgat tggcactgac    420
gaggctattg acactgactg ctggggctg tcccaatgtg atggaggctt cagctgtcag    480
ttagagccaa cgctgccgga tctaccttcg cccttcgagt ctacggttga aaaagctccg    540
ttgccaccgg tatcgagcga cattgctcgt gcggccagtg cgcaacgaga gcttttcgat    600
gacctgtcgg cggtgtcgca ggaactggaa gagatccttc tggccgtgac ggtagaatgg    660
ccgaagcagg aaatctggac ccatcccatc ggaatgtttt tcaatgcgtc acgacggctt    720
cttactgtcc tgcgccaaca agcgcaggcc gactgccatc aaggcacact agacgaatgt    780
ttacggacca agaacctctt tacggcagta cactgttaca tattgaatgt gcggattttg    840
accgccatat cggagttgct cctgtcgcaa attaggcgga cccagaacag ccatatgagc    900
ccactggaag ggagtcgatc ccagtcgccg agcagagacg acaccagcag cagcagcggc    960
cacagcagtg ttgacaccat acccttcttt agcgagaacc tccctattgg tgagctgttc   1020
tcctatgttg acccctgac acacgcccta ttctcggctt gcactacgtt acatgttggg   1080
gtacaattgc tgcgtgagaa tgagattact ctgggagtac actccgccca gggcattgca   1140
gcttccatca gcatgagcgg ggaaccaggc gaggatatag ccaggacagg ggcgaccaat   1200
tccgcaagat gcgaggagca gccgaccact ccagcggctc gggttttgtt catgttcttg   1260
agtgatgaag gggcttttca ggaggcaaag tctgctggtt cccgaggtcg aaccatcgca   1320
gcactgcgac gatgctatga ggatatcttt tccctcgccc gcaaacacaa acatggcatg   1380
ctcagagacc tcaacaatat tcctccatga                                      1410
```

LOVE VARIANT REGULATOR MOLECULES

BACKGROUND OF THE INVENTION

1. Field of the Invention

The invention relates to the fields of microbiology and molecular biology. In particular, the invention relates to the field of mycology and the production of secondary metabolites from fungi.

2. Summary of the Related Art

Secondary metabolites are a major source of commercially useful products such as food additives, vitamins, and medicines for the treatment of a wide variety of infections and diseases. By way of example, in 1997 the statin drugs lovastatin, simvastatin, and pravastatin, fungal secondary metabolites used in the treatment of hypercholesteremia, together had US sales of US$7.53 billion (Sutherland et al., *Current Opinion In Drug Discovery & Development* 4:229–236 (2001)). The cost and availability of these plant, bacterial and fungal metabolites are frequently determined by limitations imposed on production and purification of these compounds from culture. This problem is frequently exacerbated by the fact that these products are generally produced during the stationary phase of bacterial and fungal growth.

A wide variety of methods have been utilized to increase the amount of secondary metabolite produced in culture. Studies have demonstrated the importance of carefully designing the medium in which a fungus is grown to maximize the amount of a secondary metabolite produced (see, e.g., Hajjaj H, et al., *Appl. Environ. Microbiol.* 67:2596–602 (2001); Lesova, K., et al., *J. Basic Microbiol.* 40:369–75 (2000)). In addition, the method of culture or fermentation also impacts directly on the amount of secondary metabolite produced. For example, see Robinson, T., et al. (*Appl. Microbiol. Biotechnol.* 55:284–289 (2001)), which demonstrates the advantages of solid state (substrate) fermentation.

In addition to the manipulation of culture and media conditions, genetic approaches have been taken to increase secondary metabolite production. For example, the production of penicillin is limited by the activity of two enzymes, encoded by the ipnA and acvA genes, both of which are regulated by the pacC protein, a zinc-finger transcription factor. Naturally occurring mutant alleles of the pacC locus are known to possess more transcription-activating activity than the cognate, wild-type allele (see, e.g., Tilburn et al. *EMBO J.* 14(4):779–790 (1995)). Thus, one genetic approach to increasing secondary metabolite production is to identify and isolate naturally occurring mutant alleles, the expression of which leads to increased secondary metabolite production.

Although many regulators of secondary metabolite production in many organisms are known, not all of the organisms that produce secondary metabolites are amenable to genetic or molecular genetic manipulation. Thus, these systems are not generally useful as a source for the isolation of naturally occurring mutant alleles and are even less useful for the deliberate manipulation of secondary metabolite regulator protein structure with the aim of creating improved regulators of secondary metabolite production.

It would be advantageous to have improved regulators of the biosynthetic enzymes responsible for secondary metabolite production. For example, recent studies suggest increasing usage of statin drugs, e.g., see Waters D. D., *Am. J. Cardiol.* 88:10F–5F (2001)). Thus, demand for statin drugs is likely to increase substantially. In order to meet the demand for these and other secondary metabolites, new and improved methods for the production of secondary metabolites must be identified.

BRIEF SUMMARY OF THE INVENTION

The invention provides improved secondary metabolite regulator proteins that enable increased production of secondary metabolites. The invention also provides methods to make these improved regulator proteins.

In a first aspect, the invention provides a variant regulator protein of secondary metabolite production with increased activity than that of the cognate, wild-type protein. In certain embodiments of this aspect of the invention, the regulator protein is a fungal regulator protein.

In an embodiment of the first aspect, the invention provides an improved regulator protein comprising an amino acid sequence coding for a variant lovE protein having at least one specific mutation that gives rise to greater transcription-activating properties of the regulator protein and/or induction of secondary metabolite synthesis.

By way of non-limiting example, certain preferred regulator proteins of this aspect of the invention include at least one of the following mutations: (1) a Group 6 amino acid residue mutated to a Group 2 amino acid residue at position 31, in one embodiment the mutation represented by F31L; (2) a Group 3 amino acid residue mutated to a Group 5 amino acid residue at position 41, in one embodiment the mutation represented by Q41K or Q41R; (3) a Group 4 amino acid residue mutated to a Group 2 amino acid residue at position 52, in one embodiment the mutation represented by T52I; (4) a Group 4 amino acid residue mutated to a Group 3 amino acid residue at position 52, in one embodiment the mutation represented by T52N; (5) a Group 4 amino acid residue mutated to a Group 5 amino acid residue at position 73, in one embodiment the mutation represented by C73R; (6) a Group 1 amino acid residue mutated to a Group 4 amino acid residue at position 101, in one embodiment the mutation represented by P101S; (7) a Group 1 amino acid residue mutated to a Group 3 amino acid residue at position 101, in one embodiment the mutation represented by P101Q; (8) a valine amino acid residue mutated to another Group 2 amino acid residue at position 111, in one embodiment the mutation represented by V111I; (9) a Group 4 amino acid residue mutated to a Group 2 amino acid residue at position 133, in one embodiment the mutation represented by S133L; (10) a Group 3 amino acid residue mutated to a Group 2 amino acid residue at position 141, in one embodiment the mutation represented by E141V; (11) a Group 3 amino acid residue mutated to a Group 5 amino acid residue at position 141, in one embodiment the mutation represented by E141K; (12) a Group 4 amino acid residue mutated to Group 6 amino acid residue at position 153, in one embodiment the mutation represented by C153Y; (13) a Group 4 amino acid residue mutated to a Group 5 amino acid residue at position 153, in one embodiment the mutation represented by C153R; (14) a Group 4 amino acid residue mutated to a Group 1 amino acid residue at position 281, in one embodiment the mutation represented by T281A; (15) a Group 3 amino acid residue mutated to a Group 2 amino acid residue at position 367, in one embodiment the mutation represented by N367I; (16) a Group 3 amino acid residue mutated to a Group 6 amino acid residue at position 367, in one embodiment the mutation represented by N367Y; (17) a Group 1 amino acid residue mutated to Group 4 amino acid residue at position 389, in one embodiment the mutation represented by P389S; and (18) a Group 1 amino acid residue mutated to a Group 2 amino acid residue at position 389, in one embodiment the mutation represented by P389L.

In some embodiments of the first aspect, the invention provides regulator proteins with at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen of the above described specific mutations.

In other embodiments of the first aspect, the invention provides an isolated lovE variant regulator protein selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, and SEQ ID NO:65.

In a second aspect, the invention provides a nucleic acid molecule encoding a lovE regulator of the first aspect of the invention. By way of non-limiting example, the invention provides a nucleic acid molecule encoding the lovE variant regulator protein selected from the group consisting of SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:78, SEQ ID NO:79, SEQ ID NO:81, SEQ ID NO:82, SEQ ID NO:83, SEQ ID NO:84, SEQ ID NO:86, SEQ ID NO:87, SEQ ID NO:88, SEQ ID NO:89, and SEQ ID NO:90.

In a third aspect, the invention provides a method of increasing the activity of a protein that regulates secondary metabolite production comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; and (c) selecting a variant regulator protein with more activity than the cognate, wild-type protein.

In various embodiments of the third aspect, the secondary metabolite is a fungal secondary metabolite. In certain embodiments of the third aspect, the protein regulator of secondary metabolite production is a transcription factor. In certain embodiments of the third aspect, the protein regulator of secondary metabolite production is a transmembrane transporter, protein that mediates secretion, kinase, G-protein, cell surface receptor, GTPase activating protein, guanine nucleotide exchange factor, phosphatase, protease, phosphodiesterase, bacterial protein toxin, importin, RNA-binding protein, SCF complex component, adherin, or protein encoded within a biosynthetic cluster. In certain other embodiments of the third aspect, the variant regulator protein is selected to have more activity in a heterologous cell and/or more activity in a homologous cell than the cognate, wild-type regulator protein. In certain embodiments, the variant regulator protein is selected to have more activity in a heterologous cell and/or more activity in a homologous cell than the cognate, wild-type protein and to cause more secondary metabolite to be produced in a homologous cell and/or a heterologous cell when compared to the cognate, wild-type regulator protein. In a particularly preferred embodiment, the variant regulator protein is a lovE variant regulator protein.

In a fourth aspect, the invention provides a method of increasing production of a secondary metabolite comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; (c) selecting a variant regulator protein with more activity than the cognate, wild-type protein; and (d) expressing the selected variant regulator protein in a cell, thereby increasing production of the secondary metabolite in the cell.

In various embodiments of the fourth aspect, the secondary metabolite is a fungal secondary metabolite. In certain embodiments of the third aspect, the protein regulator of secondary metabolite production is a transcription factor. In certain embodiments of the fourth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain other embodiments of the fourth aspect, the variant regulator protein is selected to have more activity in a heterologous cell and/or more activity in a homologous cell. In certain embodiments, the variant regulator protein is selected to have more activity in a heterologous cell and/or more activity in a homologous cell and to cause more secondary metabolite to be produced in a homologous cell and/or a heterologous cell when compared to the cognate, wild-type regulator protein. In a particularly preferred embodiment, the variant regulator protein is a lovE variant regulator protein.

In a fifth aspect, the invention provides an isolated variant regulator protein of secondary metabolite production having increased activity compared to a cognate, wild-type protein, the variant regulator protein made by the process comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; (c) selecting a variant regulator protein with more activity than the cognate, wild-type protein; and (d) recovering the selected variant regulator protein.

In certain embodiments of the fifth aspect, the secondary metabolite is a fungal secondary metabolite. In certain embodiments of the fifth aspect, the protein regulator of secondary metabolite production is a transcription factor. In certain embodiments of the fifth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain embodiments of the fifth aspect, the variant regulator protein has more activity in a heterologous and/or a homologous cell than the cognate, wild-type protein. In certain embodiments of the fourth aspect, the variant regulator protein increases production of a secondary metabolite in a heterologous cell and/or a homologous cell when compared to the cognate, wild-type protein. In a particularly preferred embodiment, the variant regulator protein is a lovE variant regulator protein.

In a sixth aspect, the invention provides a fungus having improved lovastatin production made by the process of transforming a fungal cell with a nucleic acid molecule encoding a lovE variant protein of the first aspect of the invention. In an embodiment thereof, the nucleic acid molecule is selected from a nucleic acid molecule of the second aspect of the invention.

In a seventh aspect, the invention provides an improved process for making lovastatin comprising transforming a fungal cell with a nucleic acid molecule encoding a variant of the lovE protein of the first aspect of the invention. In an embodiment thereof, the fungal cell is transformed with a nucleic acid molecule of the second aspect of the invention.

In a eighth aspect, the invention provides a nucleic acid molecule encoding a lovE protein defined by SEQ ID NO:91. In an embodiment thereof, the invention provides an isolated lovE nucleic acid molecule defined by SEQ ID NO:92.

BRIEF DESCRIPTION OF THE DRAWINGS

FIG. 6 is a graphic presentation of lovastatin culture concentration, as measured by enzyme inhibition. assay, from broths of A. terreus cultures expressing lovE variant proteins 1–10 in.

DETAILED DESCRIPTION OF THE PREFERRED EMBODIMENTS

Figure 1:
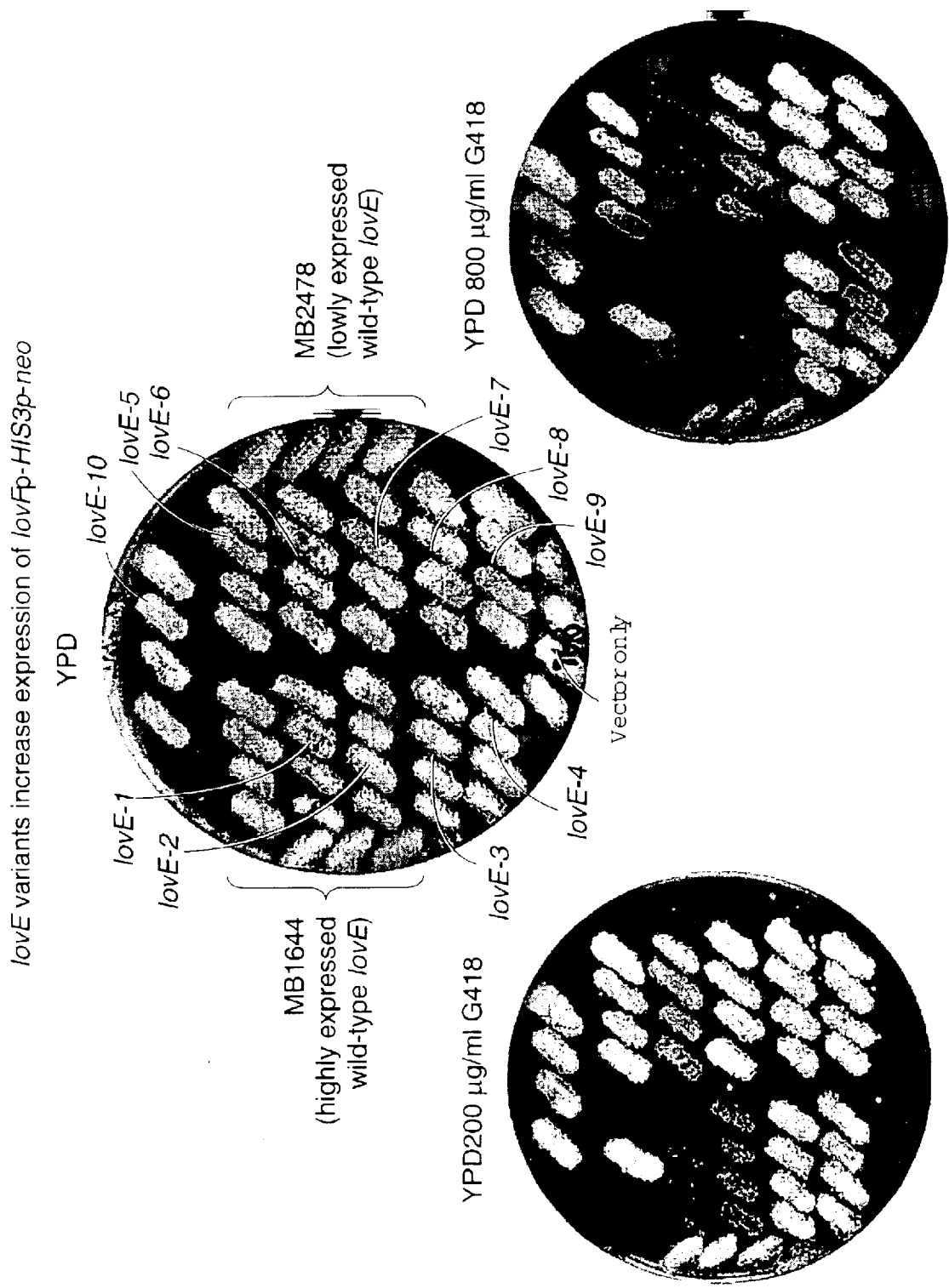
FIG. 1 is a photographic representation of cells growing on media with and without G418 selection demonstrating lovFp-HIS3p-Neo activation in S. cerevisiae. Controls include MB968 (vector only), MB2478 (lowly expressed wild-type lovE), and MB1644 (highly expressed wild-type lovE). All lovE variants are expressed in an MB968 vector backbone similar to MB2478.
Figure 2A:
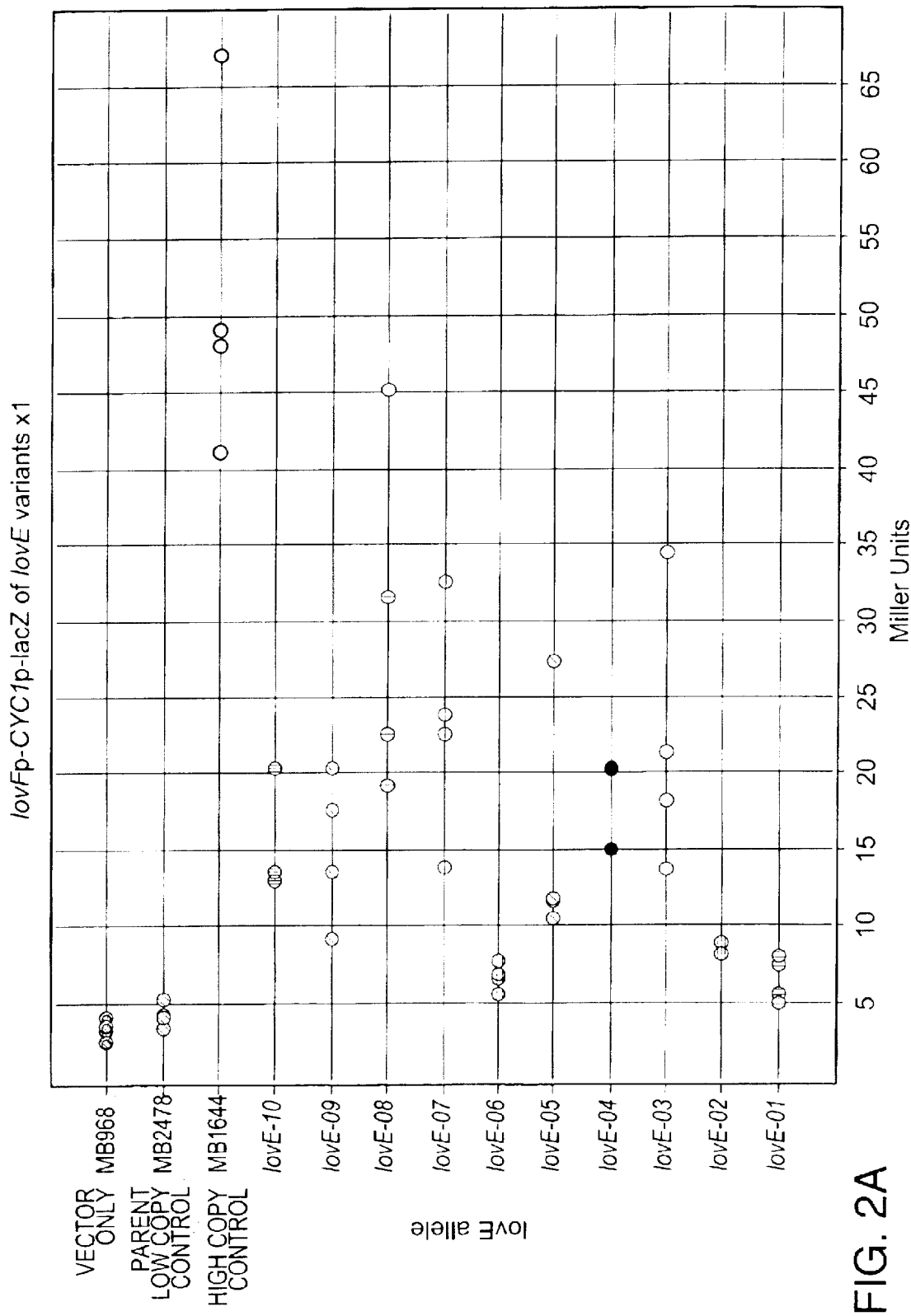
FIG. 2A is a graphic representation of lovFp-CYC1p-lacZ expression in S. cerevisiae strains expressing lovE variant proteins from the clones lovE 1–10.
Figure 2B:
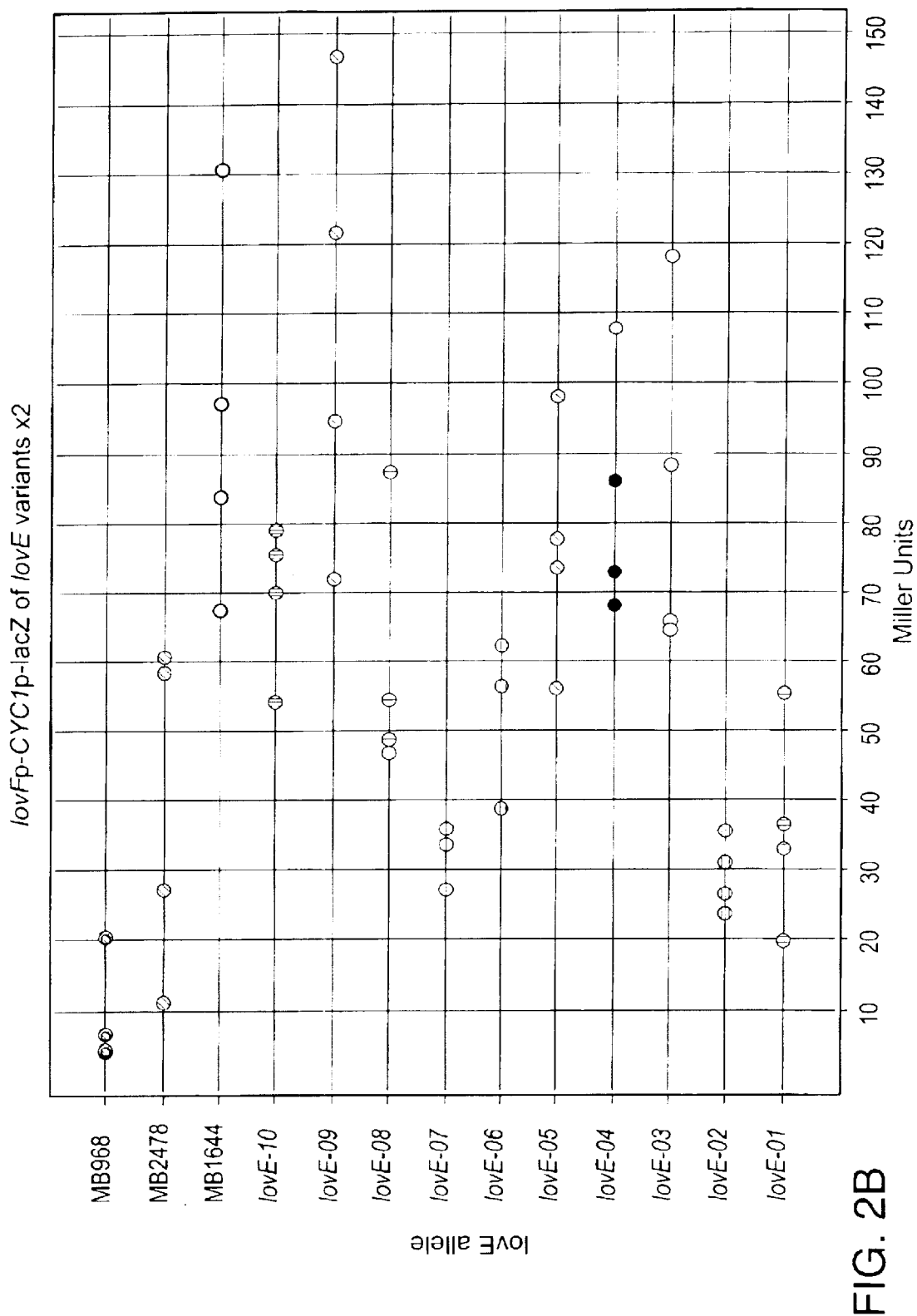
FIG. 2B is a graphic representation of lovFp-CYC1p-lacZ expression in S. cerevisiae strains expressing lovE variant proteins from the clones lovE 1–10 from a separate transformation than that of FIG. 2A.
Figure 3:
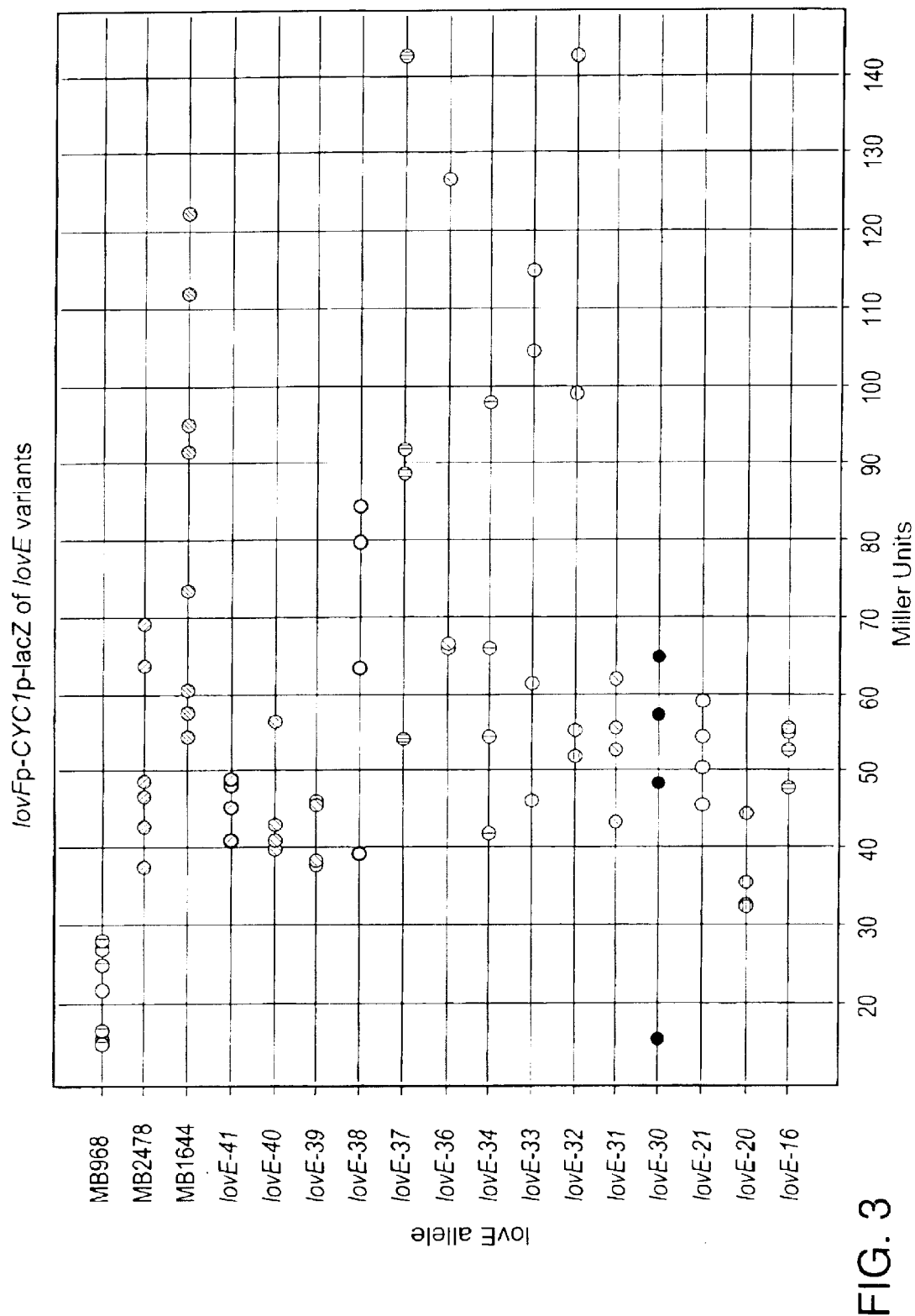
FIG. 3 is a graphic presentation of lovFp-CYC1p-lacZ expression in S. cerevisiae strains expressing lovE variant proteins from clones lovE 16–41.
Figure 4:
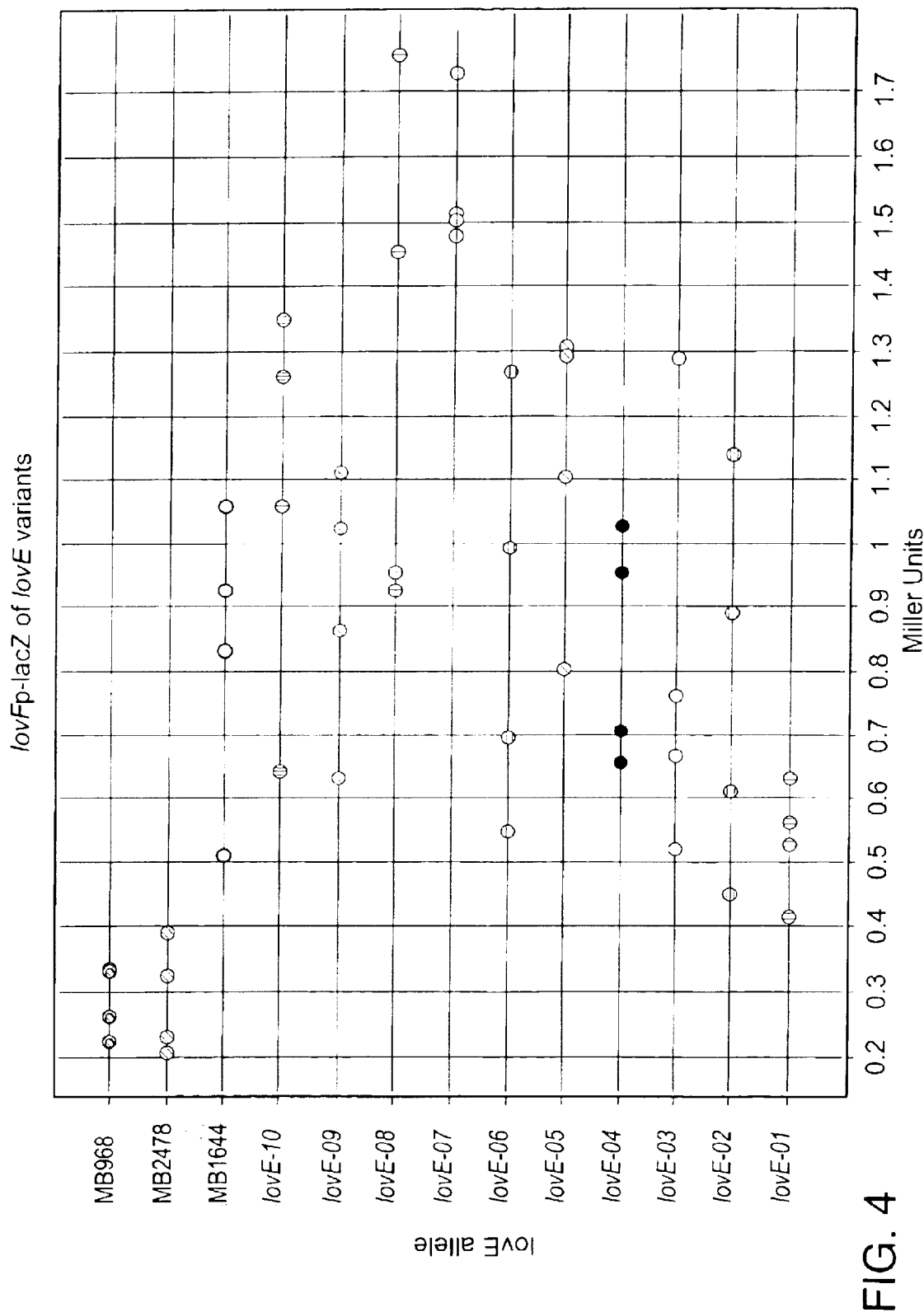
FIG. 4 is a graphic presentation of lovFp-lacz expression in S. cerevisiae strains expressing lovE variant proteins from clones lovE 1–10.
Figure 5:
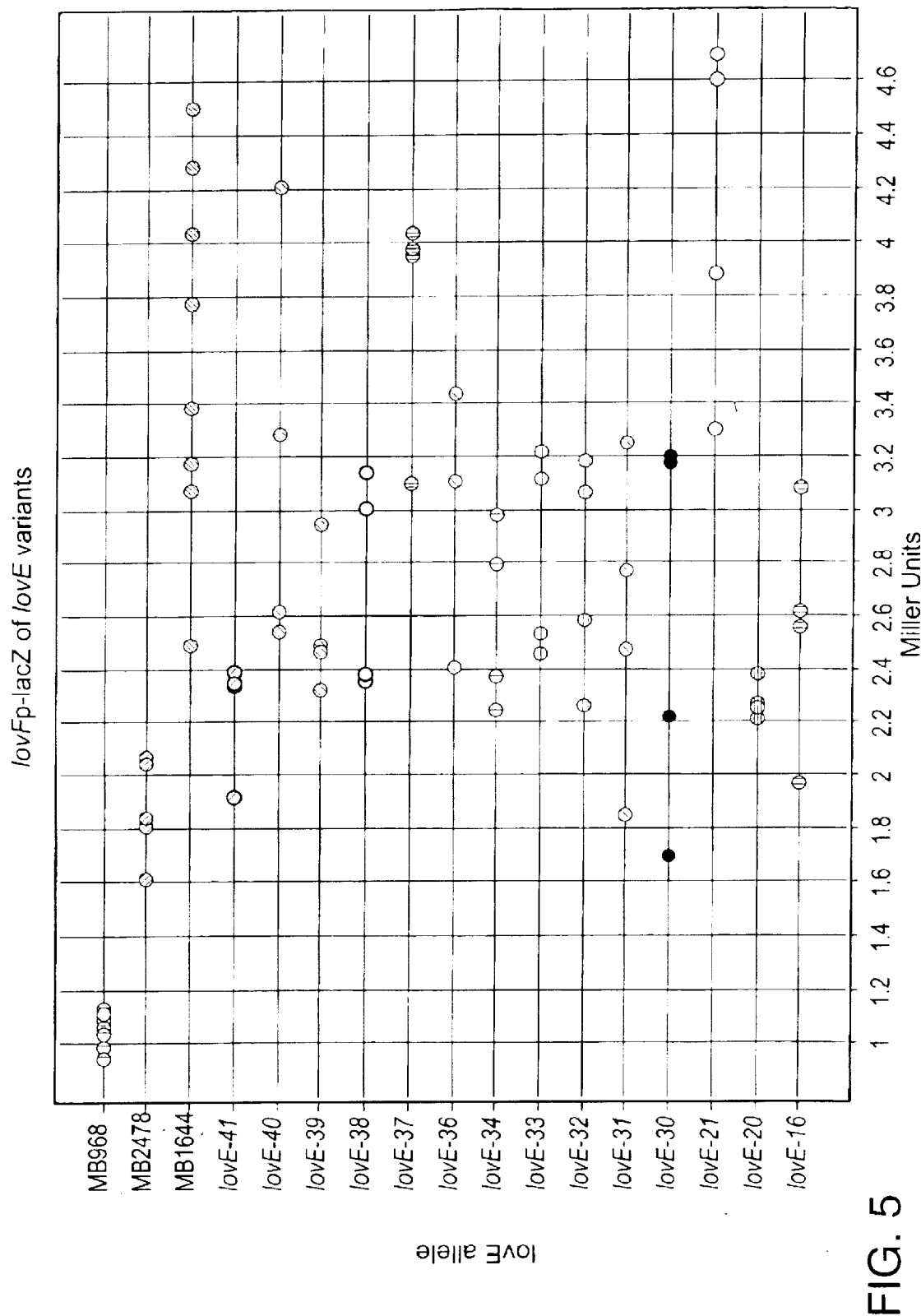
FIG. 5 is a graphic presentation of lovFp-lacZ expression in S. cerevisiae strains expressing lovE variant proteins from clones lovE 16, 20, 21, 30–34, and 36–41.

The patents and publications cited herein reflect the level of knowledge in the art and are hereby incorporated by reference in their entirety. Any conflict between any teaching of such references and this specification shall be resolved in favor of the latter.

The invention utilizes techniques and methods common to the fields of molecular biology, genetics and microbiology. Useful laboratory references for these types of methodologies are readily available to those skilled in the art. See, for example, *Molecular Cloning, A Laboratory Manual*, 3rd edition, edited by Sambrook, J., MacCallum, P., and Russell, D. W. (2001), Cold Spring Harbor Laboratory Press (ISBN: 0-879-69576-5); *Current Protocols In Molecular Biology*, edited by Ausubel, F. M., Brent, R., Kingston, R. E., Moore, D. D., Seidman, J. G., Struhl, K. (1993), John Wiley and Sons, Inc. (ISBN: 0-471-30661-4); *PCR Applications: Protocols for Functional Genomics*, edited by Innis, M. A., Gelfand, D. H., Sninsky, J. J. (1999), Cold Spring Harbor Press (ISBN: 0-123-72186-5); and *Methods In Yeast Genetics*, 2000 Edition: A Cold Spring Habor Laboratory Course Manual, by Burke, D., Dawson, D. and Stearns, T., Cold Spring Harbor Press (ISBN: 0-879-69588-9).

In certain embodiments of the aspects of the invention, the invention relates to the biosynthesis and improved production of secondary metabolites. The invention provides variant regulator proteins useful for the production of secondary metabolites, nucleic acid molecules encoding variant regulator proteins, and methods for their production.

In a first aspect, the invention provides a variant regulator protein of secondary metabolite production with increased activity relative to a cognate, wild-type regulator protein. Particularly preferred are variant regulator proteins of fungal secondary metabolites.

As used herein, the terms "fungal" and "fungus" refer generally to eukaryotic, heterotrophic organisms with an absorptive mode of nutrition. Fungi typically contain chitin in their cell walls and exhibit mycelial or yeast-like growth habits (*More Gene Manipulations in Fungi*, edited by J. W. Bennet and L. L. Lasure, Academic Press Inc. (1991), ISBN 0120886421). More specifically, the terms refer to secondary metabolite producing organisms including, without limitation, *Aspergillus* sp., *Penicillium* sp., *Acremonium chrysogenum*, *Yarrowia lipolytica*, *Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens*, *Ustilago maydis*, *Neurospora* sp., *Pestalotiopsis* sp.and *Phaffia rhodozyma* (See, *Fungal Physiology*, Chapter 9 (Secondary (Special) Metabolism), Griffin, D. H., John Wiley & Sons, Inc.; ISBN: 0471166154).

The term "variant regulator protein" is used herein to refer to any regulatory protein having at least one change or difference in the amino acid sequence of the protein when compared to its cognate, wild-type regulatory protein sequence. The term does not include naturally occurring allelic variations of the cognate, wild-type regulatory protein.

The term "regulator protein" is meant to refer to a protein having a positive or negative function that modifies the production of a secondary metabolite. The function of the protein may be at the level of transcription, e.g., repression or activation, protein synthesis, or transport. The regulator may alter the level of transcription, RNA stability, translation, post-translational modification, or cellular localization of proteins involved in secondary metabolite synthesis and/or transport. The regulator may also have effects on precursor metabolite pools, flux through specific pathways and metabolite resistance.

By way of non-limiting example, certain embodiments of the aspects of the invention relate to a regulator protein that is a protein that contributes and/or promotes transcription of a gene sequence, i.e., a transcription-activating protein.

"Transcription-activating" is a term used to refer to characteristics of a protein that promote transcription. As used herein, a transcription-activating protein would include proteins that increase accessibility of the DNA to transcription complexes, for example, by opening or relaxing chromatin structure, proteins that promote the recognition and/or binding of transcription complexes to a target gene sequence, and/or proteins that promote transcription complex movement along the length of the template DNA sequence.

Regulatory proteins of secondary metabolite production and the nucleic acid sequences encoding these are known to those skilled in the art. Non-limiting examples of regulatory proteins of secondary metabolite synthesis include: regulator proteins of the aflatoxin/sterigmatocystin biosynthetic cluster (Woloshuk, C. P., et al., *Appl, Environ. Microbial.* 60:2408–2414 (1994) and Brown, D. W., et al., *Proc Natl Acad Sci USA.* 93:1418–1422 (1996)); regulator proteins of the paxilline biosynthetic cluster (Young, C., et al., *Mol, Microbiol.* 39:754–764 (2001)); regulator proteins of the cephalosporin and penicillin biosynthetic clusters (Litzka O., et al., *Antonie Van Leeuwenhoek* 75:95–105 (1999); Schmitt E. K. and Kuck U., *J. Biol. Chem.* 275:9348–9357 (2000); MacCabe et al. *Mol. Gen. Genet.* 250:367–374 (1996); Suarez et al. *Mol. Microbiol.* 20:529–540 (1996); Lambert et al. *Mol. Cell. Biol.* 17:3966–3976 (1997); Su et al. *Genetics* 133:67–77 (1993); regulator proteins of tricothecene synthesis (Trapp S. C., et al., *Mol. Gen. Genet.* 257:421–432 (1998); Brown D. W., et al., *Fungal Genet. Biol.* 32:121–133 (2001); and Matsumoto G., et al. *Biosci. Biotechnol. Biochem.* 63:2001–2004 (1999)); and regulator proteins of lovastatin synthesis (Kennedy, J., et al., *Science* 284:1368–1372 (1999); Hendrickson et al., *Chem. Biol.* 6:429–439 (1999) Tag, A. et al., *Mol Microbiol.* 38:658–65 (2000)).

Certain embodiments of the aspects of the invention disclosed herein relate to the lovE regulator protein, a protein which plays a key role in the biosynthesis of lovastatin. More particularly, certain embodiments of the aspects of the invention relate to variant proteins of the lovE regulator protein and methods of making the same. Such proteins are variant with respect to the following *A. terreus* wild-type lovE sequences (SEQ ID NOS:91 and 92).

TABLE 1

Amino Acid and Nucleic Acid Sequences of Wild-type lovE

Wild-type lovE Amino Acid Sequence maadqgiftnsvtlspvegsrtggtlprrafrrscdrchaqkikctgnkevtgrapcqrc (SEQ ID NO:91)

qqaglrcvysercpkrklrqsraadlvsadpdpclhmssppvpsqslpldvseshssnts rqfldppdsydwswtsigtdeaidtdcwglsqcdggfscqleptlpdlpspfestvekap lppvssdiaraasaqrelfddlsavsqeleeillavtvewpkqeiwthpigmffnasrrl ltvlrqqaqadchqgtldeclrtknlftavhcyilnvriltaiselllsqirrtqnshms plegsrsqspsrddtsssghssvdtipffsenlpigelfsyvdplthalfsacttlhvg vqllreneitlgvhsaqgiaasismsgepgediartgatnsarceeqpttpaarvlfmfl sdegafqeaksagsrgrtiaalrrcyedifslarkhkhgmlrdlnnipp Wild-type lovE DNA Sequence atggctgcagatcaaggtatattcacgaactcggtcactctctcgccagtggagggttca (SEQ ID NO:92)

cgcaccggtggaacattacccgccgtgcattccgacgctcttgtgatcggtgtcatgca caaaagatcaaatgtactggaaataaggaggttactggccgtgctccctgtcagcgttgc cagcaggctggacttcgatgcgtctacagtgagcgatgccccaagcgcaagctacgccaa tccagggcagcggatctcgtctctgctgacccagatccctgcttgcacatgtcctcgcct ccagtgccctcacagagcttgccgctagacgtatccgagtcgcattcctcaaatacctcc cggcaatttcttgatccaccggacagctacgactggtcgtggacctcgattggcactgac gaggctattgacactgactgctgggggctgtcccaatgtgatggaggcttcagctgtcag ttagagccaacgctgccggatctaccttcgcccttcgagtctacggttgaaaaagctccg ttgccaccggtatcgagcgacattgctcgtgcggccagtgcgcaacgagagcttttcgat gacctgtcggcggtgtcgcaggaactggaagagatccttctggccgtgacggtagaatgg ccgaagcaggaaatctggacccatccaatcggaatgttttttcaatgcgtcacgacggctt cttactgtcctgcgccaacaagcgcaggccgactgccatcaaggcacactagacgaatgt ttacggaccaagaacctctttacggcagtacactgttacatattgaatgtgcggattttg accgccatatcggagttgctcctgtcgcaaattaggcggacccagaacagccatatgagc TABLE 1-continued Amino Acid and Nucleic Acid Sequences of Wild-type lovE

```
ccactggaagggagtcgatcccagtcgccgagcagagacgacaccagcagcagcagcggc cacagcagtgttgacaccataccctctcttagcgagaacctccctattggtgagctgttc tcctatgttgacccctgacacacgccctattctcggcttgcactacgttacatgttggg gtacaattgctgcgtgagaatgagattactctgggagtacactccgcccagggcattgca gcttccatcagcatgagcggggaaccaggcgaggatatagccaggacaggggcgaccaat tccgcaagatgcgaggagcagccgaccactccagcggctcgggttttgttcatgttcttg agtgatgaagggcttttcaggaggcaaagtctgctggttcccgaggtcgaaccatcgca gcactgcgacgatgctatgaggatatctttcctcgcccgcaaacacaaacatggcatg ctcagagacctcaacaatattcctccatga
```

As used herein, the term "secondary metabolite" means a compound, derived from primary metabolites, that is produced by an organism, is not a primary metabolite, is not ethanol or a fusel alcohol, and is not required for growth under standard conditions. Secondary metabolites are derived from intermediates of many pathways of primary metabolism. These pathways include, without limitation, pathways for biosynthesis of amino acids, the shikimic acid pathway for biosynthesis of aromatic amino acids, the polyketide biosynthetic pathway from acetyl coenzyme A (CoA), the mevalonic acid pathway from acetyl CoA, and pathways for biosynthesis of polysaccharides and peptidopolysaccharides. Collectively, secondary metabolism involves all primary pathways of carbon metabolism. Particularly preferred in embodiments of the aspects of the invention are fungal secondary metabolites (See, *Fungal Physiology*, Chapter 9 (Secondary(Special) Metabolism), Griffin, D. H., John Wiley & Sons, Inc.; ISBN: 0471166154).

"Secondary metabolite" also includes intermediate compounds in the biosynthetic pathway for a secondary metabolite that are dedicated to the pathway for synthesis of the secondary metabolite. "Dedicated to the pathway for synthesis of the secondary metabolite" means that once the intermediate is synthesized by the cell, the cell will not convert the intermediate to a primary metabolite. "Intermediate compounds" also include secondary metabolite intermediate compounds which can be converted to useful compounds by subsequent chemical conversion or subsequent biotransformation. As such, providing improved availability of such intermediate compounds would still lead to improved production of the ultimate useful compound, which itself may be referred to herein as a secondary metabolite. The yeast *Saccharomyces cerevisiae* is not known to produce secondary metabolites.

The term "primary metabolite" means a natural product that has an obvious role in the functioning of almost all organisms. Primary metabolites include, without limitation, compounds involved in the biosynthesis of lipids, carbohydrates, proteins, and nucleic acids. The term "increasing the yield of the secondary metabolite" means increasing the quantity of the secondary metabolite present in the total fermentation broth per unit volume of fermentation broth or culture.

As use herein, the phrase "modulate production of a secondary metabolite" refers to a positive or negative or desirable change in one or more of the variables or values that affect the process or results of production of the primary or secondary metabolites in a liquid or solid state fungal fermentation. These positive or negative or desirable changes include, without limitation, an increase or decrease in the amount of a primary or secondary metabolite being produced (in absolute terms or in quantity per unit volume of fermentation broth or per unit mass of solid substrate); a decrease in the volume of the broth or the mass/quantity of substrate required for the production of sufficient quantities; a decrease in the cost of raw materials and energy, the time of fermentor or culture run, or the amount of waste that must be processed after a fermentor run; an increase or decrease in the specific production of the desired metabolite (both in total amounts and as a fraction of all metabolites and side products made by the fungus); an increase or decrease in the percent of the produced secondary metabolite that can be recovered from the fermentation broth or culture; and an increase in the resistance of an organism producing a primary or secondary metabolite to possible deleterious effects of contact with the secondary metabolite.

In certain embodiments of aspects of the invention, a secondary metabolite is an anti-bacterial. An "anti-bacterial" is a molecule that has cytocidal or cytostatic activity against some or all bacteria. Preferred anti-bacterials include, without limitation, β-lactams. Preferred β-lactams include, without limitation, penicillins and cephalosporins and biosynthetic intermediates thereof. Preferred penicillins and biosynthetic intermediates include, without limitation, isopenicillin N, 6-aminopenicillanic acid (6-APA), penicillin G, penicillin N, and penicillin V. Preferred cephalosporins and biosynthetic intermediates include, without limitation, deacetoxycephalosporin V (DAOC V), deacetoxycephalosporin C (DAOC), deacetylcephalosporin C (DAC), 7-aminodeacetoxycephalosporanic acid (7-ADCA), cephalosporin C, 7-B-(5-carboxy-5-oxopentanamido)-cephalosporanic acid (keto-AD-7ACA), 7-B-(4-carboxybutanamido)-cephalosporanic acid (GL-7ACA), and 7-aminocephalosporanic acid (7ACA).

In certain embodiments of aspects of the invention, the secondary metabolite is an anti-hypercholesterolemic or a biosynthetic intermediate thereof. An "anti-hypercholesterolemic" is a drug administered to a patient diagnosed with elevated cholesterol levels for the purpose of lowering the cholesterol levels. Preferred anti-hypercholesterolemics include, without limitation, lovastatin, mevastatin, simvastatin, and pravastatin.

According to other embodiments of the invention, a secondary metabolite is an immunosuppressant or a biosynthetic intermediate thereof. An "immunosuppressant" is a molecule that reduces or eliminates an immune response in a host when the host is challenged with an immunogenic molecule, including immunogenic molecules present on transplanted organs, tissues or cells. Preferred immunosuppressants include, without limitation, members of the cyclosporin family and beauverolide L. Preferred cyclosporins include, without limitation, cyclosporin A and cyclosporin C.

In certain embodiments of aspects of the invention, the secondary metabolite is an ergot alkaloid or a biosynthetic intermediate thereof. An "ergot alkaloid" is a member of a large family of alkaloid compounds that are most often produced in the sclerotia of fungi of the genus Claviceps. An "alkaloid" is a small molecule that contains nitrogen and has basic pH characteristics. The classes of ergot alkaloids include clavine alkaloids, lysergic acids, lysergic acid amides, and ergot peptide alkaloids. Preferred ergot alkaloids include, without limitation, ergotamine, ergosine, ergocristine, ergocryptine, ergocornine, ergotaminine, ergosinine, ergocristinine, ergocryptinine, ergocorninine, ergonovine, ergometrinine, and ergoclavine.

In certain embodiments of aspects of the invention, the secondary metabolite is an inhibitor of angiogenesis or a biosynthetic intermediate thereof. An "angiogenesis inhibitor" is a molecule that decreases or prevents the formation of new blood vessels. Angiogenesis inhibitors have proven effective in the treatment of several human diseases including, without limitation, cancer, rheumatoid arthritis, and diabetic retinopathy. Preferred inhibitors of angiogenesis include, without limitation, fumagillin and ovalicin.

In certain embodiments of aspects of the invention, the secondary metabolite is a glucan synthase inhibitor or a biosynthetic intermediate thereof. A "glucan synthase inhibitor" is a molecule that decreases or inhibits the production of 1,3-β-D-glucan, a structural polymer of fungal cell walls. Glucan synthase inhibitors are a class of antifungal agents. Preferred glucan synthase inhibitors include, without limitation, echinocandin B, pneumocandin B, aculeacin A, and papulacandin.

In certain embodiments of aspects of the invention, the secondary metabolite is a member of the gliotoxin family of compounds or a biosynthetic intermediate thereof. The "gliotoxin family of compounds" are related molecules of the epipolythiodioxopiperazine class. Gliotoxins display diverse biological activities, including, without limitation, antimicrobial, antifungal, antiviral, and immunomodulating activities. Preferred members of the "gliotoxin family of compounds" include, without limitation, gliotoxin and aspirochlorine.

In certain embodiments of aspects of the invention, the secondary metabolite is a fungal toxin or a biosynthetic intermediate thereof. A "fungal toxin" is a compound that causes a pathological condition in a host, either plant or animal. Fungal toxins could be mycotoxins present in food products, toxins produced by phytopathogens, toxins from poisonous mushrooms, or toxins produced by zoopathogens. Preferred fungal toxins include, without limitation, aflatoxins, patulin, zearalenone, cytochalasin, griseofulvin, ergochrome, cercosporin, marticin, xanthocillin, coumarins, tricothecenes, fusidanes, sesterpenes, amatoxins, malformin A, phallotoxins, pentoxin, HC toxin, psilocybin, bufotenine, lysergic acid, sporodesmin, pulcheriminic acid, sordarins, fumonisins, ochratoxin A, and fusaric acid.

With some certain embodiments of aspects of the invention, the secondary metabolite is a modulator of cell surface receptor signaling or a biosynthetic intermediate thereof. The term "cell surface receptor" is as used before. Modulators of cell surface receptor signaling might function by one of several mechanisms including, without limitation, acting as agonists or antagonists, sequestering a molecule that interacts with a receptor such as a ligand, or stabilizing the interaction of a receptor and molecule with which it interacts. Preferred modulators of cell surface signaling include, without limitation, the insulin receptor agonist L-783,281 and the cholecystokinin receptor antagonist asperlicin.

In certain embodiments of aspects of the invention, the secondary metabolite is a plant growth regulator or a biosynthetic intermediate thereof. A "plant growth regulator" is a molecule that controls growth and development of a plant by affecting processes that include, without limitation, division, elongation, and differentiation of cells. Preferred plant growth regulators include, without limitation, cytokinin, auxin, gibberellin, abscisic acid, and ethylene.

In certain embodiments of aspects of the invention, the secondary metabolite is a pigment or a biosynthetic intermediate thereof. A "pigment" is a substance that imparts a characteristic color. Preferred pigments include, without limitation, melanins and carotenoids.

In certain embodiments of aspects of the invention, the secondary metabolite is an insecticide or a biosynthetic intermediate thereof. An "insecticide" is a molecule that is toxic to insects. Preferred insecticides include, without limitation, nodulisporic acid.

In certain embodiments of aspects of the invention, the secondary metabolite is an anti-neoplastic compound or a biosynthetic intermediate thereof. An "anti-neoplastic" compound is a molecule that prevents or reduces tumor formation. Preferred anti-neoplastic compounds include, without limitation, taxol (paclitaxel) and related taxoids.

The phrase "increased activity" is used herein to refer to a characteristic that results in an augmentation of the inherent negative or positive function of the regulatory protein.

The invention provides variant regulator proteins of secondary metabolite production with increased activity and methods of producing the same. The invention further provides for the identification of specific amino acid residues that are important to the functioning of secondary metabolite regulator proteins. By way of non-limiting example, variant regulator proteins of the secondary metabolite regulator lovE are presented herein.

As known to those skilled in the art, certain substitutions of one amino acid for another may be tolerated at one or more amino acid residues of a wild-type regulator protein absent a change in the structure, activity and/or function of the wild-type protein. Such substitutions are referred to in the art as "conservative" substitutions, and amino acids may be categorized into groups that identify which amino acids may be substituted for another without altering the structure and/or function of the protein.

As used herein, the term "conservative substitution" refers to the exchange of one amino acid for another in the same conservative substitution grouping in a protein sequence. Conservative amino acid substitutions are known in the art and are generally based on the relative similarity of the amino acid side-chain substituents, for example, their hydrophobicity, hydrophilicity, charge, size, and the like. In a preferred embodiment, conservative substitutions typically include substitutions within the following groups: Group 1:

glycine, alanine, and proline; Group 2: valine, isoleucine, leucine, and methionine; Group 3: aspartic acid, glutamic acid, asparagine, glutamine; Group 4: serine, threonine, and cysteine; Group 5: lysine, arginine, and histidine; Group 6: phenylalanine, tyrosine, and tryptophan. Each group provides a listing of amino acids that may be substituted in a protein sequence for any one of the other amino acids in that particular group.

As stated supra, there are several criteria used to establish groupings of amino acids for conservative substitution. For example, the importance of the hydropathic amino acid index in conferring interactive biological function on a protein is generally understood in the art (Kyte and Doolittle, *Mol. Biol.* 157:105–132 (1982). It is known that certain amino acids may be substituted for other amino acids having a similar hydropathic index or score and still retain a similar biological activity. Amino acid hydrophilicity is also used as a criteria for the establishment of conservative amino acid groupings (see, e.g., U.S. Pat. No. 4,554,101).

Information relating to the substitution of one amino acid for another is generally known in the art (see, e.g., *Introduction to Protein Architecture : The Structural Biology of Proteins*, Lesk, A. M., Oxford University Press; ISBN: 0198504748; *Introduction to Protein Structure*, Branden, C. -I., Tooze, J., Karolinska Institute, Stockholm, Sweden (Jan. 15, 1999); and *Protein Structure Prediction: Methods and Protocols (Methods in Molecular Biology)*, Webster, D. M.(Editor), August 2000, Humana Press, ISBN: 0896036375).

In one embodiment of the first aspect, the invention provides an improved regulator protein comprising an amino acid sequence coding for a variant of the lovE protein having at least one specific mutation that gives rise to greater transcription-activating properties of the regulator protein and/or increased lovastatin synthesis.

By way of non-limiting example, certain amino acid residues and mutations thereof in the lovE regulatory protein of *A. terreus* (SEQ ID NO:91) are identified by the invention described herein. Mutations at residues 31, 41, 52, 73, 101, 111, 133, 141, 153, 281, 367, and 389 of the wild-type lovE protein of *A. terreus* have been identified as being critical for the improvement of lovE regulator protein function. Those mutations include: F31L, Q41K, Q41R, T52I, T52N, C73R, P101S, P101Q, V111I, S133L, E141V, E141K, C153Y, C153R, T281A, N367I, N367Y, P389S and P389L. Each mutation, therefore, represents a change of one conservative class of amino acids for another. For example, the mutation F31L represents a change from a Group 6 amino acid residue to a Group 2 amino acid residue at position 31 of the wild-type, lovE regulator protein.

Thus, by way of non-limiting example, regulator proteins of this aspect of the invention include at least one of the following mutations: (1) a Group 6 amino acid residue mutated to a Group 2 amino acid residue at position 31, for example, the mutation represented by F31L;(2) a Group 3 amino acid residue mutated to a Group 5 amino acid residue at position 41, for example, the mutation represented by Q41K or Q41R; (3) a Group 4 amino acid residue mutated to a Group 2 amino acid residue at position 52, for example, the mutation represented by T52I; (4) a Group 4 amino acid residue mutated to a Group 3 amino acid residue at position 52, for example, the mutation represented by T52N; (5) a Group 4 amino acid residue mutated to a Group 5 amino acid residue at position 73, for example, the mutation represented by C73R; (6) a Group 1 amino acid residue mutated to a Group 4 amino acid residue at position 101, for example, the mutation represented by P101S; (7) a Group 1 amino acid residue mutated to a Group 3 amino acid residue at position 101, for example, the mutation represented by P101Q; (8) a valine amino acid residue mutated to another Group 2 amino acid residue at position 111, for example, the mutation represented by V111I; (9) a Group 4 amino acid residue mutated to a Group 2 amino acid residue at position 133, for example, the mutation represented by S133L; (10) a Group 3 amino acid residue mutated to a Group 2 amino acid residue at position 141, for example, the mutation represented by E141V; (11) a Group 3 amino acid residue mutated to a Group 5 amino acid residue at position 141, for example, the mutation represented by E141K; (12) a Group 4 amino acid residue mutated to Group 6 amino acid residue at position 153, for example, the mutation represented by C153Y; (13) a Group 4 amino acid residue mutated to a Group 5 amino acid residue at position 153, for example, the mutation represented by C153R; (14) a Group 4 amino acid residue mutated to a Group 1 amino acid residue at position 281, for example, the mutation represented by T281A; (15) a Group 3 amino acid residue mutated to a Group 2 amino acid residue at position 367, for example, the mutation represented by N367I; (16) a Group 3 amino acid residue mutated to a Group 6 amino acid residue at position 367, for example, the mutation represented by N367Y; (17) a Group 1 amino acid residue mutated to Group 4 amino acid residue at position 389, for example, the mutation represented by P389S; and/or (18) a Group 1 amino acid residue mutated to a Group 2 amino acid residue at position 389, for example, the mutation represented by P389L.

In other embodiments of the first aspect, the invention provides a variant of the lovE regulator protein with at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen of the above described specific mutations.

In other embodiments of the first aspect, the invention provides an isolated lovE variant regulator protein having the sequence of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, or SEQ ID NO:65.

In a second aspect, the invention provides a nucleic acid molecule encoding a variant regulator protein of secondary metabolite production of the first aspect of the invention. As used herein, the terms "nucleic acid" or "nucleic acid molecule" refer to a deoxyribonucleotide or ribonucleotide polymer in either single-or double-stranded form, and unless otherwise limited, would encompass analogs of natural nucleotides that can function in a similar manner as the naturally occurring nucleotide.

In one embodiment of the second aspect, the invention provides a nucleic acid molecule encoding a variant protein of the lovE regulator protein of the first aspect of the invention.

By way of non-limiting example, the invention provides a nucleic acid molecule encoding a lovE variant regulator protein having the sequence of SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:78, SEQ ID NO:79, SEQ ID NO:81, SEQ ID NO:82, SEQ ID NO:83, SEQ ID NO:84, SEQ ID NO:86, SEQ ID NO:87, SEQ ID NO:88, SEQ ID NO:89, or SEQ ID NO:90.

Poor transformation efficiency and the lack of efficient selection systems frequently precludes the screening of large numbers of variant regulator proteins of secondary metabolites in the organism from which the regulator protein is isolated. For example, there are currently certain technical obstacles to the successful screening of large numbers of variant regulator proteins in the fungus *A. terreus*, an organism that produces the secondary metabolite lovastatin.

The invention described herein takes advantage of the genetically tractable and experimentally amenable organism *Saccharomyces cerevisiae* for screening large numbers of variant regulator proteins of secondary metabolite production. Techniques common to the field of molecular biology are well developed in *S. cerevisiae*, and large numbers of vectors are available to assist the genetic manipulation and cloning of variant regulator proteins involved in secondary metabolite production. Other genetically tractable organisms could also be used for this purpose.

In a third aspect, the invention provides a method of increasing the activity of a protein that regulates secondary metabolite production comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; and (c) selecting a variant regulator protein with more activity than the cognate, wild-type protein.

As used herein, "mutating" is used to refer to the deliberate alteration of at least one nucleotide residue of a wild-type, cognate nucleic acid sequence encoding a regulator protein of secondary metabolite production. A deliberate alteration or change in at least one nucleotide residue of a polynucleotide may be accomplished by any method known in the art. The mutation(s) can be made in vivo or in vitro and can include random, partially random or not random, i.e., directed, mutagenesis techniques.

By way of non-limiting example, in vivo mutagenesis can be done by placing this nucleic acid molecule in a cell with a high mutation frequency, i.e. a mutagenic strain. By way of non-limiting example, Muhlrad et al. (*Yeast* 8:79–82 (1992)) have developed a rapid method for localized mutagenesis of yeast genes. As a first step, the region of interest of a gene sequence is first amplified in vitro under error-prone polymerase chain reaction (PCR) conditions. Error-prone polymerase chain reaction (PCR) is a method of introducing amino acid changes into proteins. With this technique, mutations are deliberately introduced during the PCR reaction through the use of error-prone DNA polymerases under specific reaction conditions. With the Muhlrad et al. procedure, the PCR product is then co-transformed with a gapped plasmid containing homology to both ends of the PCR product, resulting in in vivo recombination to repair the gap with the mutagenized DNA.

There are a variety of commercially available kits that may be used to produce mutant nucleic acid molecules by error-prone PCR (see, e.g., GeneMorph™ PCR Mutagenesis Kit (Stratagene, La Jolla, Calif.); and Diversify™ PCR Random Mutagenesis Kit (BD Biosciences Clontech, Palo Alto, Calif.). Thus, a plurality of variant, i.e., mutated, regulator proteins of secondary metabolite production may be produced using established mutagenesis techniques.

As used herein, the term "activity" refers to a characteristic of the regulator protein that negatively or positively affects the biological system to bring about a modulation in secondary metabolite production. By way of non-limiting example, the activity is the transcription of downstream genes involved in the biosynthetic pathway of the secondary metabolite of choice. Thus, in the present example, the phrase "more activity" refers to the property of a variant regulator protein to bring about more transcription than that effected by the cognate, wild-type regulator protein.

In certain embodiments of the third aspect, the selected variant regulator protein has more activity in a fungal cell than the cognate, wild-type protein. In certain embodiments of the third aspect, the protein regulator of secondary metabolite production is a transcription factor. In certain embodiments of the fourth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain other embodiments of the third aspect, the selected variant regulator protein has more activity in a heterologous cell than the cognate, wild-type protein. In certain embodiments thereof, the heterologous cell is an organism selected from the group consisting of *S. cerevisiae, E. coli, A. nidulans, Candida* sp., and *N. crassa*. In yet certain other embodiments of the third aspect, the selected variant regulator protein has more activity in a homologous cell than the cognate, wild-type protein. In certain embodiments thereof, the homologous cell is an organism selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

In certain embodiments of the third aspect, the selected variant regulator protein has more activity in a heterologous cell and a homologous cell than the cognate, wild-type protein. In certain embodiments thereof, the heterologous cell is an organism selected from the group consisting of *S. cerevisiae, E. coli, A. nidulans, Candida* sp., and *N. crassa* and the homologous cell is an organism selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp. and *Phaffia rhodozyma*.

As used herein, the phrase "heterologous cell" refers to a system for gene expression, i.e., an organism for gene expression, that is one other than the organism from which the selected regulator protein of secondary metabolite production has been isolated. Preferred heterologous cells include, but are not limited to, *S. cerevisiae, E. coli, A. nidulans*, and *Candida* sp., and *N. crassa*. Particularly preferred are fungal heterologous cells. In an embodiment of the third aspect, the method comprises: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; and (c) selecting a mutagenized nucleic acid encoding a variant regulator protein with increased activity in a homologous cell than the cognate, wild-type protein.

As used herein, the phrase "homologous cell" refers to a system for gene expression, i.e., an organism for gene expression, that is the organism from which the regulator protein of secondary metabolite production has been isolated. Preferred homologous cells are fungal homologous cells, including, but not limited to, *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp and *Phaffia rhodozyma*. (See, *Fungal Physiology*, Chapter 9 (Secondary(Special) Metabolism), Griffin, D. H., John Wiley & Sons, Inc.; ISBN: 0471166154).

In certain embodiments of the third aspect, the method further comprises selecting a variant regulator protein that also increases production of a secondary metabolite in a cell when compared to the cognate, wild-type protein. In certain embodiments thereof, the cell is a fungal cell. In certain embodiments thereof, the cell is a heterologous cell, preferably selected from the group consisting of *S. cerevisiae, E. coli, A. nidulans, Candida* sp., and *N. crassa*.

In certain embodiments thereof, the cell is a homologous cell, preferably selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp.. *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

Certain embodiments of the aspects of the invention relate to regulator proteins that promote secondary metabolite production by increasing transcription of one or more genes involved with secondary metabolite production. These wild-type sequences may be selected for mutagenesis to create a plurality of variant regulator proteins. The activity of these transcription-activating variant regulator proteins may be determined by measuring the activity of a reporter gene having the appropriate promoter sequences. These tests are done in a homologous and/or a heterologous cell. Certain embodiments of aspects of the invention are directed to fungal regulator proteins with transcription-activating activity that is tested in fungal heterologous and homologous cells.

Reporter genes are useful for isolating transformants expressing improved variant regulator proteins. The reporter genes may be operably linked to a promoter sequence that is normally regulated by the wild-type regulator protein. Reporter genes include, but are not limited to, genes encoding β-galactosidase (lacZ), β-glucoronidase (GUS), β-glucosidase, amylase and invertase, amino acid biosynthetic genes, e.g., the yeast LEU2, HIS3, LYS2, TRP1 genes (or homologous genes from other fungi, such as filamentous fungi, that encode proteins with the similar functional activities), nucleic acid biosynthetic genes, e.g., the yeast URA3 and ADE2 genes (or homologous genes from other fungi, such as filamentous fungi, that encode proteins with the similar functional activities), the mammalian chloramphenicol transacetylase (CAT) gene, or any surface antigen gene for which specific antibodies are available. A reporter gene can also be a neomycin phosphotransferase(neo) gene, which encodes neomycin, kanamycin resistance gene and G418 (geneticin) resistance gene. A reporter gene may encode a protein detectable by luminescence or fluorescence, such as green fluorescent protein (GFP). Reporter genes may additionally or alternatively encode any protein that provides a phenotypic marker, for example, a protein that is necessary for cell growth or viability, or a toxic protein that causes cell death. Alternatively, the reporter gene may encode a protein detectable by a color assay leading to the presence or absence of color.

The choice of reporter gene will depend on the type of cell to be transformed. Preferred reporter genes are those that are operable in fungal cells. It is preferable to have two reporter genes within the cell. One reporter gene, when expressed, provides a growth advantage to transformed cells that are expressing the variant regulator protein. This allows for the isolation of such transformants though selective pressures. The other reporter gene provides a colorimetric marker, such as the lacZ gene and its encoded protein, β-galactosidase. Alternatively, the second reporter provides a fluorescent or luminescent marker, such as green fluorescent protein (GFP).

In a fourth aspect, the invention provides a method of increasing production of a secondary metabolite comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; (c) selecting a variant regulator protein with more activity than the cognate, wild-type protein; and (d) expressing the selected variant regulator protein in a cell, thereby increasing production of the secondary metabolite in the cell.

In certain embodiments of the fourth aspect, the cell is a fungal cell. In certain embodiments of the fourth aspect, the protein regulator of secondary metabolite production is a transcription factor. In certain embodiments of the fourth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain embodiments of the fourth aspect, the cell is a heterologous cell, preferably selected from the group consisting of *S. cerevisiae, E. coli, A. nidulans, Candida* sp., and *N. crassa*. In certain other embodiments of the fourth aspect, the cell is a homologous cell, preferably selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

In certain other embodiments of the fourth aspect, the cell is a heterologous cell and the method further comprises expressing the variant regulator protein in a homologous cell, thereby increasing secondary metabolite production in the homologous cell. In certain embodiments thereof, the heterologous cell is an organism selected from the group consisting of *S. cerevisiae, E. coli, A. nidulans, Candida* sp., , and *N. crassa* and the homologous cell is an organism selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp. and *Phaffia rhodozyma*.

In a fifth aspect, the invention provides an isolated variant regulator protein of secondary metabolite production having increased activity compared to a cognate, wild-type protein, made by the process comprising: (a) selecting a nucleic acid comprising a polynucleotide encoding a protein regulator of secondary metabolite production; (b) mutating the nucleic acid to create a plurality of nucleic acid molecules encoding variant regulator proteins of secondary metabolite production; (c) selecting a variant regulator protein with more activity than the cognate, wild-type protein; and (d) recovering the selected variant regulator protein.

In certain embodiments of the fifth aspect, the variant regulator protein selected has more activity in a fungal cell. In certain embodiments of the fifth aspect, the protein regulator of secondary metabolite production is a transcription factor. In certain embodiments of the fifth aspect, the protein regulator of secondary metabolite production is a transmembrane transporter, a protein that mediates secretion, a kinase, a G-protein, a cell surface receptor, a GTPase activating protein, a guanine nucleotide exchange factor, a phosphatase, a protease, a phosphodiesterase, a bacterial protein toxin, an importin, an RNA-binding protein, an SCF complex component, an adherin, or a protein encoded within a biosynthetic cluster. In certain embodiments of the fifth aspect, the variant regulator protein selected has more activity in a heterologous cell, preferably selected from the group consisting of *S. cerevisiae, E. coli, A. nidulans, Candida* sp., *Neurospora* sp., *Pestalotiopsis* sp., and *N. crassa*. In certain embodiments of the fifth aspect, the variant regulator protein selected has more activity in a homologous cell, preferably selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

In certain embodiments of the fifth aspect, the variant regulator protein selected has more activity in a homologous cell and a heterologous cell. In embodiments thereof, the heterologous cell is an organism selected from the group consisting of *S. cerevisiae, E. coli, A. nidulans, Candida* sp., *Neurospora* sp., *Pestalotiopsis* sp., and *N. crassa* and the homologous cell is an organism selected from the group consisting of *Aspergillus* sp., *Penicillium* sp., *Acremonium chrysogenum, Yarrowia lipolytica, Nodulisporium* sp., *Fusarium* sp., *Monascus* sp., *Claviceps* sp., *Trichoderma* sp., *Tolypocladium* sp., *Tricotheicium* sp., *Fusidium* sp., *Emericellopsis* sp., *Cephalosporium* sp., *Cochliobolus* sp., *Helminthosporium* sp., *Agaricus brunescens, Ustilago maydis, Neurospora* sp., *Pestalotiopsis* sp., and *Phaffia rhodozyma*.

In yet another embodiment of the fifth aspect, the variant regulator protein is a variant protein of the lovE protein having at least one of the following mutations: (1) a Group 6 amino acid residue mutated to a Group 2 amino acid residue at position 31, for example, the mutation represented by F31L;(2) a Group 3 amino acid residue mutated to a Group 5 amino acid residue at position 41, for example, the mutation represented by Q41K or Q41R; (3) a Group 4 amino acid residue mutated to a Group 2 amino acid residue at position 52, for example, the mutation represented by T52I; (4) a Group 4 amino acid residue mutated to a Group 3 amino acid residue at position 52, for example, the mutation represented by T52N; (5) a Group 4 amino acid residue mutated to a Group 5 amino acid residue at position 73, for example, the mutation represented by C73R; (6) a Group 1 amino acid residue mutated to a Group 4 amino acid residue at position 101, for example, the mutation represented by P101S; (7) a Group 1 amino acid residue mutated to a Group 3 amino acid residue at position 101, for example, the mutation represented by P101Q; (8) a valine amino acid residue mutated to another Group 2 amino acid residue at position 111, for example, the mutation represented by V111I; (9) a Group 4 amino acid residue mutated to a Group 2 amino acid residue at position 133, for example, the mutation represented by S133L; (10) a Group 3 amino acid residue mutated to a Group 2 amino acid residue at position 141, for example, the mutation represented by E141V; (11) a Group 3 amino acid residue mutated to a Group 5 amino acid residue at position 141, for example, the mutation represented by E141K; (12) a Group 4 amino acid residue mutated to Group 6 amino acid residue at position 153, for example, the mutation represented by C153Y; (13) a Group 4 amino acid residue mutated to a Group 5 amino acid residue at position 153, for example, the mutation represented by C153R; (14) a Group 4 amino acid residue mutated to a Group 1 amino acid residue at position 281, for example, the mutation represented by T281A; (15) a Group 3 amino acid residue mutated to a Group 2 amino acid residue at position 367, for example, the mutation represented by N367I; (16) a Group 3 amino acid residue mutated to a Group 6 amino acid residue at position 367, for example, the mutation represented by N367Y; (17) a Group 1 amino acid residue mutated to Group 4 amino acid residue at position 389, for example, the mutation represented by P389S; and/or (18) a Group 1 amino acid residue mutated to a Group 2 amino acid residue at position 389, for example, the mutation represented by P389L.

In certain embodiments of this aspect of the invention, the variant protein of the lovE protein sequence has an amino acid sequence of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, or SEQ ID NO:65.

In another embodiment thereof, the variant protein of the lovE protein is encoded by a nucleic acid molecule having a polynucleotide sequence of SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:78, SEQ ID NO:79, SEQ ID NO:81, SEQ ID NO:82, SEQ ID NO:83, SEQ ID NO:84, SEQ ID NO:86, SEQ ID NO:87, SEQ ID NO:88, SEQ ID NO:89, or SEQ ID NO:90.

In a sixth aspect, the invention provides a fungus having improved lovastatin production made by the process of transforming a fungal cell with a nucleic acid molecule encoding a variant of the lovE protein of the first aspect of the invention. In an embodiment thereof, the nucleic acid molecule is selected from a nucleic acid molecule of the second aspect of the invention.

In a seventh aspect, the invention provides an improved process for making lovastatin comprising transforming a fungal cell with a nucleic acid molecule encoding a variant of the lovE protein of the first aspect of the invention. In an embodiment thereof, the fungal cell is transformed with a nucleic acid molecule of the second aspect of the invention.

International patent application PCT/US99/29583 discloses lovastatin production genes. However, this reference does not provide a mature lovE cDNA sequence. The invention herein remedies the shortcoming of this reference by providing a complete cDNA sequence for the lovE mRNA.

In an eighth aspect, the invention provides a nucleic acid molecule encoding a lovE protein defined by SEQ ID NO:91. In an embodiment thereof, the invention provides an isolated lovE nucleic acid molecule defined by SEQ ID NO:92.

The following examples illustrate the preferred modes of making and practicing the present invention but are not meant to limit the scope of the invention since alternative methods may be utilized to obtain similar results.

EXAMPLES

Example 1: Preparation of Strains and Plasmids

Strain MY2124 was derived from the Sigma 1278b strain background of S. cerevisiae and its complete genotype is as follows: MATα/MATα::LEU2 ura3Δ0 /ura3Δ0 leu2Δ0/ leu2Δ0 trp1Δ0::hisG/trp1Δ0::hisG his3Δ0::hisG/ his3Δ0::hisG ura3Δ0::lovF-HIS3p-neo/ura3Δ0. MY2124 can be constructed by mating S. cerevisiae strains MY2112 (MATα ura3Δ0 leu2Δ0trp1Δ0::hisG his3Δ0::hisG ura3Δ0::lovFp-HIS3p-neo) with MY1555 (matα::LEU2 ura3Δ0 leu2Δ0 trp1Δ0::hisG his3Δ0::hisG) and isolating zygotes. The ura3Δ0::lovFp-HIS3p-neo allele of MY2112 was derived by cotransforming SfiI-linearized plasmid MB2254 with pRS424 (Sikorski and Hieter (1989) *Genetics* 122:19–27) into MY1413 (MATα leu2Δ0 trp1Δ0::hisG his3Δ0::hisG). Transformants were selected on SC-Trp media and subsequently screened for 5-fluoro-orotic acid resistance to identify those transformants containing the ura3Δ0::lovFp-HIS3p-neo allele. Trp segregants lacking plasmid pRS424 were isolated by growing the strain under non-selective conditions.

The following oligonucleotides were used in the construction of plasmids.

TABLE 2

Oligonucleotides Utilized For LovE Variant Cloning

| | | |
|---|---|---|
| MO664 | (5'GGCCATGGAGGCCGCTAGCTCGAGTCGACGGCCTAGGTGGCCAGCT3') | (SEQ ID NO:1) |
| MO665 | (5'GGCCACCTAGGCCGTCGACTCGAGCTAGCGGCCTCCATGGCCGTAC3') | (SEQ ID NO:2) |
| MO666 | (5'GGCGGCCGCTCTAGAACTAGTCTCGAGGGTACC3') | (SEQ ID NO:3) |
| MO667 | (5'GGTACCCTCGAGACTAGTTCTAGAGCGGCCGCC3') | (SEQ ID NO:4) |
| MO1794 | (5'CACAGCGGCCGCTCAACCTTCCCATTGGGGC3') | (SEQ ID NO:5) |
| MO1793 | (5'CACCACTAGTACGCGGGCTGATTCGAC3') | (SEQ ID NO:6) |
| MO1785 | (5'CACCACTAGTTATACATTATATAAAGTAATGTG3') | (SEQ ID NO:7) |
| MO1786 | (5'CACAGGATCCGTCATCTTTGCCTTCGTTTATC3') | (SEQ ID NO:8) |
| MO195 | (5'CGCGGATCCTATTGAACAAGATGGATTGCAC3') | (SEQ ID NO:9) |
| MO196 | (5'CCGGAATTCAGAAGAACTCGTCAAGAAG3') | (SEQ ID NO:10) |
| MO841 | (5'ACAAAAAAGCAGGCTCCACAATGGCTGCAGATCAAGGTAT3') | (SEQ ID NO:11) |
| MO842 | (5'ACAAGAAAGCTGGGTTCATGGAGGAATATTGTTGA3') | (SEQ ID NO:12) |
| MO2278 | (5'GGGGATCCAATCGAGGTCCACGACCAGT3') | (SEQ ID NO:13) |
| MO343 | (5'GGGGACAAGTTTGTACAAAAAAGCAGGCT3') | (SEQ ID NO:14) |
| MO2273 | (5'GGGGATCCGCCAATGGTCCCGTTCAAAC3') | (SEQ ID NO:15) |
| MO2274 | (5'ACAAGAAAGCTGGGTTCACAGAATGTTTAGCTCAA3') | (SEQ ID NO:16) |
| MO344 | (5'GGGGACCACTTTGTACAAGAAAGCTGGGT3') | (SEQ ID NO:17) |
| MO2624 | (5'GCGATGCCCCAAGCGCAAGCTACGCCAATCCAGGG3') | (SEQ ID NO:18) |
| MO2654 | (5'CGTCGCGCCATTCGCCATTCAGGCTGCGCAACTGT3') | (SEQ ID NO:19) |
| MO2680 | (5'GGACCTTTGCAGCATAAATTACTATACTTCT3') | (SEQ ID NO:20) |
| MO2686 | (5'GGCGCGTCCATTCGCCATTCAGGCTGCGCAACTGT3') | (SEQ ID NO:21) |
| MO2681 | (5'TAAAACTCTTGTTTTCTTCTTTTCTCTAAAT3') | (SEQ ID NO:22) |
| MO2700 | (5'CAGTGAGCGCGCGTAATACGACTCACTATAGGGCGA3') | (SEQ ID NO:23) |
| MO2701 | (5'ATACTTCTATAGACACACAAACACAAATACACACAC3') | (SEQ ID NO:24) |
| MO107 | (5'CGCGGATCCCGTCGTTTTACAAC3') | (SEQ ID NO:25) |
| MO197 | (5'CCCAAGCTTATTATTTTTGACACCAGACCAA3') | (SEQ ID NO:26) |

TABLE 2-continued

Oligonucleotides Utilized For LovE Variant Cloning

| | | |
|---|---|---|
| MO1293 | (5'GGAAGATCTAGCATCGTGGCCAATTTCTTCTAGTTT3') | (SEQ ID NO:27) |
| MO1294 | (5'ATAAGAATGCGGCCGCTCAACCTTCCCATTGGGGCGTTTGC3') | (SEQ ID NO:28) |
| MO1787 | (5'CACAGGATCCAGCATTATTAATTTAGTGTGTGTATTT3') | (SEQ ID NO:29) |
| MO1788 | (5'CACCACTAGTCTCGAGCAGATCCGCCAG3') | (SEQ ID NO:30) |
| MO1793 | (5'CACCACTAGTACGCGGGCTGATTCGAC3') | (SEQ ID NO:31) |
| MO1794 | (5'CACAGCGGCCGCTCAACCTTCCCATTGGGGC3') | (SEQ ID NO:32) |
| MO511 | (5'GGCCATCGATACAAGTTTGTACAAAAAAGCTGAAC3') | (SEQ ID NO:33) |
| MO540 | (5'GGCGCCCTATTACACCACTTTGTACAAGAAAGC3') | (SEQ ID NO:34) |
| MO1985 | (5'CACACGTCTCCGGCCTCAACCTTCCCATTGGGGCG3') | (SEQ ID NO:35) |
| MO1986 | (5'CACACAGATCTCGTGGCCAATTTCTTCTAGTTTGA3') | (SEQ ID NO:36) |
| MO1992 | (5'CACACGGATCCACAATGTTACGTCCTGTAGAAACCCC3') | (SEQ ID NO:37) |
| MO1993 | (5'CACAGCGGCCGCTTCATTGTTTGCCTCCCTGCTG3') | (SEQ ID NO:38) |
| MO316 | (5'GCGGCCGCGGCGCCCGGCCCATGTCAACAAGAAT3') | (SEQ ID NO:39) |
| MO318 | (5'CCGCGGCCGAGTGGAGATGTGGAGT3') | (SEQ ID NO:40) |

Plasmid MB2254 contains the lovFp-HIS3p-neo reporter gene flanked by URA3 sequence. First primers MO664 (SEQ ID NO:1) and MO665 (SEQ ID NO:2) were annealed and inserted into the KpnI-SacI sites of plasmid pBluescript II KS (Stratagene,). The resulting vector, MB1038, contains a SalI site in the polylinker. Next, the SpeI-XhoI fragment from pJL164 (Brachmann et al. *Yeast* 14:115–132 (1998)) containing a deletion of the URA3 gene with additional flanking sequences was inserted into the NheI-SalI sites of MB1038 to create MB1053. Primers MO666 (SEQ ID NO:3) and MO667 (SEQ ID NO:4) that contain multiple restriction sites (NotI, XbaI, SpeI, XhoI and KpnI) were then annealed together and ligated into the SmaI site of MB1053 to create MB1054. Next, the following four fragments were combined in MB1054 to obtain plasmid MB2254. The lovF promoter from *A. terreus* genomic DNA was PCR amplified with MO1794 (SEQ ID NO:5) and MO1793 (SEQ ID NO:6) and inserted into MB1054 on a NotI-SpeI fragment. The HIS3 basal promoter from pRS403 (Sikorski and Hieter, *Genetics* 122:19–27 (1989)) was PCR amplified with primers MO1785 (SEQ ID NO:7) and MO1786 (SEQ ID NO:8) and inserted into MB1054 on a SpeI-BamHI fragment. Finally, the neo gene (PCR amplified with MO195 (BamHI) (SEQ ID NO:) and MO196 (EcoRI) (SEQ ID NO:10) from plasmid pYX11 (Xiao and Weaver, *Nucl. Acids Res.* 25:2985–2991 (1997)) and CYC1 terminator sequences (XhoI-KpnI fragment from pRS426-GAL-S (Mumberg, et al., *Nucl. Acids. Res.* 22:5767–5768 (1994)) were first combined in pRS416 (Sikorski and Hieter, *Genetics* 122:19–27 (1989)) and then cut out with BamHI-KpnI and inserted into MB1054 to create MB2254.

The lovFp-HIS3p-neo reporter in MY2124 can confer resistance to the drug geneticin (G418). It was empirically determined that MY2124 (untransformed or transformed with parental plasmids MB2478 (CYC1-lovE/CEN) or MB2848 (CYC1-lovE/At274/CEN) was unable to grow on YPD media supplemented with 100 µg/ml G418. Plasmid MB2478 contains the CYC1 promoter operationally linked to the entire *A. terreus* lovE open reading frame. The CYC1 promoter is a relatively weak promoter and thus the lovE ORF in MB2478 was expressed at low levels. MB2478 was the parental vector plasmid for creating full length lovE variants. Plasmid MB2848 contains the CYC1 promoter operationally linked to a chimeric open reading frame consisting of the *A. terreus* lovE DNA binding domain fused to the carboxy-terminal portion of the At274 gene (U.S. Ser. No. 60/257,431, filed Dec. 22, 2000).

MB2848 was used to create lovE variants in which the DNA binding domain was not mutated. Both MB2478 and MB2848 contain yeast CEN and autonomously replicating sequences and both are maintained at 1–2 copies per cell. In contrast to strains transformed with MB2478 or MB2848, strains transformed with plasmid MB1644 (TEF1-lovE/2 micron) were able to grow on G418-supplemented YPD media. The lovE gene of MB1644 is under control of the constitutively strong *S. cerevisiae* TEF1 promoter. MB1644 contains a 2-micron origin for high-copy replication in yeast. An objective of these studies was to identify lovE variants which when expressed at low levels could confer G418 resistance similar to the highly expressed wild-type lovE molecule of MB1644. *S. cerevisiae* expression vectors used in these studies were constructed as follows.

MB968 is a low copy *S. cerevisiae* URA3 based expression vector. MB968 was created by inserting the EcoRV fragment (containing the destination cassette) from gateway pEZC7201 (Invitrogen™, Carlsbad, Calif.) into XhoI/SalI (filled in with Klenow) linearized pRS416 CYC1 (Mumberg, et al., *Gene* 156:119–122 (1995)).

MB1644 and MB2478 are URA3-based *S. cerevisiae* expression plasmids that contain the wild-type lovE gene. They are both derivatives of MB1199. MB1199 was created by using primers MO841 (SEQ ID NO:11) and MO842 (SEQ ID NO:12) to amplify the lovE ORF from *A. terreus* cDNA. Gateway (Invitrogen™, Carlsbad, Calif.) Cloning Technology (U.S. Pat. No. 5,888,732) was used to clone the lovE PCR fragment into the gateway entry vector pDONR206 (Invitrogen™, Carlsbad, Calif.) to create MB1199. Similarly, Gateway Cloning Technology was used to transfer the lovE ORF from MB1199 into MB968 to create MB2478 and into MB969 (U.S. Ser. No. 60/198,335, filed Apr. 18, 2000) to create MB1644.

MB2848 is a derivative of MB968 that contains a lovE-AT274 chimera. The lovE portion of MB2848 was derived by using oligos MO841 (SEQ ID NO:11) and MO2278 (SEQ ID NO:13) to PCR amplify the lovE DNA binding domain from *A. terreus* cDNA. A second round of PCR was performed with primers MO343 (SEQ ID NO:14) and MO2278 to add appropriate Gateway Cloning Technology compatible sequences. The At274 portion of MB2848 can be derived by using primers MO2273 (SEQ ID NO:15) and MO2274 (SEQ ID NO:16) to PCR amplify the carboxy-terminal domain of At274 from *A. terreus* cDNA. A second round of PCR was performed with primers MO344 (SEQ ID NO:17) and MO2273 to add appropriate Gateway Cloning Technology compatible sequences. The lovE and At274 PCR products were cut with BamHI and purified over a QIAquick PCR purification kit (Qiagen, Valencia, Calif.) according to manufacturer's instructions. Finally, the products were mixed 3-4 hours in a standard ligation reaction and used in Gateway entry and destination reactions to create MB2848.

Gateway cloning technology was used to clone the lovE variants of interest into plasmid MB1419 which is a filamentous fungal expression vector. The MB1419 fungal selection marker is the *A. nidulans* GPD promoter controlling the ble gene from *S. hindustanus*. The transgene is controlled by the *A. nidulans* PGK promoter. *A. terreus* strain MF117 is a derivative of *A. terreus* strain ATCC 20542.

Example 2: PCR Mutagenesis of the lovE DNA Binding Domain

The zinc finger DNA binding domain of lovE is encoded by nucleotides 100–201 (SEQ ID NO:92). Oligos MO2624 (SEQ ID NO:18) and MO2654 (SEQ ID NO:19) were used to PCR amplify a lovE containing fragment from plasmid MB2478. The 1.7 kb product contains nucleotides 212–1410 of lovE and ~500 bp of flanking vector sequence. Two rounds of standard PCR (1.5 mM MgCl$_2$) were performed with Amplitaq DNA polymerase (Applied Biosystems, Foster City, Calif.) according to the manufacturer's instructions.

Plasmid MB2848 was cut with KpnI-BamHI to release a 1.1 kb fragment containing the At274 portion of the lovE-At274 chimeric open reading frame. The remaining 5.5 kb vector sequence retains the lovE DNA binding domain.

Example 3: PCR Mutagenesis of the lovE Open Reading Frame lovE open reading frame insert was prepared according to the following procedure. Oligo pairs MO2680 (SEQ ID NO:20) /MO2686 (SEQ ID NO:21), MO2681 (SEQ ID NO:22) /MO2686, and MO2700 (SEQ ID NO:23) /MO2701 (SEQ ID NO:24) were used to PCR amplify the entire lovE open reading frame from plasmid MB2478. The PCR products differ in the amount of 5' and 3' vector sequence flanking the lovE open reading frame.

PCR was performed using a GeneMorph PCR mutagenesis kit (Stratagene, La Jolla, Calif.) according to manufacturer's instructions to achieve medium and high range mutation frequencies.

Plasmid MB2478 was cut with Asp718/XbaI to release a 1.7 kb fragment. The remaining 5.0 kb vector sequence completely lacks lovE ORF sequence.

Example 4: Transformation and Selection for G418R Isolates

All PCR products were purified using a QIAquick PCR purification kit (Qiagen) according to manufacturer's instructions. All vectors were gel purified using a QIAquick gel extraction kit (Qiagen) according to manufacturer's instructions.

The mutagenesis strategy of Muhlrad et al. (*Yeast* 8:79–82 (1992)) was used which involves cotransforming a mutated PCR product and gapped plasmids into *S. cerevisiae*, and then screening for in vivo recombinants having the desired phenotype).

Transformation of *Saccharomyces cerevisiae* was accomplished by the lithium acetate/single-stranded carrier DNA/polyethylene glycol (LiAc/ss-DNA/PEG) protocol (Woods R. A. and Gietz R. D. *Methods Mol. Biol.* 177:85–97 (2001)) with a 1:5 molar ratio of vector:insert DNA to generate >55,000 in vivo recombinant transformants on SC-Ura plates. Transformants were transferred by replica printing to YPD plates containing 100 μg/ml G418 and allowed to grow for 2–4 days at 30° C. (FIG. 1).

Drug resistant clones were confirmed in secondary assays including growth on G418 concentrations up to 2000 μg/ml. The plasmid-dependence of the phenotype was determined by observing the re-appearance of drug sensitivity correlating with loss of the library plasmid. lovE variant plasmids were recovered from promising candidates (Hoffman and Winston (1986) *Gene* 57:267). More than 70 lovE variants were identified and definitively characterized by DNA sequence and/or restriction digestion analysis.

Table 3 summarizes the G418 resistance phenotype and sequence analysis of 26 of these variants.

TABLE 3

| | | | Variant lovE Mutations | | | | | | | | | | |
|---|---|---|---|---|---|---|---|---|---|---|---|---|---|
| lovE allele | lovFp-neo Mediated G418R | MO oligos used for random PCR mutagenesis | Amino Acid Change 1 | Amino Acid Change 2 | Amino Acid Change 3 | Amino Acid Change 4 | Amino Acid Change 5 | Amino Acid Change 6 | Amino Acid Change 7 | Amino Acid Change 8 | Amino Acid Change 9 | Amino Acid Change 10 | Amino Acid Change 11 |
| 1 | −/+ | 2624/2654 | H253R | S341P | | | | | | | | | |
| 2 | +/− | 2624/2654 | R121W | S133L | S322G | | | | | | | | |
| 3 | +++ | 2624/2654 | C73R | A83V | T135I | | | | | | | | |
| 4 | ++ | 2624/2654 | C73R | E177G | | | | | | | | | |
| 5 | ++ | 2624/2654 | C73R | | | | | | | | | | |
| 6 | +/− | 2624/2654 | C153Y | E197K | T281A | | | | | | | | |
| 7 | + | 2624/2654 | C73R | T256A | N466S | | | | | | | | |
| 8 | +++ | 2624/2654 | C73R | E141V | | | | | | | | | |
| 9 | ++ | 2624/2654 | C73R | E303K | | | | | | | | | |
| 10 | +++ | 2624/2654 | Q41K | | | | | | | | | | |
| 16 | +++ | 2680/2686 | Q41K | P16A | G23S | T9M | Q362E | | | | | | |

TABLE 3-continued

Variant lovE Mutations

| lovE allele | lovFp-neo Mediated G418R | MO oligos used for random PCR mutagenesis | Amino Acid Change 1 | Amino Acid Change 2 | Amino Acid Change 3 | Amino Acid Change 4 | Amino Acid Change 5 | Amino Acid Change 6 | Amino Acid Change 7 | Amino Acid Change 8 | Amino Acid Change 9 | Amino Acid Change 10 | Amino Acid Change 11 |
|---|---|---|---|---|---|---|---|---|---|---|---|---|---|
| 19 | +/− | 2700/2701 | R21H | S34A | Q80H | A84S | E303D | H374D | A440T | A441V | C445S | P469S | |
| 20 | + | 2700/2701 | F31L | T409I | | | | | | | | | |
| 21 | +++ | 2700/2701 | F31L | M97I | E113D | D146N | P163S | N367I | H458Y | | | | |
| 30 | +/− | 2681/2686 | I43V | Q295L | | | | | | | | | |
| 31 | ++ | 2680/2686 | F31L | P101S | C153R | C159S | E162K | R293L | S311N | | | | |
| 32 | ++ | 2680/2686 | L14I | E18V | G138C | E338G | V361L | P389S | N400S | | | | |
| 33 | ++ | 2680/2686 | Q41R | S174Y | A402T | | | | | | | | |
| 34 | ++ | 2680/2686 | F31L | T52I | P101Q | P108S | V111I | | | | | | |
| 36 | +/− | 2700/2701 | D85N | I143F | M232I | T315I | S382Y | M385K | | | | | |
| 37 | ++ | 2700/2701 | T46I | Q62R | K77R | S323C | N367Y | V373I | | | | | |
| 38 | −/+ | 2700/2701 | Q41R | T294I | P310L | G337D | P389L | A394V | G436S | | | | |
| 39 | + | 2680/2686 | T52N | V111I | T139 | V184I | T281A | | | | | | |
| 40 | +++ | 2680/2686 | Q41R | D4E | V87I | D110E | E141K | A189T | N276D | T347R | N367I | Q377R | A425T |
| 41 | −/+ | 2680/2686 | D131N | S133L | R312G | A429G | | | | | | | |
| wild-type | − | N/A | N/A | | | | | | | | | | |

Table 4 summarizes amino acid substitutions that were isolated multiple times, suggesting that they are particularly important for improving love variant activity on lovFp-HIS3p-neo expression.

TABLE 4 lovE Mutations Isolated Multiple Times

| Amino Acid Change | Number of Times Isolated in lovE 1–41 | lovE variant |
|---|---|---|
| F31L | 4 | 20, 21, 31, 34 |
| Q41K | 2* | 10, 16 |
| Q41R | 3* | 33, 38, 40 |
| T52I/T52N | 1 each | 34, 39 |
| C73R | 6* | 3, 4, 5, 7, 8, 9 |
| P101S/P101Q | 1 each | 31, 34 |
| V111I | 2 | 34, 39 |
| S133L | 2 | 2, 41 |
| E141V, E141K | 1 each | 8, 40 |
| C153Y/C153R | 1 each | 6, 31 |
| T281A | 2 | 6, 39 |
| N367I/N367Y | 2/1 | 21, 40, 37 |
| P389S/P389L | 1 each | 32, 38 |

*allele was isolated in additional lovE variants that were not fully sequenced

Example 5: Increased lovF-lacZ Expression in *S. cerevisiae*

In order to quantify the increase in lovF expression, β-galactosidase activity was measured in lovE variant transformed *S. cerevisiae* strains that also harbored lovFp-lacZ reporter derivative plasmids. lovF-lacZ reporter derivative plasmids were constructed as follows.

Plasmid MB1918 contains the lovFp-lacZ reporter gene. It can be derived from pRS424 (Sikorski and Hieter (1989) *Genetics* 122:19–27). First, primers MO107 (SEQ ID NO:25) and MO197 (SEQ ID NO:26) are used to PCR amplify the lacZ gene from Yep355 (Myers, et al., *Gene* 45:299–310 (1986)). This lacZ-containing fragment was inserted into the BamHI-HindIII sites of pRS416 (Sikorski and Hieter, *Genetics* 122:19–27 (1989)). This same lacZ fragment can be cut out of the resulting vector with KpnI-NotI and inserted into the same sites of pRS424 to create pRS424-lacZ. Primers MO1293 (SEQ ID NO:27) and MO1294 (SEQ ID NO:28) are used to PCR amplify a 2.09 kb fragment of the lovF promoter from *A. terreus* genomic DNA. The lovF promoter fragment was then cut with NotI-BglII and inserted into NotI-BamHI linearized pRS424-lacZ.

Plasmid MB2114 contains the lovFp-CYC1p-lacZ reporter gene. It can be derived from pRS424-lacZ (see MB1918 plasmid construction). Primers MO1787 (SEQ ID NO:29) and MO1788 (SEQ ID NO:30) are used to amplify the 264 bp basal CYC1 element from pRS415 CYC1 (Mumberg, et al., *Gene* 156:119–122 (1995)). This 264 bp fragment was inserted upstream of the pRS424-lacZ derivative which has been digested with SpeI-BamHI. Finally, the lovF promoter from MB1918 was PCR amplified with MO1793 (SEQ ID NO:31) and MO1794 (SEQ ID NO:32) and inserted into the NotI-SpeI sites to create MB2114.

Yeast strains utilized in this study include strains MY2145 and MY2159, which are both derived from the *S. cerevisiae* sigma 1278b strain background; the genotypes are both strains are as follows: MATa ura3Δ0 leu2Δ0 his3Δ::hisG trp1Δ0::hisG. MY2145 and MY2159 contain the lovFp-lacZ reporter plasmids MB2114 and MB1918, respectively.

MY2124 transformed with individual lovE variant plasmids was mated to *S. cerevisiae* strains MY2154 and MY2159. Diploids were selected on SC-UraTrp media. Multiple diploids from each individual mating were assayed for lovFp-lacZ expression using 96 well format β-galactosidase assays. For β-galactosidase assays, cells were transferred from transformation plates to 96-well microtiter plates containing 200 μl Z buffer. 12 strains were transferred simultaneously using a 12-channel multi-pipettor to scoop cells from transformation plates. Duplicate samples were prepared for all assays. $OD_{600}$ readings were taken on samples in Z buffer. These values were used to normalize for equal cell number in all assays. After determining $OD_{600}$, 150 μl of each sample in Z buffer was transferred onto a Millipore Multiscreen Assay System (Nitrocellulose Immobilon N.C.), filtered, and then washed by filtering 200 μl Z buffer. 100 μl Z buffer with βME and detergents was then added to each well, as was 20 μl 4 mg/ml ONPG. Reactions were incubated at 30° C., stopped with 50 μl 1 M $Na_2CO_3$, filtered into a polystyrene 96-well assay plate, and $OD_{420}$ was determined for each assay well. μ-galactosidase units were determined using the Miller formula (O.D. 420×1000)/(OD600*minutes*volume in mL). Z buffer is made by dissolving the following in 1 L of water (16.1 g $Na_2HPO_4$-

7H$_2$O, 5.5 g NaH$_2$PO$_4$-H$_2$O, 0.75 g KCl and 0.246 g MgSO$_4$-7H$_2$O). Z buffer with detergents and βME is made as follows: 9.8 ml Z buffer, 100 μl 20 mg/ml CTAB, 100 μl 10 mg/ml sodium deoxycholate, and 69 μl βME Control plasmids utilized in these studies included MB968, MB2478 and MB1644.

Results of these studies are presented in FIGS. 2–5, demonstrating increased transcription-activating properties of the lovE variants disclosed herein.

Example 6: Secondary Metabolite Production

Transformation of filamentous fungi was performed according to the following procedure. Protoplasts were generated by inoculating rich media with spores. Spores were allowed to germinate for about 20 hrs or until germ tubes were between 5 and 10 spore lengths. The germlings were centrifuged and washed twice with sterile distilled water and once with 1 M magnesium sulfate. Germlings were then resuspended in 1 M magnesium sulfate containing approximately 2 mg/ml of Novozyme. Tubes were then incubated at 30° C. shaking at 80 RPM for about 2 hrs or until most of the hyphae were digested and protoplasts were abundant. Protoplasts were filtered through one layer of Miracloth. At least one volume of STC was added and protoplasts were centrifuged. Protoplasts were washed twice with STC. Protoplasts then were resuspended in 1 ml STC and counted in a hemacytometer. A final concentration of approximately 5×10$^7$ protoplasts/ml were frozen in a 9:1:0.1 solution of STC, SPTC and DMSO in a Nalgene Cryo cooler at −80° C. (cools −1° C./min).

Solutions for transformation were as follows: STC (0.8 M Sorbitol, 25 mM Tris-HCl pH 7.5, 25 mM CaCl$_2$) and SPTC (0.8 M Sorbitol, 40% PEG 4000, 25 mM Tris-HCl pH 8, 50 mM CaCl$_2$). Transformation was accomplished according to the following protocol. 1–5 μg of DNA comprising a lovE variant according to the invention in a fungal expression vector was placed in a 50 ml Falcon tube. 100 μl of previously frozen protoplasts were added to the DNA, gently mixed, and then incubated on ice for 30 min. 15 μl of SPTC was added, followed by mixing by tapping and incubation at RT for 15 min. 500 μl SPTC was added and mixed well by tapping and rolling, then incubated at RT for 15 min. 25 mls of regeneration minimal medium was added, mixed well and poured on plates containing 25 mls of regeneration minimal medium with 2X the concentration of selection drug.

Transformation plates were incubated at 26° C. for 5–6 days or until colonies started to appear. Regeneration minimal medium contains trace elements, salts, 25 mM sodium nitrate, 0.8 M Sucrose, and 1% agarose at pH 6.5. The selection drug that was used successfully with *A. terreus* is phleomycin, a broad-spectrum glycopeptide antibiotic. Transformants were picked onto new plates with a toothpick (if the fungus was sporulating) or with sterile forceps (if the fungus did not sporulate). Purification plates contained minimal medium (same as regeneration minimal medium but containing 2% instead of 0.8 M sucrose) and 1X drug concentration. Picked transformants were incubated at 26° C. for 5–6 days.

Transformants were grown in production media for secondary metabolite production. Briefly, for *A. terreus* and lovastatin production, spores were used as the inoculum. Spores were obtained from the purification plate by using a wooden inoculation stick. The medium was RPM containing corn steep liquor, sodium nitrate, potassium phosphate, magnesium sulfate, sodium chloride, P2000 (Dow chemical), trace elements and lactose or glucose as carbon source. The medium was pH 6.5. Flasks were incubated at 26° C. with shaking at 225 RPM. For static 96-well cultures, the same medium was used and the spores were obtained from the purification plate with a wooden toothpick. 96-well plates were incubated, without shaking at 26° C.

Sampling was done after after 5 days for lovastatin. For shake flask experiments 1–1.5 mls of supernatant was placed into 96-well plates, which were centrifuged and supernatants transferred to new 96-well plates. Samples were frozen at −80° C. for storage or for later assays.

Cultures that were grown standing in a 96-well plate were centrifuged and the supernatant was transferred to a new 96 well plate. Samples were frozen at −80° C.

Example 7: Measurement of Secondary Metabolite Production

Figure 6:
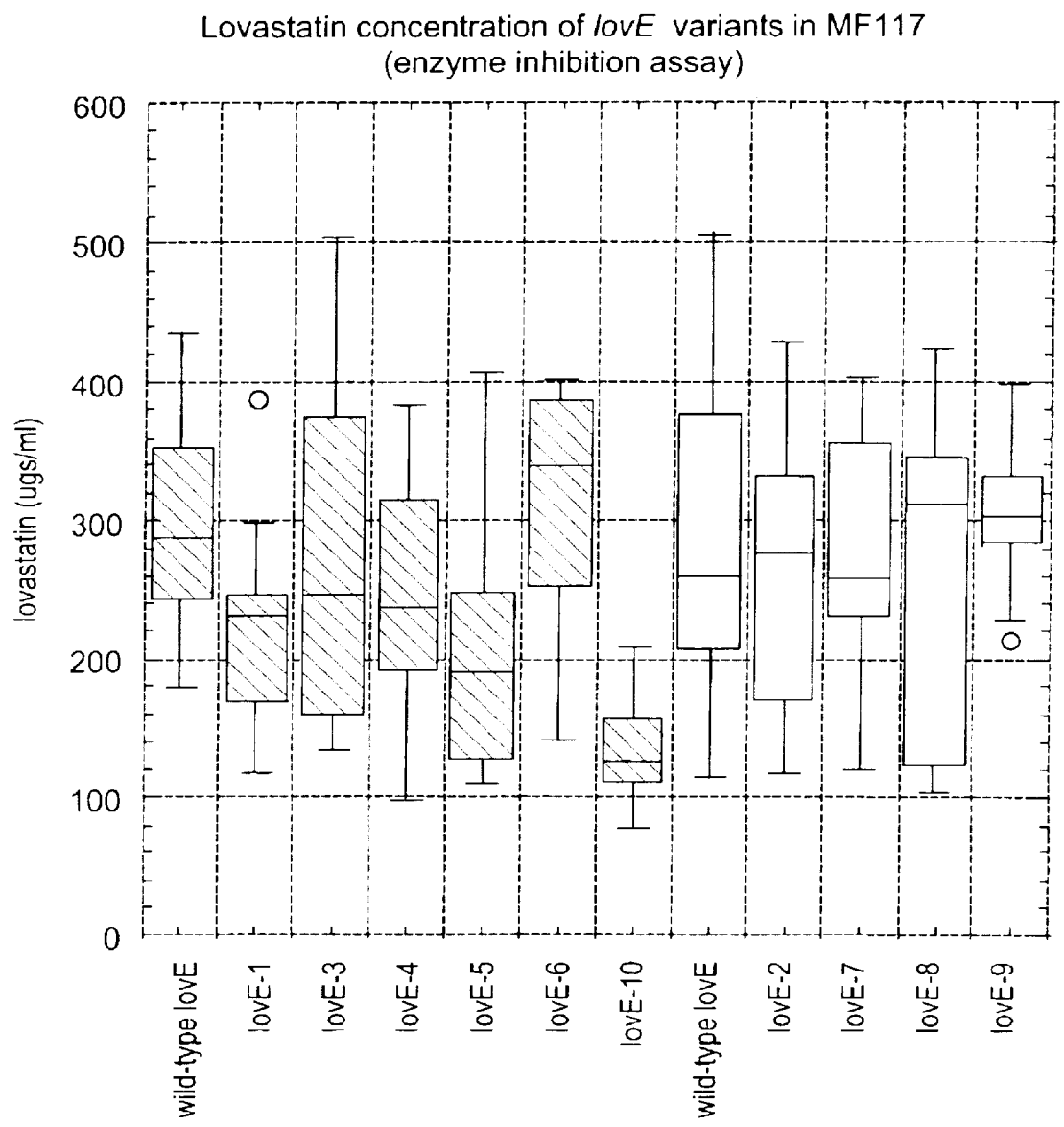

The concentration of the secondary metabolite lovastatin was determined by enzyme inhibition assay (FIG. 6). Briefly, 10 μL of sample was removed and diluted 1:100 in H$_2$O. 10 μl of this diluted broth was assayed in a reaction (200 μL total) containing 1 mM HMGCoA, 1 mM NADPH, 0.005 mM DTT and 5 μl (His)$_6$HMGR. The disappearance of absorbance at 340 nm was observed over time. This represents the disappearance of NADPH, and lovastatin inhibits this reaction.

The initial velocities were calculated for the reactions containing samples, adjusted for dilution, and compared to reactions containing lovastatin standards to determine levels of metabolite produced. (His)$_6$HMGR was expressed in *Saccharomyces cerevisiae* and purified with a nickel column.

The results from ten individual transformants for each allele are shown in standard box plot format in FIG. 6. Lovastatin concentration from the corresponding wild-type lovE control is shown in matching fill pattern. For example, lovE alleles 2, 7, 8 and 9 were all transformed and assayed at the same time as the non-hatched wild-type control. The horizontal line in each individual box represents the median.

Lovastatin concentration was also determined by high pressure liquid chromatography (HPLC). Briefly, 100 μL of broth sample was removed and diluted 1:10 into 70% H$_2$O-30% acetonitrile (900 μl). This mixture was spun down to pellet debris at 13000 RPM for 5 minutes. 900 μl of this diluted broth was transferred to a vial and the sample was analyzed by HPLC. 10 μl were injected into a Waters HPLC system (996 photo-diode array detector, 600 E pump controller and 717 autosampler) equipped with a YMC-Pack ODS column (Aq-302-3, 150×4.6 mm ID, S-3 μM pore size) and eluted with isocratic 40% aqueous acetic acid (0.7%)-60% acetonitrile for 8 minutes. Lovastatin was detected at 238 nm to have a retention time of 6.5 minutes and was quantified using a calibration curve created from pure lovastatin samples.

Figure 7A:
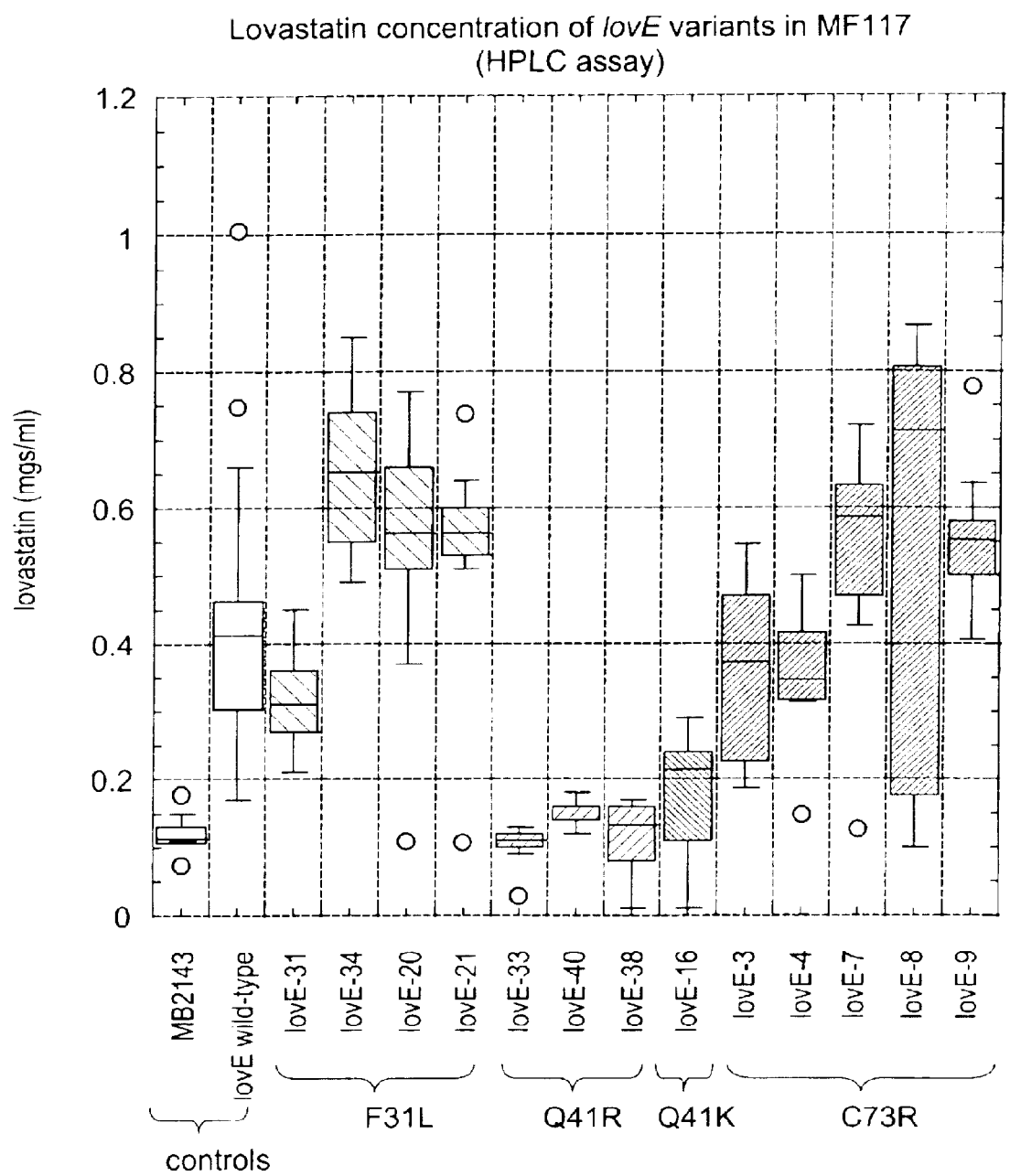
FIG. 7A is a graphic depiction of lovastatin culture concentration, as measured by HPLC analysis, from broths of A. terreus cultures expressing lovE variant proteins 1–10 in MF117.
Figure 7B:
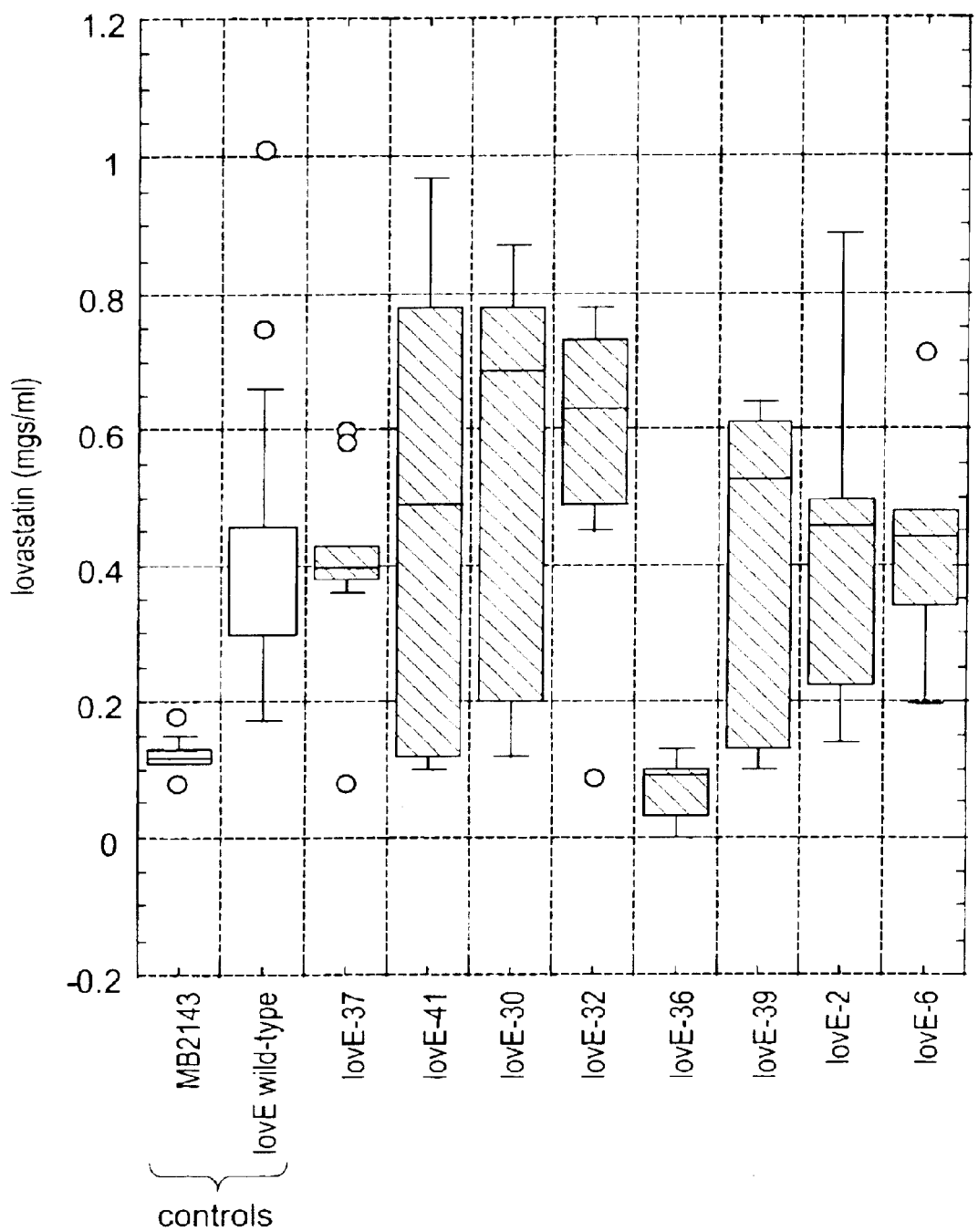
FIG. 7B is a graphic depiction of lovastatin culture concentration, as measured by HPLC analysis, from broths of A. terreus cultures expressing lovE variant proteins 2, 6, 30, 32, 36, 37, 39, and 41 in MF117.

The results from ten individual transformants for each lovE variant are shown in standard box plot format in FIG. 7A and 7B. Thirty individual wild-type lovE transformants and ten individual MB2143 negative control transformants were tested. Identical controls are plotted in FIGS. 7A and 7B.

PCR analysis of *A. terreus* transformants demonstrates that greater than fifty percent of the transformants contain the transgene. Variability in levels of transgene expression can presumably be influenced by integration site and copy number. lovE variants containing identical amino acid substitutions are labeled.

The amino acid and nucleic acid sequences of lovE variant sequences are presented in Table 5 and Table 6, respectively.

Table 5

Amino Acid Sequences of Variants of the lovE Gene lovE-1 maadqgiftnsvtlspvegsrtggtlprrafrrscdrchaqkikctgnkevtgrapcqrcqqagl  (SEQ ID NO:41)
rcvysercpkrklrqsraadlvsadpdpclhmssppvpsqslpldvseshssntsrqfldppdsy
dwswtsigtdeaidtdcwglsqcdggfscqleptlpdlsppfestvekaplppvssdiaraasaq
relfddlsavsqeleeillavtvewpkqeiwthpigmffnasrrlltvlrqqaqadcrqgtldec
lrtknlftavhcyilnvriltaiselllsqirrtqnshmsplegsrsqspsrddtssssghssvd
tipffsenlpigelfpyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnnipp lovE-2 maadqgiftnsvtlspvegsrtggtlprrafrrscdrchaqkikctgnkevtgrapcqrcqqagl  (SEQ ID NO:42)
rcvysercpkrklrqsraadlvsadpdpclhmssppvpsqslpldvseshssntswqfldppdsy
dwlwtsigtdeaidtdcwglsqcdggfscqleptlpdlspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtsssghsvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnnipp lovE-3 maadqgiftnsvtlspvegsrtggtlprrafrrscdrchaqkikctgnkevtgrapcqrcqqagl  (SEQ ID NO:43)
rcvyserrpkrklrqsrvadlvsadpdpclhmssppvpsqslpldvseshssntsrqfldppdsy
dwswisigtdeaidtdcwglsqcdggfscqleptlpdlspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnnipp lovE-4 maadqgiftnsvtlspvegsrtggtlprrafrrscdrchaqkikctgnkevtgrapcqrcqqagl  (SEQ ID NO:44)
rcvyserrpkrklrqsraadlvsadpdpclhmssppvpsqslpldvseshssntsrqfldppdsy
dwswtsigtdeaidtdcwglsqcdggfscqleptlpdlspfestvgkaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnnipp lovE-5 maadqgiftnsvtlspvegsrtggtlprrafrrscdrchaqkikctgnkevtgrapcqrcqqagl  (SEQ ID NO:45)
rcvyserrpkrklrqsraadlvsadpdpclhmssppvpsqslpldvseshssntsrqfldppdsy Table 5-continued Amino Acid Sequences of Variants of the lovE Gene dwswtsigtdeaidtdcwglsqcdggfscqleptlpdlsppfestvekaplppvssdiaraasaq relfddlsavsqeleeillavtvewpkqeiwthpigmffnasrrlltvlrqqaqadchqgtldec lrtknlftavhcyilnvriltaiselllsqirrtqnshmsplegsrsqspsrddtssssghssvd tipffsenlpigelfsyvdplthalfsacttlhvgvqllreneitlgvhsaqgiaasismsgepg ediartgatnsarceeqpttpaarvlfmflsdegafqeaksagsrgrtiaalrrcyedifslark hkhgmlrdlnnipp lovE-6 maadqgiftnsvtlspvegsrtggtlprrafrrscdrchaqkikctgnkevtgrapcqrcqqagl    (SEQ ID NO:46)

rcvysercpkrklrqsraadlvsadpdpclhmssppvpsqslpldvseshssntsrqfldppdsy dwswtsigtdeaidtdcwglsqydggfscqleptlpdlsppfestvekaplppvssdiaraasaq rklfddlsavsqeleeillavtvewpkqeiwthpigmffnasrrlltvlrqqaqadchqgtldec lrtknlftavhcyilnvrilaaiselllsqirrtqnshmsplegsrsqspsrddtssssghssvd tipffsenlpigelfsyvdplthalfsacttlhvgvqllreneitlgvhsaqgiaasismsgepg ediartgatnsarceeqpttpaarvlfmflsdegafqeaksagsrgrtiaalrrcyedifslark hkhgmlrdlnnipp lovE-7 maadqgiftnsvtlspvegsrtggtlprrafrrscdrchaqkikctgnkevtgrapcqrcqqagl    (SEQ ID NO:47)

rcvyserrpkrklrqsraadlvsadpdpclhmssppvpsqslpldvseshssntsrqfldppdsy dwswtsigtdeaidtdcwglsqcdggfscqleptlpdlsppfestvekaplppvssdiaraasaq relfddlsavsqeleeillavtvewpkqeiwthpigmffnasrrlltvlrqqaqadchqgtldec lrtknlftavhcyilnvriltaiselllsqirrtqnshmsplegsrsqspsrddtssssghssvd tipffsenlpigelfsyvdplthalfsacttlhvgvqllreneitlgvhsaqgiaasismsgepg ediartgatnsarceeqpttpaarvlfmflsdegafqeaksagsrgrtiaalrrcyedifslark hkhgmlrdlnsipp lovE-8 maadqgiftnsvtlspvegsrtggtlprrafrrscdrchaqkikctgnkevtgrapcqrcqqagl    (SEQ ID NO:48)

rcvyserrpkrklrqsraadlvsadpdpclhmssppvpsqslpldvseshssntsrqfldppdsy dwswtsigtdeaidtdcwglsqcdggfscqleptlpdlsppfestvekaplppvssdiaraasaq relfddlsavsqeleeillavtvewpkqeiwthpigmffnasrrlltvlrqqaqadchqgtldec lrtknlftavhcyilnvriltaiselllsqirrtqnshmsplegsrsqspsrddtssssghssvd tipffsenlpigelfsyvdplthalfsacttlhvgvqllreneitlgvhsaqgiaasismsgepg ediartgatnsarceeqpttpaarvlfmflsdegafqeaksagsrgrtiaalrrcyedifslark hkhgmlrdlnsipp lovE-9 maadqgiftnsvtlspvegsrtggtlprrafrrscdrchaqkikctgnkevtgrapcqrcqqagl    (SEQ ID NO:49)

rcvyserrpkrklrqsraadlvsadpdpclhmssppvpsqslpldvseshssntsrqfldppdsy dwswtsigtdeaidtdcwglsqcdggfscqleptlpdlsppfestvekaplppvssdiaraasaq relfddlsavsqeleeillavtvewpkqeiwthpigmffnasrrlltvlrqqaqadchqgtldec Table 5-continued Amino Acid Sequences of Variants of the lovE Gene lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnsipp lovE-10 maadqgiftnsvtlspvegsrtsgtlprrafrrscdrchaqkikctgnkevtgrapcqrcqqagl  (SEQ ID NO:50)
rcvyserrpkrklrqsraadlvsadpdpclhmssppvpsqslpldvseshssntsrqfldppdsy
dwswtsigtdeaidtdcwglsqcdggfscqleptlpdlpspfestvekaplppvssdiaraasaq
relfddlsavsqeleeillavtvewpkqeiwthpigmffnasrrlltvlrqqaqadchqgaldec
lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnsipp lovE-16 maadqgifmnsvtlsavegsrtsgtlprrafrracdrchakkikctgnkevtgrapcqrcqqagl  (SEQ ID NO:51)
rcvysecrpkrklrqsraadlvsadpdpclhmssppvpsqslpldvseshssntsrqfldppdsy
dwswtsigtdeaidtdcwglsqcdggfscqleptlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnnipp lovE-19 maadqgiftnsvtlspvegshtggtlprralrrscdrchaqkikctgnkevtgrapcqrcqqagl  (SEQ ID NO:52)
rcvysercpkrklrhsrasdlvsadpdpclhmssppvpsqslpldvseshssntsrqfldppdsy
dwswtsigtdeaidtdcwglsqcdggfscqleptlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmspldgsrsqspsrddtssssghssvd
tipffsenlpigelfsyvdplthalfsacttlhvgvqllreneitlgvdsaqgiaasismsgepg
ediartgatnsarceeqpttpaarvlfmflsdegafqeaksagsrgrtitvlrrsyedifslark
hkhgmlrdlnnipps lovE-20 maadqgiftnsvtlspvegsrtggtlprrafrrscdrchaqkikctgnkevtgrapcqrcqqagl  (SEQ ID NO:53)
rcvysercpkrklrqsraadlvsadpdpclhmssppvpsqslpldvseshssntsrqfldppdsy
dwswtsigtdeaidtdcwglsqcdggfscqleptlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnsarceeqpitpaarvlfmflsdegafqeaksagsrgrtiaalrrcyedifslark TABLE 5-continued Amino Acid Sequences of Variants of the lovE Gene hkhgmlrdlnnipp lovE-21 maadqgiftnsvtlspvegsrtggtlprrafrrscdrchaqkikctgnkevtgrapcqrcqqagl (SEQ ID NO:54)
rcvysercpkrklrqsraadlvsadpdpclimssppvpsqslpldvsdshssntsrqfldppdsy
dwswtsigtdeaidtncwglsqcdggfscqlestlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreieitlgvhsaqgiaasismsgepg
ediartgatnsarceeqpttpaarvlfmflsdegafqeaksagsrgrtiaalrrcyedifslark
hkygmlrdlnnipp lovE-30 maadqgiftnsvtlspvegsrtggtlprrafrrscdrchaqkvkctgnkevtgrapcqrcqqagl (SEQ ID NO:55)
rcvysercpkrklrqsraadlvsadpdpclhmssppvpsqslpldvseshssntsrqfldppdsy
dwswtsigtdeaidtdcwglsqcdggfscqleptlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnnipc lovE-31 maadqgiftnsvtlspvegsrtggtlprralrrscdrchaqkikctgnkevtgrapcqrcqqagl (SEQ ID NO:56)
rcvysercpkrklrqsraadlvsadpdpclhmsspsvpsqslpldvseshssntsrqfldppdsy
dwswtsigtdeaidtdcwglsqrdggfssqlkptlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirltqnshmsplegsrsqspnrddtssssghssvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnnipp lovE-32 maadqgiftnsvtispvvgsrtggtlprrafrrscdrchaqkikctgnkevtgrapcqrcqqagl (SEQ ID NO:57)
rcvysercpkrklrqsraadlvsadpdpclhmssppvpsqslpldvseshssntsrqfldppdsy
dwswtsictdeaidtdcwglsqcdggfscqleptlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigglfsyvdplthalfsacttlhvgeqllreneitlgvhsaqgiaasismsgesg
ediartgatssarceeqpttpaarvlfmflsdegafqeaksagsrgrtiaalrrcyedifslark
hkhgmlrdlnnipp Table 5-continued Amino Acid Sequences of Variants of the lovE Gene lovE-33 maadqgiftnsvtlspvegsrtggtlprrafrrscdrcharkikctgnkevtgrapcqrcqqagl (SEQ ID NO:58)
rcvysecrpkrklrqsraadlvsadpdpclhmssppvpsqslpldvseshssntsrqfldppdsy
dwswtsigtdeaidtdcwglsqcdggfscqleptlpdlpspfeytvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnstrceeqpttpaarvlfmflsdegafqeaksagsrgrtiaalrrcyedifslark
hkhgmlrdlnnipp lovE-34 maadqgiftnsvtlspvegsrtggtlprralrrscdrchaqkikctgnkevigrapcqrcqqagl (SEQ ID NO:59)
rcvysercpkrklrqsraadlvsadpdpclhmsspqvpsqslsldiseshssntsrqfldppdsy
dwswtsigtdeaidtdcwglsqcdggfscqleptlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreneitlgvhsaqgiaasismsgepg
ediartgatnsarceeqpttpaarvlfmflsdegafqeaksagsrgrtiaalrrcyedifslark
hkhgmlrdlnnipp lovE-36 maadqgiftnsvtlspvegsrtggtlprrafrrscdrchaqkikctgnkevtgrapcqrcqqagl (SEQ ID NO:60)
rcvysercpkrklrqsraanlvsadpdpclhmssppvpsqslpldvseshssntsrqfldppdsy
dwswtsigtdeafdtdcwglsqcdggfscqleptlpdlpspfestvekaplppvssdiaraasaq
relfddlsavsqeleeillavtvewpkqeiwthpigiffnasrrlltvlrqqaqadchqgtldec
lrtknlftavhcyilnvriltaiselllsqirrtqnshmsplegsrsqspsrddissssghssvd
tipffsenlpigelfsyvdplthalfsacttlhvgvqllreneitlgvhsaqgiaayisksgepg
ediartgatnsarceeqpttpaarvlfmflsdegafqeaksagsrgrtiaalrrcyedifslark
hkhgmlrdlnnipp lovE-37 maadqgiftnsvtlspvegsrtggtlprrafrrscdrchaqkikctgnkevtgrapcqrcqqagl (SEQ ID NO:61)
rcvysercpkrrlrqsraadlvsadpdpclhmssppvpsqslpldvseshssntsrqfldppdsy
dwswtsigtdeaidtdcwglsqcdggfscqleptlpdlpspfestvekaplppvssdiaraasaq
relfddlsavsqeleeillavtvewpkqeiwthpigmffnasrrlltvlrqqaqadchqgtldec
lrtknlftavhcyilnvriltaiselllsqirrtqnshmsplegsrsqspsrddtssssghssvd
tipffsenlpigelfsyvdplthalfsacttlhvgvqllreyeitlgihsaqgiaasismsgepg
ediartgatnsarceeqpttpaarvlfmflsdegafqeaksagsrgrtiaalrrcyedifslark
hkhgmlrdlnnipp lovE-38 maadqgiftnsvtlspvegsrtggtlprrafrrscdrcharkikctgnkevtgrapcqrcqqagl (SEQ ID NO:62)
rcvysercpkrklrqsraadlvsadpdpclhmssppvpsqslpldvseshssntsrqfldppdsy

Table 5-continued

Amino Acid Sequences of Variants of the lovE Gene dwswtsigtdeaidtdcwglsqcdggfscqleptlpdlspspfestvekaplppvssdiaraasaq relfddlsavsqeleeillavtvewpkqeiwthpigmffnasrrlltvlrqqaqadchqgtldec lrtknlftavhcyilnvriltaiselllsqirriqnshmsplegsrsqslsrddtssssghssvd tipffsenlpidelfsyvdplthalfsacttlhvgvqllreneitlgvhsaqgiaasismsgelg edivrtgatnsarceeqpttpaarvlfmflsdegafqeaksagsrsrtiaalrrcyedifslark hkhgmlrdlnnipp lovE-39 maadqgiftnsvtlspvegsrtggtlprrafrrscdrchaqkikctgnkevngrapcqrcqqagl          (SEQ ID NO:63)

rcvysercpkrklrqsraadlvsadpdpclhmssppvpsqslpldiseshssntsrqfldppdsy dwswtsigideaidtdcwglsqcdggfscqleptlpdlspspfestvekaplppvisdiaraasaq relfddlsavsqeleeillavtvewpkqeiwthpigmffnasrrlltvlrqqaqadchqgtldec lrtknlftavhcyilnvrilaaiselllsqirrtqnshmsplegsrsqspsrddtssssghssvd tipffsenlpigelfsyvdplthalfsacttlhvgvqllreneitlgvhsaqgiaasismsgepg ediartgatnsarceeqpttpaarvlfmflsdegafqeaksagsrgrtiaalrrcyedifslark hkhgmlrdlnnipp lovE-40 maaeqgiftnsvtlspvegsrtggtlprrafrrscdrcharkikctgnkevtgrapcqrcqqagl          (SEQ ID NO:64)

rcvysercpkrklrqsraadlisadpdpclhmssppvpsqslplevseshssntsrqfldppdsy dwswtsigtdkaidtdcwglsqcdggfscqleptlpdlspspfestvekaplppvssditraasaq relfddlsavsqeleeillavtvewpkqeiwthpigmffnasrrlltvlrqqaqadchqgtldec lrtknlftavhcyildvriltaiselllsqirrtqnshmsplegsrsqspsrddtssssghssvd tipffsenlpigelfsyvdplrhalfsacttlhvgvqllreieitlgvhsargiaasismsgepg ediartgatnsarceeqpttpaarvlfmflsdegtfqeaksagsrgrtiaalrrcyedifslark hkhgmlrdlnnipp lovE-41 maadqgiftnsvtlspvegsrtggtlprrafrrscdrchaqkikctgnkevtgrapcqrcqqagl          (SEQ ID NO:65)

rcvysercpkrklrqsraadlvsadpdpclhmssppvpsqslpldvseshssntsrqfldppdsy nwlwtsigtdeaidtdcwglsqcdggfscqleptlpdlspspfestvekaplppvssdiaraasaq relfddlsavsqeleeillavtvewpkqeiwthpigmffnasrrlltvlrqqaqadchqgtldec lrtknlftavhcyilnvriltaiselllsqirrtqnshmsplegsrsqspsgddtssssghssvd tipffsenlpigelfsyvdplthalfsacttlhvgvqllreneitlgvhsaqgiaasismsgepg ediartgatnsarceeqpttpaarvlfmflsdegafqegksagsrgrtiaalrrcyedifslark hkhgmlrdlnnipp

Table 6

DNA Sequences of Variants of the lovE Gene lovE-1

ATGGCTGCAGATCAAGGTATATTCACGAACTCGGTCACTCTCTCGCCAGTGGAGGGTTCACGCAC          (SEQ ID NO:66)

Table 6-continued

DNA Sequences of Variants of the lovE Gene

CGGTGGAACATTACCCCGCCGTGCATTCCGACGCTCTTGTGATCGGTGTCATGCACAAAAGATCA
AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAGTTTCTTGATCCACCGGACAGCTAC
GACTGGTCGTGGACCTCGATTGGCACTGACGAGGCTATTGACACTGACTGCTGGGGGCTGTCCCA
ATGTGATGGAGGCTTCAGCTGTCAGTTAGAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCCCCTATGTTGACCCCCTGAC
ACACGCCCTATTCTCGGCTTGCACTACGTTACATGTTGGGGTACAATTGCTGCGTGAGAATGAGA
TTACTCTGGGAGTACACTCCGCCCAGGGCATTGCAGCTTCCATCAGCATGAGCGGGGAACCAGGC
GAGGATATAGCCAGGACAGGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCCTCGCCCGCAAA
CACAAACATGGCATGCTCAGAGACCTCAACAATATTCCTCCATGA lovE-2

ATGGCTGCAGATCAAGGTATATTCACGAACTCGGTCACTCTCTCGCCAGTGGAGGGTTCACGCAC  (SEQ ID NO:67)
CGGTGGAACATTACCCCGCCGTGCATTCCGACGCTCTTGTGATCGGTGTCATGCACAAAAGATCA
AATGTACTGGAAATAAGGAGGTTACTGGCCGTGCTCCCTGTCAGCGTTGCCAGCAGGCTGGACTT
CGATGCGTCTACAGTGAGCGACGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAATTTCTTGATCCACCGGACAGCTAC
GACTGGTTGTGGATCTCGATTGGCACTGACGAGGCTATTGACACTGACTGCTGGGGGCTGTCCCA
ATGTGATGGAGGCTTCAGCTGTCAGTTAGAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAGTGGCCGAAGCAGGAAATCTGGACCCATCCCATCGGAATGTTTTTCAATGCGTCACGAC
GGCTTCTTACTGTCCTGCGCCAACAAGCGCAGGCCAACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACGGCAGTGTTGAC
ACCATACCCTTCTTTAGCGAGAACCTCCCTATTGGTGAGCTGTTCTCCTATGTTGACCCCCTGAC

Table 6-continued

DNA Sequences of Variants of the lovE Gene

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-3

ATGGCTGCAGATCAAGGTATATTCACGAACTCGGTCACTCTCTCGCCAGTGGAGGGTTCACGCAC (SEQ ID NO:68)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGACGCCCCAAGCGCAAGCTACGCCAATCCAGGGTAGCGGATCTCGT

CTCTGCTGACCCAGATCCCTGCTTGCACATGTCCTCGCCTCCAGTGCCCTCACAGAGCTTGCCGC

TAGACGTATCCGAGTCGCATTCCTCAAATACCTCCCGGCAATTTCTTGATCCACCGGACAGCTAC

GACTGGTCGTGGATCTCGATTGGCACTGACGAGGCTATTGACACTGACTGCTGGGGGCTGTCCCA

ATGTGATGGAGGCTTCAGCTGTCAGTTACAGCCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCATCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCTCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-4

ATGGCTGCAGATCAAGGTATATTCACGAACTCGGTCACTCTCTCGCCAGTGGAGGGTTCACGCAC (SEQ ID NO:69)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGACGCCCCAAGCGCAAGCTACGCCAATCCAGGGCAGCGGATCTCGT

CTCTGCTGACCCAGATCCCTGCTTGCACATGTCCTCGCCTCCAGTGCCCTCACAGAGCTTGCCGC

TAGACGTATCCGAGTCGCATTCCTCAAATACCTCCCGGCAGTTTCTTGATCCACCGGACAGCTAC

GACTGGTCGTGGACCTCGATTGGCACTGACGAGGCTATTGACACTGACTGCTGGGGGCTGTCCCA

ATGTGATGGAGGCTTCAGCTGTCAGTTAGAGCCAACGCTGCCGGATCTACCTTCGCCCTTCGAGT

CTACGGTTGGAAAAGCTCCGTTGCCACCGGTATCGAGCGACATTGCTCGTGCGGCCAGTGCGCAA

Table 6-continued

DNA Sequences of Variants of the lovE Gene

CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCTCCTATGTTGACCCCCTGAC
ACACGCCCTATTCTCGGCTTGCACTACGTTACATGTTGGGGTACAATTGCTGCGTGAGAATGAGA
TTACTCTGGGAGTACACTCCGCCCAGGGCATTGCAGCTTCCATCAGCATGAGCGGGGAACCAGGC
GAGGATATAGCCAGGACAGGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCCTCGCCCGCAAA
CACAAACATGGCATGCTCAGAGACCTCAACAATATTCCTCCATGA lovE-5

ATGGCTGCAGATCAAGGTATATTCACGAACTCGGTCACTCTCTCGCCAGTGGAGGGTTCACGCAC (SEQ ID NO:70)
CGGTGGAACATTACCCCGCCGTGCATTCCGACGCTCTTGTGATCGGTGTCATGCACAAAAGATCA
AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAGTTTCTTGATCCACCGGACAGCTAC
GACTGGTCGTGGACCTCGATTGGCACTGACGAGGCTATTGACACTGACTGCTGGGGGCTGTCCCA
ATGTGATGGAGGCTTCAGCTGTCAGTTAGAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCCCCTATGTTGACCCCCTGAC
ACACGCCCTATTCTCGGCTTGCACTACGTTACATGTTGGGGTACAATTGCTGCGTGAGAATGAGA
TTACTCTGGGAGTACACTCCGCCCAGGGCATTGCAGCTTCCATCAGCATGAGCGGGGAACCAGGC
GAGGATATAGCCAGGACAGGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCCTCGCCCGCAAA
CACAAACATGGCATGCTCAGAGACCTCAACAATATTCCTCCATGA lovE-6

ATGGCTGCAGATCAAGGTATATTCACGAACTCGGTCACTCTCTCGCCAGTGGAGGGTTCACGCAC (SEQ ID NO:71)

Table 6-continued

DNA Sequences of Variants of the lovE Gene

CGGTGGAACATTACCCCGCCGTGCATTCCGACGCTCTTGTGATCGGTGTCATGCACAAAAGATCA
AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAGTTTCTTGATCCACCGGACAGCTAC
GACTGGTCGTGGACCTCGATTGGCACTGACGAGGCTATTGACACTGACTGCTGGGGGCTGTCCCA
ATATGATGGAGGCTTCAGCTGTCAGTTACAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCTCCTATGTTGACCCCCTGAC
ACACGCCCTATTCTCGGCTTGCACTACGTTACATGTTGGGTACAATTGCTGCGTGAGAATGAGA
TTACTCTGGGAGTACACTCCGCCCAGGGCATTGCAGCTTCCATCAGCATGAGCGGGGAACCAGGC
GAGGATATAGCCAGGACAGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCCTCGCCCGCAAA
CACAAACATGGCATGCTCAGAGACCTCAACAATATTCCTCCATGA lovE-7

ATGGCTGCAGATCAAGGTATATTCACGAACTCGGTCACTCTCTCGCCAGTGGAGGGTTCACGCAC    (SEQ ID NO:72)
CGGTGGAACATTACCCCGCCGTGCATTCCGACGCTCTTGTGATCGGTGTCATGCACAAAAGATCA
AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAGTTTCTTGATCCACCGGACAGCTAC
GACTGGTCGTGGACCTCGATTGGCACTGACGAGGCTATTGACACTGACTGCTGGGGGCTGTCCCA
ATGTGATGGAGGCTTCAGCTGTCAGTTACAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCGTCAAGGCGCACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCTCCTATGTTGACCCCCTGAC
ACACGCCCTATTCTCGGCTTGCACTACGTTACATGTTGGGTACAATTGCTGCGTGAGAATGAGA

Table 6-continued

DNA Sequences of Variants of the lovE Gene

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAGTATTCCTCCATGA lovE-8

ATGGCTGCAGATCAAGGTATATTCACGAACTCGGTCACTCTCTCGCCAGTGGAGGGTTCACGCAC    (SEQ ID NO:73)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGACGCCCCAAGCGCAAGCTACGCCAATCCAGGGCAGCGGATCTCGT

CTCTGCTGACCCAGATCCCTGCTTGCACATGTCCTCGCCTCCAGTGCCCTCACAGAGCTTGCCGC

TAGACGTATCCGAGTCGCATTCCTCAAATACCTCCCGGCAATTTCTTGATCCACCGGACAGCTAC

GACTGGTCGTGGACCTCGATTGGCACTGACGAGGCTATTGACACTGACTGCTGGGGGCTGTCCCA

ATGTGATGGAGGCTTCAGCTGTCAGTTACAGCCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCATCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCTCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-9

ATGGCTGCAGATCAAGGTATATTCACGAACTCGGTCACTCTCTCGCCAGTGGAGGGTTCACGCAC    (SEQ ID NO:74)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGACGCCCCAAGCGCAAGCTACGCCAATCCAGGGCAGCGGATCTCGT

TTCTGCTGACCCAGATCCCTGCTTGCACATGTCCTCGCCTCCAGTGCCCTCACAGAGCTTGCCAC

TAGACGTATCCGAGTCGCATTCCTCAAATACCTCCCGGCAATTTCTTGATCCACCGGACAGCTAC

GACTGGTCGTGGACCTCGATTGGCACTGACGAGGCTATTGACACTGACTGCTGGGGGCTGTCCCA

ATGTGATGGAGGCTTCAGCTGTCAGTTACAGCCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

Table 6-continued

DNA Sequences of Variants of the lovE Gene

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCATCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCTCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-10

ATGGCTGCAGATCAAGGTATATTCACGAACTCGGTCACTCTCTCGCCAGTGGAGGGTTCACGCAC  (SEQ ID NO:75)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGATGCCCCAAGCGCAAGCTACGCCAATCCAGGGCAGCGGATCTCGT

CTCTGCTGACCCAGATCCCTGCTTGCACATGTCCTCGCCTCCAGTGCCCTCACAGAGCTTGCCGC

TAGACGTATCCGAGTCGCATTCCTCAAATACCTCCCGGCAATTTCTTGATCCACCGGACAGCTAC

GACTGGTCGTGGACCTCGATTGGCACTGACGAGGCTATTGACACTGACTGCTGGGGGCTGTCCCA

ATGTGATGGAGGCTTCAGCTGTCAGTTAGAGCCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCGTCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCTCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-16

ATGGCTGCAGATCAAGGTATATTCATGAACTCGGTCACTCTCTCTGCAGTGGAGGGTTCACGCAC  (SEQ ID NO:76)

CGGTGGAACATTACCCCGCCGTGCATTCCGACGCTCTTGTGATCGGTGTCATGCACAAAAGATCA

Table 6-continued

DNA Sequences of Variants of the lovE Gene

AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAATTTCTTGATCCACCGGACAGCTAC
GACTGGTCGTGGACCTCGATTGGCACTGACGAGGCTATTGACACTGACTGCTGGGGCTGTCCCA
ATGTGATGGAGGCTTCAGCTGTCAGTTACAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCATCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACTAGCAGCAGCAGCGGCCACAGCAGTGTTGAC
ACCATACCCTTCTTTAGCGAGAACCTCCCTATTGGTGAGCTGTTCTCCTATGTTGACCCCCTGAC
ACACGCCCTATTCTCGGCTTGCACTACGTTACATGTTGGGGTAGAATTGCTGCGTGAGAATGAGA
TTACTCTGGGAGTACACTCCGCCCAGGGCATTGCAGCTTCCATCAGCATGAGCGGGGAACCAGGC
GAGGATATAGCCAGGACAGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCCTCGCCCGCAAA
CACAAACATGGCATGCTCAGAGACCTCAACAATATTCCTCCATGA lovE-19

ATGGCTGCAGATCAAGGTATATTCACGAACTCGGTCACTCTCTCGCCAGTGGAGGGTTCACGCAC   (SEQ ID NO:77)
CGGTGGAACATTACCCCGCCGTGCATTCCGACGCTCTTGTGATCGGTGTCATGCACAAAAGATCA
AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAGTTTCTTGATCCACCGGACAGCTAC
GACTGGTCGTGGACCTCGATTGGCACTGACGAGGCTATTGACACTGACTGCTGGGGCTGTCCCA
ATGTGATGGAGGCTTCAGCTGTCAGTTAGAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCTCCTATGTTGACCCCCTGAC
ACACGCCCTATTCTCGGCTTGCACTACGTTACATGTTGGGGTACAATTGCTGCGTGAGAATGAGA

Table 6-continued

DNA Sequences of Variants of the lovE Gene

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCACAGTACTGCGACGATGCTATGAGGATATCTTTTCCCTCGCCCGCAAA

CACAAACATGGCATGCTCAGAGACCTCAACAATATTCCTTCATGA lovE-20

ATGGCTGCAGATCAAGGTATATTCACGAACTCGGTCACTCTCTCGCCAGTGGAGGGTTCACGCAC  (SEQ ID NO:78)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGATGCCCCAAGCGCAAGCTACGCCAATCCAGGGCAGCGGATCTCGT

CTCTGCTGACCCAGATCCCTGCTTGCACATGTCCTCGCCTCCAGTGCCCTCACAGAGCTTGCCGC

TAGACGTATCCGAGTCGCATTCCTCAAATACCTCCCGGCAATTTCTTGATCCACCGGACAGCTAC

GACTGGTCGTGGACCTCGATTGGCACTGACGAGGCTATTGACACTGACTGCTGGGGCTGTCCCA

ATGTGATGGAGGCTTCAGCTGTCAGTTACAGCCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCATCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCCCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-21

ATGGCTGCAGATCAAGGTATATTCACGAACTCGGTCACTCTCTCGCCAGTGGAGGGTTCACGCAC  (SEQ ID NO:79)

CGGTGGAACATTACCCCGCCGTGCACTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGATGCCCCAAGCGCAAGCTACGCCAATCCAGGGCAGCGGATCTCGT

CTCTGCTGACCCAGATCCCTGCTTGCACATATCCTCGCCTCCAGTGCCCTCACAGAGCTTGCCGC

TAGACGTATCCGATTCGCATTCCTCAAATACCTCCCGGCAATTTCTTGATCCACCGGACAGCTAC

GACTGGTCGTGGACCTCGATTGGCACTGACGAGGCTATTGACACTAACTGCTGGGGCTGTCCCA

ATGTGATGGAGGCTTCAGCTGTCAGTTACAGTCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

Table 6-continued

DNA Sequences of Variants of the lovE Gene

GGTAGAATGGCCTAAGCAGGAAATCTGGACCCATCCCATCGGAATGTTTTTCAATGCGTCACGAC
GGCTTCTTACTGTCCTGCGCCAACAAGCGCAGGCCGACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCTCCTATGTTGACCCCCTGAC
ACACGCCCTATTCTCGGCTTGCACTACGTTACATGTTGGGTACAATTGCTGCGTGAGATTGAGA
TTACTCTGGGAGTACACTCCGCCCAGGGCATTGCAGCTTCCATCAGCATGAGCGGGGAACCAGGC
GAGGATATAGCCAGGACAGGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCTCGCCCGCAAA
CACAAACATGGCATGCTCAGAGACCTCAACAATATTCCTCCATGA lovE-30

ATGGCTGCAGATCAAGGTATATTCACGAACTCGGTCACTCTCTCGCCAGTGGAGGGTTCACGCAC    (SEQ ID NO:80)
CGGTGGAACATTACCCCGCCGTGCATTCCGACGCTCTTGTGATCGGTGTCATGCACAAAAGATCA
AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAGTTTCTTGATCCACCGGACAGCTAC
GACTGGTCGTGGACCTCGATTGGCACTGACGAGGCTATTGACACTGACTGCTGGGGGCTGTCCCA
ATGTGATGGAGGCTTCAGCTGTCAGTTAGAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCATCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCTGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCTCCTATGTTGACCCCCTGAC
ACACGCCCTATTCTCGGCTTGCACTACGTTACATGTTGGGTACAATTGCTGCGTGAGAATGAGA
TTACTCTGGGAGTACACTCCGCCCAGGGCATTGCAGCTTCCATCAGCATGAGCGGGGAACCAGGC
GAGGATATAGCCAGGACAGGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCTCGCCCGCAAA
CACAAACATGGCATGCTCAGAGACCTCAACAATATTCCTCCATGA lovE-31

ATGGCTGCAGATCAAGGTATATTCACGAACTCCGTCACTCTCTCGCCAGTGGAGGGTTCACGCAC    (SEQ ID NO:81)
CGGTGGAACATTACCCCGCCGTGCATTCCGACGCTCTTGTGATCGGTGTCATGCACAAAAGATCA

Table 6-continued
DNA Sequences of Variants of the lovE Gene

AATGTACTGGAAATAAGGAGGTTACTGGCCGTGCTCCCTGTCAGCGTTGCCAGCAGGCTGGACTT

CGATGCGTCTACAGTGAGCGATGCCCCAAGCGCAAGTTACGCCAATCCAGGGCAGCGGATCTCGT

CTCTGCTGACCCAGATCCCTGCTTGCACATGTCCTCGCCTTCAGTGCCCTCACAGAGCTTGCCGC

TAGACGTATCCGAGTCGCATTCCTCAAATACCTCCCGGCAATTTCTTGATCCACCGGACAGCTAC

GACTGGTCGTGGACCTCGATTGGCACTGACGAGGCTATTGACACTGACTGCTGGGGCTGTCCCA

ACGTGATGGAGGCTTCAGCTCTCAGTTAAAGCCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCATCAAGGCACACTAGACGAATGT

TTACGGACCAAGAACCTCTTTACGGCAGTACACTGTTACATATTGAATGTGCGGATTTTGACCGC

CATATCGGAGTTGCTACTGTCGCAAATTAGGCTGACCCAGAACAGCCATATGAGCCCACTGGAAG

GGAGTCGATCCCAGTCGCCGAACAGAGACGACACCAGCAGCAGCAGCGGCCACAGCAGTGTTGAC

ACCATACCCTTCTTTAGCGAGAACCTCCCTATTGGTGAGCTGTTCTCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-32

ATGGCTGCAGATCAAGGTATATTCACTAACTCGGTCACTATCTCGCCAGTGGTGGGTTCACGCAC     (SEQ ID NO:82)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGATGCCCCAAGCGCAAGCTACGCCAATCCAGGGCAGCGGATCTCGT

CTCTGCTGACCCAGATCCCTGCTTGCACATGTCCTCGCCTCCAGTGCCCTCACAGAGTTTGCCGC

TAGACGTATCCGAGTCGCATTCCTCAAATACCTCCCGGCAATTTCTTGATCCACCGGACAGCTAC

GACTGGTCGTGGACCTCGATTTGCACTGACGAGGCTATTGACACTGACTGCTGGGGCTGTCCCA

ATGTGATGGAGGCTTCAGCTGTCAGTTAGAGCCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCATCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGGGCTGTTCTCCTATGTTGACCCCCTGAC

ACACGCCCTATTCTCGGCTTGCACTACGTTACATGTTGGGCTACAATTGCTGCGTGAGAATGAGA

TTACTCTGGGAGTACACTCCGCCCAGGGCATTGCAGCTTCCATCAGCATGAGCGGGGAACCAGGC

Table 6-continued

DNA Sequences of Variants of the lovE Gene

GAGGATATAGCCAGGACAGGGGCGACCAGTTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCCTCGCCCGCAAA
CACAAACATGGCATGCTCAGAGACCTCAACAATATTCCTCCATGA lovE-33

ATGGCTGCAGATCAAGGTATATTCACGAACTCGGTCACTCTCTCGCCAGTGGAGGGTTCACGCAC (SEQ ID NO:83)
CGGTGGAACATTACCCCGCCGTGCATTCCGACGCTCTTGTGATCGGTGTCATGCACGAAAGATCA
AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAATTTCTTGATCCACCGGACAGCTAC
GACTGGTCGTGGACCTCGATTGGCACTGACGAGGCTATTGACACTGACTGCTGGGGGCTGTCCCA
ATGTGATGGAGGCTTCAGCTGTCAGTTAAAGCCAACGCTGCCGGATCTACCTTCGCCCTTCGAGT
ATACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCAACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCCCCTATGTTGACCCCCTGAC
ACACGCCCTATTCTCGGCTTGCACTACGTTACATGTTGGGGTACAATTGCTGCGTGAGAATGAGA
TTACTCTGGGAGTACACTCCGCCCAGGGCATTGCAGCTTACATCAGCATCAGCGGGGAACCAGGC
GAGGATATAGCCAGGACAGGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCCTCGCCCGCAAA
CACAAACATGGCATGCTCAGAGACCTCAACAATATTCCTCCATGA lovE-34

ATGGCTGCAGATCAAGGTATATTCACGAACTCGGTCACTCTCTCGCCAGTGGAGGGTTCACGCAC (SEQ ID NO:84)
CGGTGGAACATTACCCCGCCGTGCATTGCGACGCTCTTGTGATCGGTGTCATGCACAAAAGATCA
AATGTACTGGAAATAAGGAGGTTATTGGCCGTGCTCCCTGTCAGCGTTGCCAGCAGGCTGGACTT
CGATGCGTATACAGTGAGCGATGCCCCAAGCGCAAGCTACGCCAATCCAGGGCAGCGGATCTCGT
CTCTGCTGACCCAGATCCCTGCTTGCACATGTCCTCGCCTCAAGTGCCCTCACAGAGCTTGTCGC
TAGACATATCCGAGTCGCATTCCTCAAATACCTCCCGGCAATTTCTTGATCCACCGGACAGCTAC
GACTGGTCGTGGACCTCGATTGGCACTGACGAGGCTATTGACACTGACTGCTGGGGGCTGTCCCA
ATGTGATGGAGGCTTCAGCTGTTAGTTAGAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC

Table 6-continued

DNA Sequences of Variants of the lovE Gene

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCGTCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTCGAC

ACCATACCCTTCTTTAGCGAGAACCTCCCTATTGGTGAGCTGTTCTCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCATTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGATCTCAACAATATTCCTCCATGA lovE-36

ATGGCTGCAGATCAAGGTATATTCACGAACTCGGTCACTCTCTCACCAGTGGAGGGTTCACGCAC (SEQ ID NO:85)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGATGCCCCAAGCGCAAGTACGCCAATCCAGGGCAGCGGATCTCGT

CTCTGCTGACCCAGATCCCTGCTTACACATGTCCTCGCCTCCAGTGCCCTCACAGAGCTTGCCGC

TAGACGTATCCGAGTCGCATTCCTCAAATACCTCCCGGCAATTTCTTGATCCACCGGACAGCTAC

GACTGGTCGTGGACCTCGATTGGCACTGACGAGGCTATTGACACTGACTGCTGGGGGCTGTCCCA

ATGTGATGGAGGCTTCAGCTGTCAGCTAGAGCCAACGCTGCCGGATCTACCTTCGCCCTTCGAGT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCGTCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCTCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-37

ATGGCTGCAGATCAAGGTATATTCACGAACTCGGTCACTCTCTCGCCAGTGGAGGGTTCACGCAC (SEQ ID NO:86)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

Table 6-continued

DNA Sequences of Variants of the lovE Gene

CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAGTTTCTTGATCCACCGGACAGCTAC
GACTGGTCGTGGACCTCGATTGGCACTGACGAGGCTATTGACACTGACTGCTGGGGGCTGTCCCA
ATGTGATGGAGGCTTCAGCTGTCAGTTACAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCGTCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGCCGAGCAGAGACGACACCAGCAGCAGCAGCGGCCACAGCAGTGTTGAC
ACCATACCCTTCTTTAGCGAGAACCTCCCTATTGGTGAGCTGTTCCCCTATGTTGACCCCCTGAC
ACACGCCCTATTCTCGGCTTGCACTACGTTACATGTTGGGGTACAATTGCTGCGTGAGAATGAGA
TTACTCTGGGAGTACACTCCGCCCAGGGCATTGCAGCTTCCATCAGCATGAGCGGGGAACCAGGC
GAGGATATAGCCAGGACAGGGGCGACCAATTCCGCAAGATGCGAGGAGCAGCCGACCACTCCAGC
GGCTCGGGTTTTGTTCATGTTCTTGAGTGATGAAGGGGCTTTCCAGGAGGCAAAGTCTGCTGGTT
CCCGAGGTCGAACCATCGCAGCACTGCGACGATGCTATGAGGATATCTTTTCCCTCGCCCGCAAA
CACAAACATGGCATGCTCAGAGACCTCAACAATATTCCTCCATGA lovE-38

ATGGCTGCAGATCAAGGTATATTCACGAACTCGGTCACTCTCTCGCCAGTGGAGGGTTCACGCAC    (SEQ ID NO:87)
CGGTGGAACATTACCCCGCCGTGCATTCCGACGCTCTTGTGATCGGTGTCATGCACAAAAGATCA
AATGTACTGGAAATAAGGAGGTTACTGGCCGTGCTCCCTGTCAGCGTTGCCAGCAGGCTGGACTT
CGATGCGTCTACAGTGAGCGATGCCCCAAGCGCAAGCTACGCCAATCCAGGGCAGCGGATCTCGT
CTCTGCTGACCCAGATCCCTGCTTGCACATGTCCTCGCCTCCAGTGCCCTCACAGAGCTTGCCGC
TAGACGTATCCGAGTCGCATTCCTCAAATACCTCCCGGCAGTTTCTTGATCCACCGGACAGCTAC
GACTGGTCGTGGACCTCGATTGGCACTGACGAGGCTATTGACACTGACTGCTGGGGGCTGTCCCA
ATGTGATGGAGGCTTCAGCTGTCAGCTAGAGCCAACGCTGCCGGATCTACCTTCGCCCTTCGAGT
CTACGGTTGAAAAAGCTCCGTTGCCACCGGTATCGAGCGACATTGCTCGTGCGGCCAGTGCGCAA
CGAGAGCTTTTCGATGACCTGTCGGCGGTGTCGCAGGAACTGGAAGAGATCCTTCTGGCCGTGAC
GGTAGAATGGCCGAAGCAGGAAATCTGGACCCATCCCATCGGAATGTTTTTCAATGCGTCACGAC
GGCTTCTTACTGTCCTGCGCCAACAAGCGCAGGCCGACTGCCATCAAGGCACACTAGACGAATGT
TTACGGACCAAGAACCTCTTTACGGCAGTACACTGTTACATATTGAATGTGCGGATTTTGACCGC
CATATCGGAGTTGCTCCTGTCGCAAATTAGGCGGACCCAGAACAGCCATATGAGCCCACTGGAAG
GGAGTCGATCCCAGTCGATGAGCAGAGACGACACCAGCAGCAGCAGCGGCCACAGTAGTGTTGAC
ACCATACCCTTCTTTAGCGAGAACCTCCCTATTGGTGAGCTGTTCTCCTATGTTGACCCCCTGAC
ACACGCCCTATTCTCGGCTTGCACTACGTTACATGTTGGGGTACAATTGCTGCGTGAGAATGAGA
TTACTCTGGGAGTACACTCCGCCCAGGGCATTGCAGCTTCCATCAGCATGAGCGGGGAACTAGGC

Table 6-continued

DNA Sequences of Variants of the lovE Gene

GAGGATATAGTCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAAGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-39

ATGGCTGCAGATCAAGGTATATTCACGAACTCGGTCACTCTCTCACCAGTGGAGGGTTCACGCAC   (SEQ ID NO:88)

CGGTGGAACATTACCCCGCCGTGCATTCCGACGCTCTTGTGATCGGTGTCATGCACAAAAGATCA

AATGTACTGGAAATAAGGAGGTTAATGGCCGTGCTCCCTGTCAGCGTTGCCAGCAGGCTGGACTT

CGATGCGTCTACAGTGAGCGATGCCCCAAGCGCAAGCTACGCCAATCCAGGGCAGCGGATCTCGT

CTCTGCTGACCCAGATCCCTGCTTGCACATGTCCTCGCCTCCAGTGCCCTCCCAGAGCTTGCCGC

TAGACATATCCGAGTCGCATTCCTCAAATACCTCCCGGCAATTTCTTGATCCACCGGACAGCTAC

GACTGGTCGTGGACCTCGATTGGCATTGACGAGGCTATTGACACTGACTGCTGGGGGCTGTCCCA

ATGTGATGGAGGCTTCAGCTGTCAGTTAGAGCCAACGCTGCCGGATCTACCTTCGCCCTTCGAGT

CTACGGTTGAAAAAGCTCCGTTGCCACCGATATCGAGCGACATTGCTCGTGCGGCCAGTGCGCAA

CGAGAGCTTTTCGATGACCTGACGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCATCAAGGCACACTAGACGAATGT

TTACGGACCAAGAACCTCTTTACGGCAGTACACTGTTACATATTGAATGTGCGGATTTTGGCCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCCCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-40

ATGGCTGCAGAACAAGGTATATTCACGAACTCGGTCACTCTCTCGCCAGTGGAGGGTTCACGCAC   (SEQ ID NO:89)

CGGTGGAACATTACCCCGCCGTGCATTCCGACGCTCTTGTGATCGGTGTCATGCACGAAAGATCA

AATGTACTGGAAATAAGGAGGTTACTGGCCGTGCTCCCTGTCAGCGTTGCCAGCAGGCTGGACTT

CGATGTGTCTACAGTGAGCGATGCCCCAAGCGCAAGCTACGCCAATCCAGGGCAGCGGATCTCAT

CTCTGCTGACCCAGATCCCTGCTTGCACATGTCCTCGCCTCCAGTGCCCTCACAGAGCTTGCCGC

TAGAAGTATCCGAGTCGCATTCCTCAAATACCTCCCGGCAATTTCTTGATCCACCGGACAGCTAC

GACTGGTCGTGGACCTCGATTGGCACTGACAAGGCTATTGACACTGACTGCTGGGGGCTGTCCCA

ATGTGATGGAGGCTTCAGCTGTCAGTTAGAGCCAACGCTGCCGGATCTACCTTCGCCCTTTGAGT

CTACGGTTGAAAAAGCTCCGTTGCCACCGGTATCGAGCGACATTACTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

Table 6-continued

DNA Sequences of Variants of the lovE Gene

GGCTTCTTACTGTCCTGCGCCAACAAGCGCAGGCCGACTGCCGTCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCTCCTATGTTGACCCCCTGAG

ACACGCCCTATTCTCGGCTTGCACTACGTTACATGTTGGGGTACAATTGCTGCGTGAGATTGAGA

TTACTCTGGGAGTACACTCCGCCCGGGGCATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGACTTTCCAGGAGGCAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA lovE-41

ATGGCTGCAGATCAAGGTATATTCACGAACTCGGTCACTCTCTCGCCAGTGGAGGGTTCACGCAC (SEQ ID NO:90)

CGGTGGAACATTACCCCGCCGTGCATTCCGACGCTCTTGTGATCGGTGTCATGCACAAAAGATCA

AATGTACTGGAAATAAGGAGGTTACTGGCCGTGCTCCCTGTCAGCGTTGCCAGCAGGCTGGACTT

CGATGCGTCTACAGTGAGCGATGCCCCAAGCGCAAGCTACGCCAATCCAGGGCAGCGGATCTCGT

CTCTGCTGACCCAGATCCCTGCTTGCACATGTCCTCACCTCCAGTGCCCTCACAGAGCTTGCCGC

TAGACGTATCCGAGTCGCATTCCTCAAATACCTCCCGGCAGTTTCTTGATCCACCGGACAGCTAC

AACTGGTTGTGGACCTCGATTGGCACTGACGAGGCTATTGACACTGACTGCTGGGGGCTGTCCCA

ATGTGATGGAGGCTTCAGCTGTCAGTTAGAGCCAACGCTGCCGGATCTACCTTCGCCCTTCGAAT

CTACGGTTGAAAAAGCTCCGTTGCCACCGGTATCGAGCGACATTGCTCGTGCGGCCAGTGCGCAA

CGAGAGCTTTTCGATGACCTGTCGGCGGTGTCGCAGGAACTGGAAGAGATCCTTCTGGCCGTGAC

GGTAGAATGGCCGAAGCAGGAAATCTGGACCCATCCCATCGGAATGTTTTTCAATGCGTCACGAC

GGCTTCTTACTGTCCTGCGCCAACAAGCGCAGGCCGACTGCCGTCAAGGCACACTAGACGAATGT

TTACGGACCAAGAACCTCTTTACGGCAGTACACTGTTACATATTGAATGTGCGGATTTTGACCGC

CATATCGGAGTTGCTCCTGTCGCAAATTAGGCGGACCCAGAACAGCCATATGAGCCCACTGGAAG

GGAGTCGATCCCAGTCGCCGAGCAGAGACGACACCAGCAGCAGCAGCGGCCACAGCAGTGTTGAC

ACCATACCCTTCTTTAGCGAGAACCTCCCTATTGGTGAGCTGTTCTCCTATGTTGACCCCCTGAC

ACACGCCCTATTCTCGGCTTGCACTACGTTACATGTTGGGGTACAATTGCTGCGTGAGAATGAGA

TTACTCTGGGAGTACACTCCGCCCAGGGTATTGCAGCTTCCATCAGCATGAGCGGGGAACCAGGC

GAGGATATAGCCAGGACAGGGGCGACCAATTCCGCAAGATGCGAGGAGCAGCCGACCACTCCAGC

GGCTCGGGTTTTGTTCATGTTCTTGAGTGATGAAGGGGCTTTCCAGGAGGGAAAGTCTGCTGGTT

CCCGAGGTCGAACCATCGCAGCACTGCGACGATGCTATGAGGATATCTTTTCCCTCGCCCGCAAA

CACAAACATGGCATGCTCAGAGACCTCAACAATATTCCTCCATGA

EQUIVALENTS

Those skilled in the art will recognize, or be able to ascertain, using no more than routine experimentation, many equivalents to the specific embodiments of the invention described herein. Such equivalents are intended to be encompasssed by the following claims.

What is claimed is:

1. An isolated nucleic acid molecule comprising a nucleotide sequence encoding a polypeptide comprising an amino acid sequence that is identical to the amino acid sequence of SEQ ID NO:91 except for the presence of at least one amino acid change selected from the group consisting of:

(a) a phenylalanine changed to valine, leucine, isoleucine, or methionine at position 31;
(b) a glutamine changed to lysine, arginine or histidine at position 41;
(c) a threonine changed to valine, leucine, isoleucine, or methionine at position 52;
(d) a threonine changed to aspartic acid, glutamic acid, asparagine or glutamine at position 52;
(e) a cysteine changed to lysine, arginine or histidine at position 73;
(f) a proline changed to serine, threonine or cysteine at position 101;
(g) a proline changed to aspartic acid, glutamic acid, asparagine or glutamine at position 101;
(h) a valine changed to leucine, isoleucine, or methionine at position 111;
(i) a serine changed to valine, leucine, isoleucine, or methionine at position 133;
(j) a glutamic acid changed to valine, leucine, isoleucine, or methionine at position 141;
(k) a glutamic acid changed to lysine, arginine or histidine at position 141;
(l) a cysteine changed to phenylalanine, tyrosine or tryptophan at position 153;
(m) a cysteine changed to lysine, arginine or histidine at position 153;
(n) a threonine changed to glycine, alanine or proline at position 281;
(o) a asparagine changed to valine, leucine, isoleucine, or methionine at position 367;

(p) a asparagine changed to phenylalanine, tyrosine or tryptopthan at position 367;
(q) a proline changed to serine, threonine or cysteine at position 389; and
(r) a proline changed to valine, leucine, isoleucine, or methionine at position 389.

2. The isolated nucleic acid molecule of claim 1 wherein the polypeptide when expressed in an *A. terreus* cell harboring a lovF gene increases expression of the lovF gene relative to an otherwise identical cell not expressing the polypeptide.

3. The isolated nucleic acid molecule of claim 1 wherein the polypeptide when expressed in an *S. cerevisiae* cell harboring a gene under the control of the *A. terreus* lovF expression control region increases expression of the gene relative to an otherwise identical cell not expressing the polypeptide.

4. The isolated nucleic acid molecule of claim 1 wherein the polypeptide includes the amino acid change phenylalanine changed to leucine at position 31.

5. The isolated nucleic acid molecule of claim 1 wherein the polypeptide includes the amino acid change glutamine changed to lysine or arginine at position 41.

6. The isolated nucleic acid molecule of claim 1 wherein the polypeptide includes the amino acid change threonine changed to isoleucine at position 52.

7. The isolated nucleic acid molecule of claim 1 wherein the polypeptide includes the amino acid change threonine changed to asparagine at position 52.

8. The isolated nucleic acid molecule of claim 1 wherein the polypeptide includes the amino acid change cysteine changed to arginine at position 73.

9. The isolated nucleic acid molecule of claim 1 wherein the polypeptide includes the amino acid change proline changed to serine at position 101.

10. The isolated nucleic acid molecule of claim 1 wherein the polypeptide includes the amino acid change proline changed to glutamine at position 101.

11. The isolated nucleic acid molecule of claim 1 wherein the polypeptide includes the amino acid change valine changed to isoleucine at position 111.

12. The isolated nucleic acid molecule of claim 1 wherein the polypeptide includes the amino acid change S133L serine changed to leucine at position 133.

13. The isolated nucleic acid molecule of claim 1 wherein the polypeptide includes the amino acid change glutamic acid changed to valine at position 141.

14. The isolated nucleic acid molecule of claim 1 wherein the polypeptide includes the amino acid change glutamic acid changed to lysine at position 141.

15. The isolated nucleic acid molecule of claim 1 wherein the polypeptide includes the amino acid change cysteine changed to tyrosine at position 153.

16. The isolated nucleic acid molecule of claim 1 wherein the polypeptide includes the amino acid change cysteine changed to arginine at position 153.

17. The isolated nucleic acid molecule of claim 1 wherein the polypeptide includes the amino acid change threonine changed to alanine at position 281.

18. The isolated nucleic acid molecule of claim 1 wherein the polypeptide includes the amino acid change asparagine changed to isoleucine at position 367.

19. The isolated nucleic acid molecule of claim 1 wherein the polypeptide includes the amino acid change asparagine changed to tyrosine at position 367.

20. The isolated nucleic acid molecule of claim 1 wherein the polypeptide includes the amino acid change proline changed to serine at position 389.

21. The isolated nucleic acid molecule of claim 1 wherein the polypeptide includes the amino acid change proline changed to leucine at position 389.

22. The isolated nucleic acid molecule of claim 1 wherein the nucleotide sequence encoding the polypeptide is contiguous.

23. A fungal cell containing a recombinant nucleic acid molecule comprising the nucleic acid molecule of claim 1.

24. The fungal cell of claim 23 wherein the fungus is *A. terreus*.

25. The fungal cell of claim 23 wherein the fungus is *S. cerevisiae*.

26. A vector comprising the isolated nucleic acid molecule of claim 1.

27. The vector of claim 26, wherein the vector is an expression vector.

28. An isolated nucleic acid molecule comprising a nucleotide sequence selected from the group consisting of: SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, and SEQ ID NO:90.

29. An isolated nucleic acid molecule comprising a nucleotide sequence encoding a polypeptide comprising the amino acid sequence of SEQ ID NO:91 except for the presence of a glutamic acid changed to lysine, arginine or histidine at position 141.

30. An isolated nucleic acid molecule comprising a nucleotide sequence encoding a polypeptide comprising the amino acid sequence of SEQ ID NO:91 except for the presence of a cysteine changed to phenylalanine, tyrosine or tryptophan at position 153.

31. An isolated nucleic acid molecule comprising a nucleotide sequence encoding a polypeptide comprising the amino acid sequence of SEQ ID NO:91 except for the presence of a cysteine changed to lysine, arginine or histidine at position 153.

32. An isolated nucleic acid molecule comprising a nucleotide sequence encoding a polypeptide comprising the amino acid sequence of SEQ ID NO:91 except for the presence of a threonine changed to glycine, alanine or proline at position 281.

33. An isolated nucleic acid molecule comprising a nucleotide sequence encoding a polypeptide comprising the amino acid sequence of SEQ ID NO:91 except for the presence of an asparagine changed to valine, leucine, isoleucine or methionine at position 367.

34. An isolated nucleic acid molecule comprising a nucleotide sequence encoding a polypeptide comprising the amino acid sequence of SEQ ID NO:91 except for the presence of an asparagine changed to phenylalanine, tyrosine or tryptophan at position 367.

35. An isolated nucleic acid molecule comprising a nucleotide sequence encoding a polypeptide comprising the amino acid sequence of SEQ ID NO:91 except for the presence of a proline changed to serine, threonine or cysteine at position 389.

36. An isolated nucleic acid molecule comprising a nucleotide sequence encoding a polypeptide comprising the amino acid sequence of SEQ ID NO:91 except for the presence of a proline changed to valine, leucine, isoleucine, or methionine at position 389.

* * * * *